(12) United States Patent
Gottlieb et al.

(10) Patent No.: US 10,327,678 B2
(45) Date of Patent: Jun. 25, 2019

(54) ANALYTE SENSOR APPARATUSES COMPRISING MULTIPLE IMPLANTABLE SENSOR ELEMENTS AND METHODS FOR MAKING AND USING THEM

(71) Applicant: Medtronic MiniMed, Inc., Northridge, CA (US)

(72) Inventors: Rebecca K. Gottlieb, Culver City, CA (US); Rajiv Shah, Rancho Palos Verdes, CA (US); Eric A. Larson, Simi Valley, CA (US); Chia Chiu, Granada Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1279 days.

(21) Appl. No.: 14/247,478

(22) Filed: Apr. 8, 2014

(65) Prior Publication Data

US 2014/0275899 A1 Sep. 18, 2014

Related U.S. Application Data

(62) Division of application No. 12/184,117, filed on Jul. 31, 2008, now Pat. No. 8,700,114.

(51) Int. Cl.
| | | |
|---|---|---|
| *A61B 5/00* | (2006.01) | |
| *A61B 5/145* | (2006.01) | |
| *A61B 5/1473* | (2006.01) | |
| *A61B 5/1486* | (2006.01) | |
| *C12Q 1/00* | (2006.01) | |

(52) U.S. Cl.
CPC ........ *A61B 5/14532* (2013.01); *A61B 5/1473* (2013.01); *A61B 5/14865* (2013.01); *A61B 5/6848* (2013.01); *A61B 5/6849* (2013.01); *C12Q 1/006* (2013.01)

(58) Field of Classification Search
CPC ............. A61B 5/14532; A61B 5/1473; A61B 5/14865; A61B 5/6849; A61B 5/6848; C12Q 1/006

See application file for complete search history.

(56) References Cited

U.S. PATENT DOCUMENTS

| | | |
|---|---|---|
| 4,356,074 A | 10/1982 | Johnson |
| 4,680,286 A * | 7/1987 | Stockel .................. A61K 33/04 514/23 |
| 4,755,173 A | 7/1988 | Konopka et al. |
| 4,971,901 A | 11/1990 | Hayashi et al. |

(Continued)

FOREIGN PATENT DOCUMENTS

| | | |
|---|---|---|
| WO | 98/38906 | 9/1998 |
| WO | 98/46124 | 10/1998 |

(Continued)

OTHER PUBLICATIONS

International Search Report dated Feb. 2, 2010, International application No. PCT/US2009/052506, International filing date Jul. 31, 2009.

*Primary Examiner* — Tiffany Weston

(74) *Attorney, Agent, or Firm* — Gates & Cooper LLP

(57) ABSTRACT

Embodiments of the invention provide analyte sensors having optimized elements and/or configurations of elements as well as methods for making and using such sensors. Typical embodiments of the invention include glucose sensors used in the management of diabetes.

18 Claims, 29 Drawing Sheets

Distributed Electrodes
78/78 (100%) start immediately

(56) References Cited

U.S. PATENT DOCUMENTS

| | | |
|---|---|---|
| 5,063,081 A | 11/1991 | Cozzette et al. |
| 5,120,420 A | 6/1992 | Nankai et al. |
| 5,192,415 A | 3/1993 | Yoshioka et al. |
| 5,200,051 A | 4/1993 | Cozzette et al. |
| 5,299,571 A | 4/1994 | Mastrototaro |
| 5,310,475 A | 5/1994 | Kitada et al. |
| 5,352,348 A | 10/1994 | Young et al. |
| 5,391,250 A | 2/1995 | Cheney, II et al. |
| 5,485,408 A | 1/1996 | Blomquist |
| 5,522,803 A | 6/1996 | Teissen-Simony |
| 5,641,767 A | 6/1997 | Wess et al. |
| 5,651,767 A | 7/1997 | Schulman et al. |
| 5,660,163 A * | 8/1997 | Schulman ......... A61B 5/14865 204/403.11 |
| 5,665,065 A | 9/1997 | Colman et al. |
| 5,696,314 A | 12/1997 | McCaffrey et al. |
| 5,773,270 A | 6/1998 | D'Orazio et al. |
| 5,800,420 A | 9/1998 | Gross et al. |
| 5,804,048 A | 9/1998 | Wong et al. |
| 5,807,375 A | 9/1998 | Gross et al. |
| 5,837,454 A | 11/1998 | Cozzette et al. |
| 5,914,026 A | 6/1999 | Blubaugh, Jr. et al. |
| 5,925,021 A | 7/1999 | Castellano et al. |
| 5,954,643 A | 9/1999 | Van Antwerp et al. |
| 5,965,380 A * | 10/1999 | Heller ............... C12Q 1/006 435/14 |
| 5,972,199 A | 10/1999 | Heller et al. |
| 6,017,328 A | 1/2000 | Fischell et al. |
| 6,030,827 A | 2/2000 | Davis et al. |
| 6,091,975 A | 7/2000 | Daddona et al. |
| 6,119,028 A | 9/2000 | Schulman et al. |
| 6,175,752 B1 | 1/2001 | Say et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,336,904 B1 | 1/2002 | Nikolchev |
| 6,355,021 B1 | 3/2002 | Nielsen et al. |
| 6,379,301 B1 | 4/2002 | Worthington et al. |
| 6,466,810 B1 | 10/2002 | Ward et al. |
| 6,544,212 B2 | 4/2003 | Galley et al. |
| 6,558,351 B1 | 5/2003 | Steil et al. |
| 6,560,471 B1 | 5/2003 | Heller et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,814,844 B2 | 11/2004 | Bhullar et al. |
| 6,849,463 B2 | 2/2005 | Santini, Jr. et al. |
| 6,916,294 B2 | 7/2005 | Ayad |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,613,491 B2 | 11/2009 | Boock et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2001/0051768 A1 | 12/2001 | Schulman et al. |
| 2002/0023852 A1 | 2/2002 | Mcivor et al. |
| 2002/0031532 A1 | 3/2002 | Uchiyama |
| 2002/0032374 A1 | 3/2002 | Holker et al. |
| 2003/0124623 A1 | 7/2003 | Yager et al. |
| 2003/0155237 A1 | 8/2003 | Surridge et al. |
| 2004/0064156 A1 | 4/2004 | Shah et al. |
| 2004/0074785 A1 | 4/2004 | Holker et al. |
| 2004/0106857 A1 | 6/2004 | Gough |
| 2004/0182722 A1 | 9/2004 | Blomberg et al. |
| 2005/0000808 A1 | 1/2005 | Cui et al. |
| 2005/0008671 A1 | 1/2005 | Van Antwerp |
| 2005/0054909 A1 | 3/2005 | Petisce et al. |
| 2005/0101023 A1 | 5/2005 | Rogers et al. |
| 2005/0103625 A1 | 5/2005 | Rhodes et al. |
| 2005/0143675 A1 | 6/2005 | Neel et al. |
| 2005/0148832 A1 * | 7/2005 | Reghabi ............... A61B 5/01 600/309 |
| 2005/0205422 A1 | 9/2005 | Moser et al. |
| 2005/0245799 A1 | 11/2005 | Brauker et al. |
| 2005/0272989 A1 | 12/2005 | Shah et al. |
| 2006/0004272 A1 | 1/2006 | Shah et al. |
| 2006/0052745 A1 | 3/2006 | Van Antwerp et al. |
| 2006/0253085 A1 | 11/2006 | Geismar et al. |
| 2006/0293576 A1 | 12/2006 | Van Antwerp et al. |
| 2007/0027384 A1 * | 2/2007 | Brister ............... A61B 5/14532 600/365 |
| 2007/0078320 A1 * | 4/2007 | Stafford ............ A61B 5/14532 600/347 |
| 2007/0123819 A1 | 5/2007 | Mernoe et al. |
| 2007/0135689 A1 | 6/2007 | Asukai et al. |
| 2007/0170073 A1 | 7/2007 | Wang et al. |
| 2007/0208244 A1 | 9/2007 | Brauker et al. |
| 2007/0227907 A1 | 10/2007 | Shah et al. |
| 2008/0026473 A1 | 1/2008 | Wang et al. |
| 2008/0027281 A1 | 1/2008 | Chang |
| 2008/0249383 A1 * | 10/2008 | Sass ................. A61B 5/14865 600/345 |
| 2009/0198117 A1 | 8/2009 | Cooper et al. |
| 2010/0160861 A1 | 6/2010 | Causey, III et al. |

(56) References Cited

U.S. PATENT DOCUMENTS

2010/0285084 A1  11/2010  Yang et al.
2011/0152654 A1  6/2011  Wang et al.

FOREIGN PATENT DOCUMENTS

WO  05/048834  6/2005
WO  2006/062668  6/2006

* cited by examiner

Switched Electrodes
29/36 (81%) start immediately

Distributed Electrodes
78/78 (100%) start immediately

ANALYTE SENSOR APPARATUSES COMPRISING MULTIPLE IMPLANTABLE SENSOR ELEMENTS AND METHODS FOR MAKING AND USING THEM

CROSS REFERENCE TO RELATED APPLICATIONS

This application is a divisional application that claims the benefit under 35 U.S.C. § 120 of U.S. patent application Ser. No. 12/184,117, filed Jul. 31, 2008, the contents of which are incorporated herein by reference.

This application is related to U.S. patent application Ser. No. 10/861,837, U.S. patent application Ser. No. 11/149,119, U.S. patent application Ser. No. 11/301,512, now U.S. Pat. No. 7,813,780, issued Oct. 12, 2010, U.S. patent application Ser. No. 11/397,543, U.S. patent application Ser. No. 11/492,273, U.S. patent application Ser. No. 11/897,106, U.S. patent application Ser. No. 11/966,294, now U.S. Pat. No. 8,114,269, issued Feb. 14, 2012, and U.S. patent application Ser. No. 11/323,242, the contents of each of which are incorporated herein by reference.

BACKGROUND OF THE INVENTION

1. Field of the Invention

Analyte sensors (e.g. glucose sensors used in the management of diabetes) and methods and materials for making and using such sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

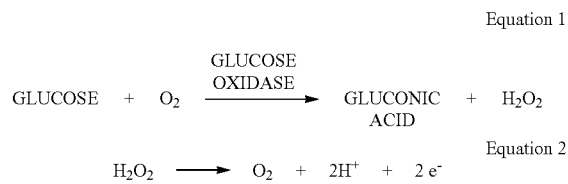

Equation 1

$$GLUCOSE + O_2 \xrightarrow{GLUCOSE\ OXIDASE} GLUCONIC\ ACID + H_2O_2$$

Equation 2

$$H_2O_2 \longrightarrow O_2 + 2H^+ + 2e^-$$

The glucose oxidase is used to catalyze the reaction between glucose and oxygen to yield gluconic acid and hydrogen peroxide (equation 1). The $H_2O_2$ reacts electrochemically as shown in equation 2, and the current can be measured by a potentiostat. These reactions, which occur in a variety of oxidoreductases known in the art, are used in a number of sensor designs.

As analyte sensor technology matures and new applications for sensor technology are developed, there is a need for methods and materials that facilitate the use of sensors in the wide variety of situations in which the measurement of an analyte is desirable.

SUMMARY OF THE INVENTION

Embodiments of the invention disclosed herein include analyte sensors and sensor systems such as amperometric glucose sensors used in the management of diabetes as well as optimized methods for monitoring analytes using such sensors and sensor systems. One embodiment of the invention is an analyte sensor apparatus comprising: an elongated base layer; a conductive layer disposed on the base layer and comprising a reference electrode, a working electrode and a counter electrode; an analyte sensing layer disposed on the conductive layer; an analyte modulating layer disposed on the analyte sensing layer, wherein the analyte modulating layer comprises a composition that modulates the diffusion of an analyte diffusing through the analyte modulating layer; and a cover layer disposed on the analyte sensor apparatus, wherein the cover layer comprises an aperture positioned on the cover layer so as to facilitate an analyte contacting and diffusing through the analyte modulating layer and contacting the analyte sensing layer. Typical embodiments of the invention are comprised of biocompatible materials and/or have structural elements and organizations of elements designed for implantation within a mammal. Methodological embodiments of the invention include methods for making and using the sensor embodiments disclosed herein. Certain embodiments of the invention include methods of using a specific sensor element and/or a specific constellation of sensor elements to produce and/or facilitate one or more properties of the sensor embodiments disclosed herein (e.g. sensor initialization and start-up).

In some embodiments of the invention, an element of the sensor apparatus such as an electrode or an aperture is designed to have a specific configuration and/or is made from a specific material and/or is positioned relative to the other elements so as to facilitate a function of the sensor. In one such embodiment of the invention, a working electrode, a counter electrode and a reference electrode are positionally distributed on the base and/or the conductive layer in a configuration that facilitates sensor start up and/or maintains the hydration of the working electrode, the counter electrode and/or the reference electrode when the sensor apparatus is placed in contact with a fluid comprising the analyte (e.g. by inhibiting shadowing of an electrode, a phenomena which can inhibit hydration and capacitive start-up of a sensor circuit). Typically such embodiments of the invention facilitate sensor start-up and/or initialization.

Optionally embodiments of the apparatus comprise a plurality of working electrodes and/or counter electrodes and/or reference electrodes (e.g. 3 working electrodes, a reference electrode and a counter electrode), in order to, for example, provide redundant sensing capabilities. Certain embodiments of the invention comprising a single sensor. Other embodiments of the invention comprise multiple sensors. In some embodiments of the invention, a pulsed voltage is used to obtain a signal from one or more electrodes of a sensor. Optionally, the plurality of working, counter and reference electrodes are configured together as a unit and positionally distributed on the conductive layer in a repeating pattern of units. In certain embodiments of the invention, the elongated base layer is made from a flexible material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment.

In certain embodiments of the invention comprising multiple sensors, elements such as the sensor electrodes are organized/disposed within a flex-circuit assembly. In such embodiments of the invention, the architecture of the sensor system can be designed so that a first sensor does not influence a signal etc. generated by a second sensor (and vice versa); and so that the first and second sensors sense from separate tissue envelopes; so the signals from separate sensors do not interact. At the same time, in typical embodiments of the invention the sensors will be spaced at a distance from each other so that allows them to be easily packaged together and/or adapted to be implanted via a single insertion action. One such embodiment of the invention is an apparatus for monitoring an analyte in a patient, the apparatus comprising: a base element adapted to secure the apparatus to the patient; a first piercing member coupled to and extending from the base element; a first electrochemical sensor operatively coupled to the first piercing member and comprising a first electrochemical sensor electrode for determining at least one physiological characteristic of the patient at a first electrochemical sensor placement site; a second piercing member coupled to and extending from the base element; a second electrochemical sensor operatively coupled to the second piercing member and comprising a second electrochemical sensor electrode for determining at least one physiological characteristic of the patient at a second electrochemical sensor placement site. In such embodiments of the invention, at least one physiological characteristic monitored by the first or the second electrochemical sensor comprises a concentration of a naturally occurring analyte in the patient; the first piercing member disposes the first electrochemical sensor in a first tissue compartment of the patient and the second piercing member disposes the second electrochemical sensor in a second tissue compartment of the patient; and the first and second piercing members are disposed on the base in a configuration selected to avoid a physiological response that can result from implantation of the first electrochemical sensor from altering a sensor signal generated by the second electrochemical sensor.

In an embodiment of the invention that is designed to optimize electrode properties such as hydration, the working electrode, the counter electrode and the reference electrode are positionally distributed on conductive layer in a parallel configuration arranged so that a first electrode is disposed in a region on a first edge of the elongated base layer; a second electrode is disposed in a region on an opposite edge of the elongated base layer; and a third is disposed in a region of the elongated base layer that between the first electrode and the second electrode. Optionally, the working electrode, the counter electrode and the reference electrode are positionally distributed on conductive layer in a configuration arranged so that the working electrode is disposed in a region on a first edge of the elongated base layer; the counter electrode is disposed in a region on an opposite edge of the elongated base layer; and the reference electrode is disposed in a region of the elongated base layer that between the working electrode and the counter electrode. In certain embodiments of the invention, an edge or center of a reference electrode is lined up with an edge or center of the working or counter electrode. In other embodiments of the invention, an edge or center of a reference electrode is offset with an edge or center of the working or counter electrode. In some embodiments of the invention, an electrode matrix is formed in the sensor so as to have no side walls in a manner that further improve hydration of the sensor electrodes. Related embodiments of the invention include methods for using a distributed electrode configuration to facilitate and maintain the hydration and/or initialization properties of various sensor embodiments of the invention.

In some embodiments of the invention, one or more apertures is positioned on the cover layer so that a fluid comprising the analyte contacts the reference electrode, the working electrode and the counter electrode in a sequential manner so as to facilitate sensor hydration and/or sensor start-up or initialization. In other embodiments of the invention, the aperture is positioned on the cover layer directly over the reference electrode, the working electrode and the counter electrode so that the hydration of these electrode proceeds equivalently. The cover layer can be constructed from a variety of materials know in the art and can include a variety of apertures having similar or dissimilar sizes, shapes and configurations. In some embodiments of the invention, the cover layer comprises a plurality of apertures (e.g. disposed in a row over the various sensor electrodes) and is formed from a sheath or tube made for example from a biocompatible polymeric material. Related embodiments of the invention include methods for using a specific aperture configuration to facilitate a property (e.g. initialization and/or start-up) of various sensor embodiments of the invention.

Various elements of the sensor apparatus can be disposed at a certain location in the apparatus and/or configured in a certain shape and/or be constructed from a specific material so as to facilitate strength and/or function of the sensor. One embodiment of the invention includes an elongated base comprised of a polyimide or dielectric ceramic material that facilitates the strength and durability of the sensor. In certain embodiments of the invention, the structural features and/or relative position of the working and/or counter and/or reference electrodes is designed to influence sensor manufacture, use and/or function. Optionally, the sensor is operatively coupled to a constellation of elements that comprise a flex-circuit (e.g. electrodes, electrical conduits, contact pads and the like). One embodiment of the invention includes electrodes having one or more rounded edges so as to inhibit delamination of a layer disposed on the electrode (e.g. an analyte sensing layer comprising glucose oxidase). Related embodiments of the invention include methods for inhibiting delamination of a sensor layer using a sensor embodiments of the invention (e.g. one having one or more electrodes having one or more rounded edges). In some embodiments of the invention, a barrier element is disposed on the apparatus so as to inhibit spreading of a layer of material (e.g. an enzyme such as glucose oxidase) disposed on an electrode. Related embodiments of the invention include methods for inhibiting movement of a compound disposed on a sensor embodiments of the invention (e.g. one constructed to have such a barrier structure). Optionally, a barrier element is disposed on the apparatus so as to encircle a reactive surface of an electrode.

In certain embodiments of the invention, an electrode of the apparatus comprises a platinum composition and the apparatus further comprises a titanium composition disposed between the elongated base layer and the conductive layer. Optionally in such embodiments, apparatus further comprises a gold composition disposed between the titanium composition and the conductive layer. Such embodiments of the invention typically exhibit enhanced bonding between layered materials within the sensor and/or less corrosion and/or improved biocompatibility profiles. Related embodiments of the invention include methods for inhibiting corrosion of a sensor element and/or method for improving the biocompatibility of a sensor embodiments of the invention (e.g. one constructed to use such materials).

In some embodiments of the invention, at least one electrode is formed from a flexible electrically conductive wire. Optionally, the flexible electrically conductive wire is disposed in the apparatus in a coiled configuration. In addition, electrodes in various embodiments of the invention can be coated with a variety of materials (e.g. an analyte modulating layer) in order to influence the function of the sensor apparatus. In some embodiments of the invention, the analyte modulating layer is coated over at least 50, 75% or 100% of the reactive surface of an electrode (e.g. an electrically conductive wire). Embodiments of the invention can include a coating of a Prussian blue composition on an electrode at a location and in an amount sufficient to mediate an electrical potential of an electrode of the apparatus. Related embodiments of the invention include methods for mediating an electrical potential of an electrode of the disclosed sensor apparatus (e.g. by using a Prussian blue composition).

In certain embodiments of the invention, the analyte sensing layer comprises an oxidoreductase that generates hydrogen peroxide upon exposure to a ligand for the oxidoreductase, wherein the amount of hydrogen peroxide generated by the polypeptide is proportional to the amount of ligand exposed to the polypeptide. Typically, the oxidoreductase polypeptide comprises an enzyme selected from the group consisting of glucose oxidase, glucose dehydrogenase, lactate oxidase, hexokinase and lactose dehydrogenase. Optionally, the analyte sensing layer comprises an oxidoreductase polypeptide crosslinked to a carrier polypeptide by a crosslinking compound having the formula: $L_1$-$CH_2$—($CH_2$—O—$CH_2$)$_n$—$CH_2$-$L_2$, wherein L1 and L2 comprise N-Hydroxysuccinimide (e.g. N-Hydroxysuccinimide moieties that covalently bond to amine moieties on the oxidoreductase polypeptide and the carrier polypeptide) or pentafluorophenyl moieties and n is equal to 5, 6, 7, 8, 9 or 10. In certain embodiments of the invention, the crosslinking compound is bis N-succinimidyl-[pentaethylene glycol]ester comprising polyethylene glycol moieties so as to make the analyte sensing layer with more flexible and hydrophilic than a crosslinking compound that does not contain polyethylene glycol moieties. Related embodiments of the invention include methods for using such a crosslinking compound to inhibit sensor layer cracking and/or delamination and/or to facilitate the hydration of sensor electrodes and/or to facilitate or control the stoichiometry of a chemical reaction of the various sensor embodiments of the invention.

In some embodiments of the invention, the architecture or thickness of a layer is used to optimize a property of the sensor. For example in some embodiments of the invention, the elongated base layer is comprised of a dielectric polyimide or ceramic material that is at least 100 microns thick. In some embodiments of the invention, the analyte modulating layer is at least 6, 7, 8, 9, 10 or 11 microns thick. Typical embodiments of the invention comprise further layers such as an adhesion promoting layer disposed between the analyte sensing layer and the analyte modulating layer. Optionally in such embodiments, a first compound in the adhesion promoting layer is crosslinked to a second compound in the analyte sensing layer. Certain embodiments of the invention include an interference rejection layer, for example one comprised of a cellulose acetate and/or NAFION composition. Related embodiments of the invention include methods for inhibiting one or more signals generated by an interfering compound in various sensor embodiments of the invention (e.g. by using an interference rejection layer).

In typical embodiments of the invention, the sensor is operatively coupled to further elements (e.g. electronic components) such as elements designed to transmit and/or receive a signal, monitors, processors and the like as well as devices that can use sensor data to modulate a patient's physiology such as medication infusion pumps. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase and at least one working electrode is not coated with an analyte sensing layer comprising glucose oxidase.

In some embodiments of the invention, a processor is capable of comparing a first signal received from a working electrode in response to a first working potential with a second signal received from a working electrode in response to a second working potential, wherein the comparison of the first and second signals at the first and second working potentials can be used to identify a signal generated by an interfering compound. In one such embodiment of the invention, one working electrode is coated with glucose oxidase and another is not, and the interfering compound is acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides or uric acid. Optionally, a pulsed and/or varied voltage is used to obtain a signal from a working electrode. Typically, at least one working potential is 280, 535 or 635 millivolts. Related embodiments of the invention include methods for identifying and/or characterizing one or more signals generated by an interfering compound in various sensor embodiments of the invention (e.g. by comparing the signal from an electrode coated with an analyte sensing compound with a comparative electrode not coated with an analyte sensing compound). Optionally, such methods use a pulsed and/or varied working potential to observe a signal at an electrode.

In one embodiment of the invention, a processor compares a first signal received from a working electrode coated with glucose oxidase in response to a first working potential with a second signal received from a working electrode coated with glucose oxidase in response to a second working potential, wherein the comparison of the first and second signals at the first and second working potentials is used to characterize a blood glucose concentration within at least one discreet concentration range. In some embodiments of the invention, the comparison of the first and second signals at the first and second working potentials can be used to characterize a blood glucose concentration within a concentration range below 70 mg/dL or above 125 mg/dL. Related embodiments of the invention include methods for identifying and/or characterizing a specific analyte concentration or range of analyte concentrations using the various sensor embodiments of the invention (e.g. by comparing the analyte signal from one or more electrodes at different working potentials, wherein the different working potentials are selected for their ability to characterize a specific analyte concentration and/or range of analyte concentrations).

In another illustrative embodiment of the invention, the processor is capable of characterizing a plurality of signals received from the sensor by for example comparing a first signal received from a working electrode coated with glucose oxidase with a second signal received from a working electrode not coated with glucose oxidase so as to obtain information on a background signal that is not based on a sensed physiological characteristic value in the mammal. In another illustrative embodiment of the invention, the processor is capable of characterizing a plurality of signals received from the sensor by comparing a first signal received from a working electrode coated with glucose oxidase with a second signal received from a working electrode not coated with glucose oxidase so as to obtain information on a signal generated by an interfering compound. In another embodiment of the invention, two working electrodes are coated with glucose oxidase and the processor is capable of obtaining information on glucose concentrations in the mammal by comparing the signals received from the two working electrodes coated with glucose oxidase.

Embodiments of the invention include the use of voltage switching not only in the detection of interfering species and/or specific analyte concentrations but also to facilitate the hydration and/or initialization of various sensor embodiments of the invention. In particular, the time for initialization ("run in") differs for different sensors and can take hours. Embodiments of the invention include a sensor initialization scheme involving high frequency initialization (e.g. switching of voltage potentials). In one illustrative embodiment, a triple initialization profile is used where the voltage of the sensor is switched between a first potential such as 280, 535 or 635 millivolts and a second potential such as 1.070 millivolts over a period of 1, 5, 10 or 15 minutes. Certain voltage switching embodiments of the invention further incorporate voltage pulsing in the measurement of an analyte. The number of pulses used in such embodiments of the invention is typically at least 2 and can be 3, 4, 5, 6, 7, 8, 9, 10, 15, 20 or more. Pulses can be for a predetermined period of time, for example 1, 3, 5, 7, 10, 15, 30, 45, 60, 90 or 120 seconds. One illustrative example of this comprises 6 pulses, each 1, 2, 3, 4, 5 or 6 seconds long. By using such embodiments of the invention, the sensor run-in is greatly accelerated, a factor which optimizes a user's introduction and activation of the sensor.

Embodiments of the invention include specific sensor structures as well as methods for facilitating the hydration and/or initialization of a sensor by using the sensor embodiments disclosed herein. Sensors using such initialization schemes can have both software and hardware tailored for this process. Typically the software includes algorithms that control for example: (1) voltage output; (2) pulsing and/or switching times. In this context, the pulse can be controlled so be in many forms including for example traditional square wave/step and/or sign wave and/or ramped wave forms and/or staircase etc. Moreover, as different sensor embodiments can be designed for use in different tissues (e.g. fat or muscle), specific initialization schemes can be tailored to the characteristics of the tissue in which the sensor is implanted.

Some embodiments of the invention can use feedback from sensor signals to provide information to a user as to start up status and/or instructions as to when to start sensing. For example, in the embodiments disclosed herein, one can use the value of an open circuit potential as a way to measure if a sensor is completely hydrated. In particular, mechanistically, in any potentiostat, one observes the difference between a working electrode and a reference electrode. This potential changes depending upon the hydration of the sensor. In the sensor is not hydrated, the circuit potential is very high (e.g. 400-500 millivolts). This circuit potential then changes as the sensor becomes hydrated. One illustrative embodiment of the invention comprises a method of detecting whether a sensor is sufficiently hydrated for analyte detection, comprising calculating an open circuit potential value (e.g. an impedance value) between at least two electrodes of the sensor; and comparing the impedance value against a threshold to determine if the sensor sufficiently hydrated for analyte detection. A related embodiment of the invention is a sensor having the hardware and/or software designed to perform such methods. Yet another embodiment of the invention is an analyte sensor apparatus that includes a processor that detects whether a sensor is sufficiently hydrated for analyte detection comprising calculating an impedance value; and comparing the impedance value against a threshold to determine if the sensor is sufficiently hydrated for analyte detection. Certain embodiments of the invention are designed include an alarm signal (e.g. a indicator light, a bell, whistle or the like) that is triggered when the sensor registers an impedance value indicating that it sufficiently hydrated for analyte detection (and in this way informs a user of the status of the sensor). A related embodiment of the invention is a method of detecting whether a sensor is sufficiently hydrated for analyte detection, comprising calculating an open circuit potential value between at least two electrodes of the sensor; and comparing the open circuit potential value against a threshold to determine if the sensor sufficiently hydrated for analyte detection. In one illustrative embodiment for example, a user can be instructed to typically wait a specific period of time (e.g. 30 minutes), with however, the sensor providing a signal to start earlier if signals sensed are indicative of sufficient hydration.

Some embodiments of the invention include a fuse element that can be triggered after a predetermined period of time or event so as to interrupt a flow of electrical current within the apparatus (i.e. so as to disable the sensor). For example, one embodiment of the invention includes a sensor operatively coupled to a sensor input capable of receiving a signal from the sensor that is based on a sensed physiological characteristic value in the mammal; and a processor coupled to the sensor input, wherein the processor is capable of triggering a fuse element to disable the sensor after a predetermined period which is based upon the in vivo lifetime of the sensor. In a related embodiments of the invention, the processor is capable of triggering a fuse element upon receipt of a signal that is outside of a predetermined set of signal parameters that are associated with normal sensor function. In one such embodiment of the invention, parameters that are outside of those associated with normal sensor function includes a current that is above a prescribed maximum or is below a prescribed minimum for more than a prescribed time. Related embodiments of the invention include methods for disabling a sensor embodiments of the invention (e.g. by using a fuse element), for example a sensor which has exceeded a predetermined period of operation (e.g. lifespan) and/or a sensor that is not performing within a predetermined set of operating parameters.

In addition, in certain sensor embodiments that switch between a high potential to a low potential (e.g. with a frequency of less than 3 seconds), a sensor embodiment may not have sufficient time for an electrical discharge, with for example sensor elements acting together as a sort of capacitor. In this context, some embodiments of the invention can include one or more elements that facilitates sensor circuit discharge (e.g. if discharge is not sufficient to reach a specific potential such as 535 millivolts). Optionally for example, a sensor charge can be removed by connecting it through a discharging switch element, and/or a discharging resistor element.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

In FIG. 4B, the pulsed readings initially have ISgig(nA) readings lower than the non-pulsed readings which then shift to higher relative readings as indicated by the circled portion of the graph. The data provided in these graphs show that pulsed sensors have a two-piece linearity. For example, the slope of the current versus time plot is much steeper at lower concentrations.

DETAILED DESCRIPTION OF THE EMBODIMENTS

Figure 1:
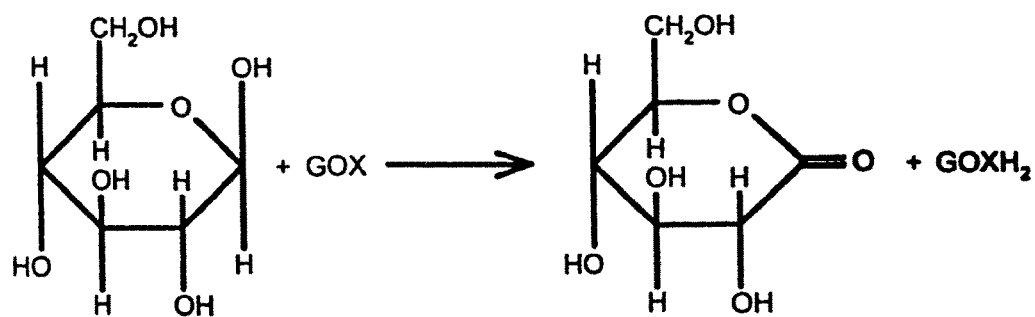
FIG. 1 provides a schematic of the well known reaction between glucose and glucose oxidase. As shown in a stepwise manner, this reaction involves glucose oxidase ($GO_x$), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).
Figure 1:
Figure 1:
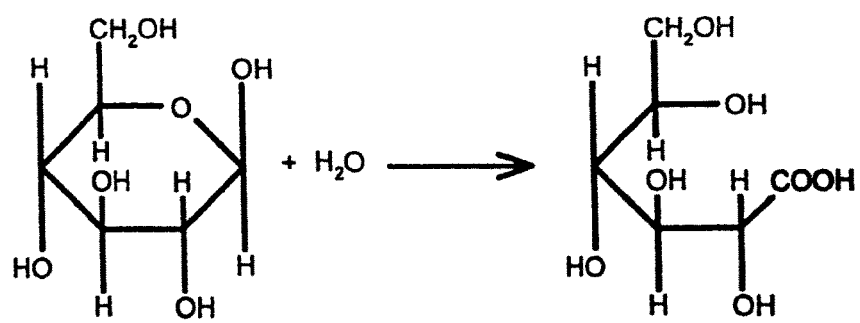

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Before the present compositions and methods etc. are described, it is to be understood that this invention is not limited to the particular methodology, protocol and reagent described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The terms "electrochemically reactive surface" and "electroactive surface" as used herein are broad terms and are used in their ordinary sense, including, without limitation, the surface of an electrode where an electrochemical reaction takes place. In one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. In an illustrative embodiment, the sensing region can comprise a non-conductive body, a working electrode, a reference electrode, and a counter electrode passing through and secured within the body forming electrochemically reactive surfaces on the body and an electronic connective means at another location on the body, and a one or more layers covering the electrochemically reactive surface.

The terms "electrical potential" and "potential" as used herein, are broad terms and are used in their ordinary sense, including, without limitation, the electrical potential difference between two points in a circuit which is the cause of the flow of a current. The term "system noise," as used herein, is a broad term and is used in its ordinary sense, including, without limitation, unwanted electronic or diffusion-related noise which can include Gaussian, motion-related, flicker, kinetic, or other white noise, for example.

The terms "interferents" and "interfering species," as used herein, are broad terms and are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte. In some embodiments, the sensor can use an amperometric, coulometric, conductimetric, and/or potentiometric technique for measuring the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. electrodes and electrode designs) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

In typical embodiments of the present invention, the transduction of the analyte concentration into a processable signal is by electrochemical means. These transducers may include any of a wide variety of amperometric, potentiometric, or conductimetric base sensors known in the art. Moreover, the microfabrication sensor techniques and materials of the instant invention may be applied to other types of transducers (e.g., acoustic wave sensing devices, thermistors, gas-sensing electrodes, field-effect transistors, optical and evanescent field wave guides, and the like) fabricated in a substantially nonplanar, or alternatively, a substantially planar manner. A useful discussion and tabulation of transducers which may be exploited in a biosensor as well as the kinds of analytical applications in which each type of transducer or biosensor, in general, may be utilized, is found in an article by Christopher R. Lowe in Trends in Biotech. 1984, 2(3), 59-65.

Specific aspects of embodiments of the invention are discussed in detail in the following sections.

I. Typical Elements, Configurations and Analyte Sensor Embodiments of the Invention

A. Typical Architectures Found in of Embodiments of the Invention

Figure 2:
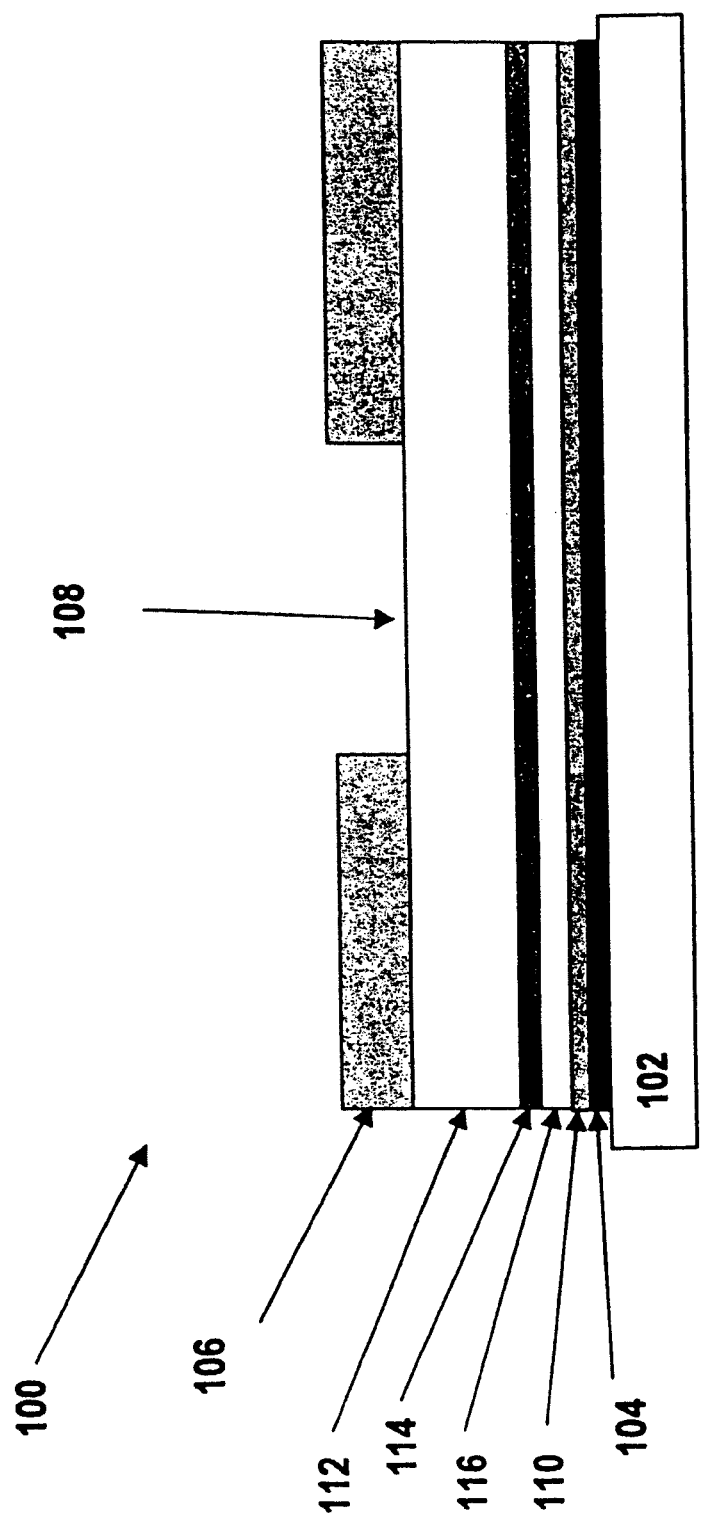
FIG. 2 provides a diagrammatic view of a typical layered analyte sensor configuration of the current invention.

FIG. 2 illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

In certain embodiments of the invention, a sensor is designed to include additional layers such as an interference rejection layer discussed below.

B. Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2, the base constituent 102 comprises a ceramic. Alternatively, the base constituent comprises a polymeric material such as a polyimide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetrafluoroethylenes, the perfluoronated ionomer Nafion™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference.

Analyte Sensing Constituent

The electrochemical sensors of the invention include an analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a $GO_x$ and HSA mixture. In a typical embodiment of an analyte sensing constituent having $GO_x$, the $GO_x$ reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde, including, but not limited to those shown in Table 1. Other suitable cross-linkers also may be used, as will be evident to those skilled in the art.

The $GO_x$ and/or carrier protein concentration may vary for different embodiments of the invention. For example, the $GO_x$ concentration may be within the range of approximately 50 mg/ml (approximately 10,000 U/ml) to approximately 700 mg/ml (approximately 150,000 U/ml). Typically the $GO_x$ concentration is about 115 mg/ml (approximately 22,000 U/ml). In such embodiments, the HSA concentration may vary between about 0.5%-30% (w/v), depending on the $GO_x$ concentration. Typically the HSA concentration is about 1-10% w/v, and most typically is about 5% w/v. In alternative embodiments of the invention, collagen or BSA or other structural proteins used in these contexts can be used instead of or in addition to HSA. Although $GO_x$ is discussed as an illustrative enzyme in the analyte sensing constituent, other proteins and/or enzymes may also be used or may be used in place of $GO_x$, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, could be used instead of or in addition to HSA.

As noted above, in some embodiments of the invention, the analyte sensing constituent includes a composition (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; (Jan. 7, 1991) the entire contents of which are incorporated herein by reference.

Other useful analyte sensing constituents can be formed to include antibodies whose interaction with a target analyte is capable of producing a detectable signal that can be sensed by the electrically conductive elements after interacting with the target analyte whose presence is to be detected. For example U.S. Pat. No. 5,427,912 (which is incorporated herein by reference) describes an antibody-based apparatus for electrochemically determining the concentration of an analyte in a sample. In this device, a mixture is formed which includes the sample to be tested, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme then hydrolyzes the labeled substrate, resulting in the generation of an electroactive label, which can then be oxidized at the surface of an electrode. A current resulting from the oxidation of the electroactive compound can be measured and correlated to the concentration of the analyte in the sample. U.S. Pat. No. 5,149,630 (which is incorporated herein by reference) describes an electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component. U.S. Pat. No. 6,410,251 (which is incorporated herein by reference) describes an apparatus and method for detecting or assaying one constituting member in a specific binding pair; for example, the antigen in an antigen/antibody pair, by utilizing specific binding such as binding between an antigen and an antibody, together with redox reaction for detecting a label, wherein an oxygen micro-electrode with a sensing surface area is used. In addition, U.S. Pat. No. 4,402,819 (which is incorporated herein by reference) describes an antibody-selective potentiometric electrode for the quantitative determination of antibodies (as the analyte) in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis. For related disclosures, see also U.S. Pat. Nos. 6,703,210, 5,981,203, 5,705,399 and 4,894,253, the contents of which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Constituent

The electrochemical sensors of the invention optionally include a protein constituent disposed between the analyte sensing constituent and the analyte modulating constituent (see, e.g. element 116 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase ($GO_X$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

Cover Constituent

The electrochemical sensors of the invention include one or more cover constituents which are typically electrically insulating protective constituents (see, e.g. element 106 in FIG. 2). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photoimageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values includes a plurality of measurements of blood glucose.

Figure 3:
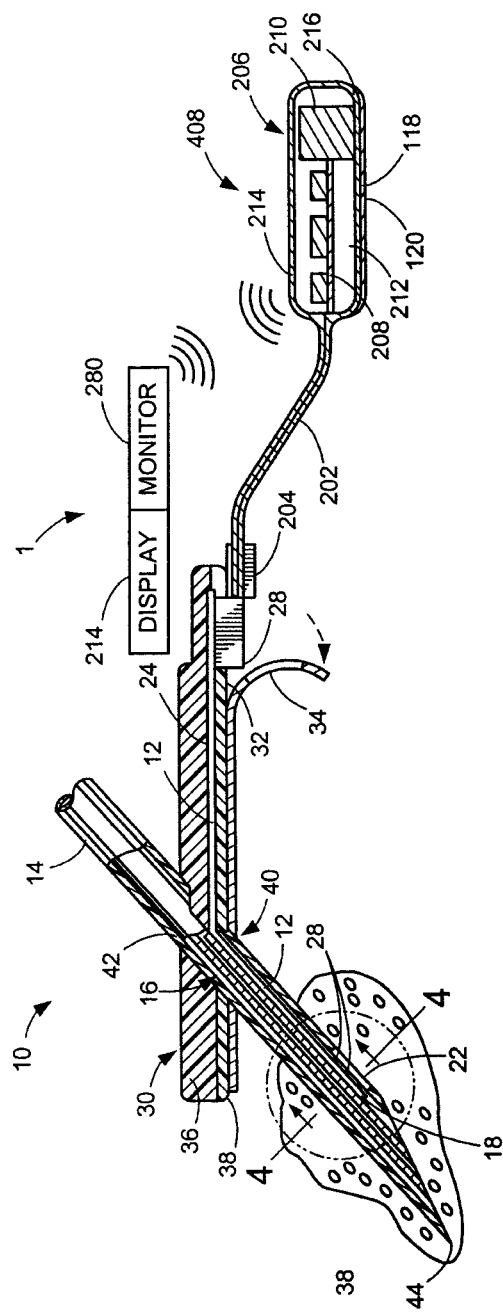
FIG. 3 provides a perspective view illustrating a subcutaneous sensor insertion set, a telemetered characteristic monitor transmitter device, and a data receiving device embodying features of the invention.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 314 for monitoring a user's condition in response to signals derived from the sensor electrodes 20. The connection portion 24 may be conveniently connected electrically to the monitor 200 or a characteristic monitor transmitter 400 by a connector block 28 (or the like) as shown and described in U.S. Pat. No. 5,482,473, entitled FLEX CIRCUIT CONNECTOR, which is incorporated by reference.

As shown in FIG. 3, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and further through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 400 is coupled to a sensor set 10 by a cable 202 through a connector 204 that is electrically coupled to the connector block 28 of the connector portion 24 of the sensor set 10.

In the embodiment shown in FIG. 3, the telemetered characteristic monitor 400 includes a housing 206 that supports a printed circuit board 208, batteries 210, antenna 212, and the cable 202 with the connector 204. In some embodiments, the housing 206 is formed from an upper case 214 and a lower case 216 that are sealed with an ultrasonic weld to form a waterproof (or resistant) seal to permit cleaning by immersion (or swabbing) with water, cleaners, alcohol or the like. In some embodiments, the upper and lower case 214 and 216 are formed from a medical grade plastic. However, in alternative embodiments, the upper case 214 and lower case 216 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 216 may have an underside surface coated with a suitable pressure sensitive adhesive layer 118, with a peel-off paper strip 120 normally provided to cover and protect the adhesive layer 118, until the sensor set telemetered characteristic monitor transmitter 400 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. No. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 202 through a connector that is electrically coupled to the connector block 28 of the connection portion 24. In an alternative embodiment, the cable may be omitted. In this embodiment of the invention, the monitor 200 may include an appropriate connector for direct connection to the connection portion 204 of the sensor set 10. The sensor set 10 may be modified to have the connector portion 204 positioned at a different location, e.g., on top of the sensor set to facilitate placement of the monitor 200 over the sensor set.

D. Embodiments of the Invention and Associated Characteristics

Embodiments of the invention disclosed herein focus on implantable analyte sensors and sensor systems that are designed to include elements and/or configurations of elements that facilitate sensor initialization and/or start-up in vivo (e.g. the run-in time that it takes for a sensor to settle into its environment and start transmitting meaningful information after being implanted in vivo). In particular, it is known in the art that the amount time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin). In addition, a relatively long sensor initialization and/or start-up period in hospital settings can require repeated monitoring by hospital staff, a factor which contributes to the costs of patient care. For these reasons, sensors having reduced initialization and/or start-up times in vivo in hospital settings and sensors and sensor systems that are designed to include elements and/or configurations of elements that diminish long sensor initialization and/or start-up times are highly desirable. With glucose sensors for example, a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. The use of glucose sensors, insulin infusion pumps and the like in the management of diabetes has increased in recent years due for example to studies showing that the morbidity and mortality issues associated with this chronic disease decrease dramatically when a patient administers insulin in a manner that closely matches the rise and fall of physiological insulin concentrations in healthy individuals. Consequently, patients who suffer from chronic diseases such as diabetes are instructed by medical personnel to play an active role in the management of their disease, in particular, the close monitoring and modulation of blood glucose levels. In this context, because many diabetics do not have medical training, they may forgo optimal monitoring and modulation of blood glucose levels due to complexities associated with such management, for example, a two hour start-up period which can be an inconvenience in view of a patient's active daily routine. For these reasons, sensors and sensor systems that are designed to include elements and/or configurations of elements can reduce sensor initialization and/or start-up times in are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

Embodiments of the invention disclosed include those having at least one element within a constellation of elements that have identified as functioning to reduce sensor start-up initialization times. In addition, as disclosed herein, certain embodiments of the invention include those having at least two distinct elements disclosed herein that are within constellation of elements that Applicants have identified as reducing sensor start-up initialization times in a complementary manner. Specifically, not all sensor materials, elements, architectures and/or electronics known in the art can be combined together in a manner that functions to reduce sensor start-up initialization times. Consequently, the disclosure provided herein focuses on those sensor materials, elements, architectures and/or electronics that we have discovered can be combined together to reduce sensor start-up initialization times without antagonizing and/or inhibiting the specific functions of the individual elements.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

The invention disclosed herein has a number of embodiments. One illustrative embodiment of the invention is an analyte sensor apparatus comprising: an elongated (i.e. having notably more length than width) base layer; a conductive layer disposed on the base layer and comprising a reference electrode, a working electrode and a counter electrode; an analyte sensing layer disposed on the conductive layer; an analyte modulating layer disposed on the analyte sensing layer, wherein the analyte modulating layer comprises a composition that modulates the diffusion of an analyte diffusing through the analyte modulating layer; and a cover layer disposed on the analyte sensor apparatus, wherein the cover layer comprises an aperture positioned on the cover layer so as to facilitate an analyte contacting and diffusing through the analyte modulating layer and contacting the analyte sensing layer. Typical embodiments of the invention are comprised of biocompatible materials and/or have structural features designed for implantation within a mammal. Methodological embodiments of the invention include methods for making and using the sensor embodiments disclosed herein. Certain embodiments of the invention include methods of using a specific sensor element and/or a specific constellation of sensor elements to produce and/or facilitate one or more functions of the sensor embodiments disclosed herein.

As disclosed herein, those of skill in the art understand that a conductive layer disposed on the base layer and comprising a working electrode, a counter electrode and a reference electrode includes embodiments wherein the conductive layer is disposed on at least a portion the base layer and does not necessarily completely cover the base layer. Those of skill in the art will understand that this refers to other layers within the sensor, with for example, an analyte sensing layer disposed on the conductive layer encompassing sensor embodiments where the analyte sensing layer disposed on at least a portion of the conductive layer; and an analyte modulating layer disposed on the analyte sensing encompassing an analyte modulating layer disposed on at least a portion of the analyte sensing etc. etc. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1× reference electrode, a 2.6× working electrode and a 3.6× counter electrode.

In certain embodiments of the invention, an element of the apparatus such as an electrode or an aperture is designed to have a specific configuration and/or is made from a specific material and/or is positioned relative to the other elements so as to facilitate a function of the sensor. For example, without being bound by a specific theory or mechanism of action, it appears that sensor embodiments (e.g. simple three electrode embodiments) may be more susceptible to local environment changes around a single electrode. For example, a gas bubble on top of or close to a reference or another electrode, and/or a stagnating or semi-stagnating pool of fluid on top of or close to a reference or another electrode may consequently compromises sensor performance. In this context, a distributed electrode configuration appears be advantageous because the distribution of the electrode area allows the sensor to compensate for signal lost to a small local area (e.g. as can occur due to lack of hydration, fluid stagnation, a patient's immune response, or the like).

In certain embodiments of the invention, distributed electrode configurations are used in methods designed to overcome problems with sensors and sensor systems that occur due to lack of hydration (e.g. slow start-up initialization times), fluid stagnation, a patient's immune response, or the like. For example, as shown in FIGS. 6B-6F, sensor embodiments having a plurality of electrodes disposed on a substrate in a distributed electrode configurations are observed to exhibit a better start-up profile than sensors having a single set of electrodes disposed on a substrate in a longitudinal row. In addition, embodiments of the invention having distributed electrode configurations can be combined with certain complementary elements disclosed herein so as to further overcome problems that result from a lack of hydration, fluid stagnation, a patient's immune response, or the like (e.g. multiple electrode sensors, voltage pulsing methods etc.).

Another embodiment of the invention also designed to address the lack-of-electrode hydration and/or fluid stagnation etc. is a sensor configured to facilitate in vivo fluid flow to the electrode, for example by removing tubing and/or cover elements that surrounding the sensor, which, as shown herein, optimizes sensor initialization without compromising long-term function of implantable sensors (e.g. as could result from biofouling of the exposed sensor surfaces). For example in certain sensor embodiments having tubing surrounding the reference electrode, the startup rate without that trimming can be as low as 60%. If, however, the sidewalls of the tubing surrounding the reference electrode are trimmed in such embodiments, 100% of the sensors startup. In such embodiments of the invention, the removal of a sidewall may facilitate hydration, and/or allow closer proximity of tissue and/or reduce the likelihood of fluid stagnation. In this context, embodiments of the invention include those having a constellation of elements arranged in a manner designed not to inhibit (and optional to enhance) flow of a fluid containing an analyte of interest around/through the elements of the sensor embodiment to a reactive surface of an electrode of the sensor embodiment.

In one embodiment of the invention, a working electrode, a counter electrode and a reference electrode are positionally distributed on the base and/or the conductive layer in a configuration that facilitates hydration of the working electrode, the counter electrode or the reference electrode when the sensor apparatus is placed in contact with a fluid comprising the analyte (e.g. by inhibiting shadowing of the reference electrode, a phenomena which can inhibit hydration and capacitive start-up of a circuit). Optionally, for example the sensor includes a distributed electrode configuration and/or an aperture configuration that inhibits the occurrence of localized and detrimental environment changes around a single electrode (e.g. inactivation of some portion of the electrode function due to bubble formation, and/or an in vivo response such as biofouling and/or an immune response). Typically such embodiments of the invention facilitate sensor start-up or initialization. Illustrative embodiments of such electrode configurations are shown in FIGS. 6A-6F.

In some sensor embodiments, the distributed electrodes are organized/disposed within a flex-circuit assembly (i.e. a circuitry assembly that utilizes flexible rather than rigid materials). Such flex-circuit assembly embodiments provide an interconnected assembly of elements (e.g. electrodes, electrical conduits, contact pads and the like) configured to facilitate wearer comfort (for example by reducing pad stiffness and wearer discomfort) as well as parameter measurement performance. FIGS. 13A-13D show sensor flex layouts that can be used in embodiments of the invention in order to optimize the dual sensor layout and connection scheme. The embodiment shown in FIG. 13A has 2 columns of contact pads on the left with the electrodes on the right. The close proximity of the pads in this design allows for ease of connection to cable as well as a compact design. The embodiment shown in FIG. 13B has the 2 columns of contact pads at the center in between both sensor electrodes. Embodiments having the electrodes on the opposite side maximizes sensor separation while keeping both contact pads together. The embodiment shown in FIG. 13C has a single column of contact pads allowing for a different connection scheme with more width space than the design shown in FIG. 13A. The embodiment shown in FIG. 13D benefits from a staggered element layout which allowing it to be compact yet still retain spacing between electrodes sets. Certain flex assemblies than can be modified and or adapted for use with embodiments of the invention are disclosed for example in U.S. Pat. Nos. 7,340,287, 7,377, 794 and 6,930,494 the contents of which are incorporated by reference.

In certain embodiments of the invention, sensor systems that comprise flex assemblies are used in methods designed to overcome problems that can occur with implantable sensors and sensor systems due to lack of hydration (e.g. slow start-up initialization times) and/or fluid stagnation by enhancing the flexing and movement of the implanted components in a manner that enhances fluid flow around these components and inhibits the likelihood of a gas bubble and/or a stagnating pool of fluid and/or biofouling macromolecules from forming and/or remaining on top of or close to an electrode in a manner that compromises sensor function. In addition, embodiments of the invention that comprise flex assemblies can be combined with certain complementary elements disclosed herein so as to further overcome problems that result from a lack of hydration, gas bubble formation, fluid stagnation, biofouling, a patient's immune response, or the like (e.g. distributed electrode configurations, multiple electrode sensors, multiple sensor apparatuses having multiple implantation sites, voltage pulsing methods etc.).

Typical analyte sensor apparatus embodiments comprises a plurality of working electrodes, counter electrodes and reference electrodes. Optionally, the plurality of working, counter and reference electrodes are grouped together as a unit and positionally distributed on the conductive layer in a repeating pattern of units. Alternatively, the plurality of working, counter and reference electrodes are grouped together and positionally distributed on the conductive layer in a non-repeating pattern of units. In certain embodiments of the invention, the elongated base layer is made from a material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to maintain an optimal function if a portion of the sensor having one or more electrodes is dislodged from an in vivo environment and exposed to an ex vivo environment.

In one embodiment of the sensor having a distributed electrode configuration designed to facilitate hydration, the working electrode, the counter electrode and the reference electrode are positionally distributed on conductive layer in a configuration arranged so that a first electrode is disposed in a region on a first edge of the elongated base layer; a second electrode is disposed in a region on an opposite edge of the elongated base layer; and a third is disposed in a region of the elongated base layer that between the first electrode and the second electrode. Optionally, the working electrode, the counter electrode and the reference electrode are positionally distributed on conductive layer in a configuration arranged so that the working electrode is disposed in a region on a first edge of the elongated base layer; the counter electrode is disposed in a region on an opposite edge of the elongated base layer; and the reference electrode is disposed in a region of the elongated base layer that between the working electrode and the counter electrode. In some embodiments of the invention, the reference electrode is at the proximal end of an implanted sensor (i.e. closest to the skin surface). In other embodiments, the reference electrode is at the distal end of an implanted sensor.

Typically, the electrodes in a sensor are of a rectangular shape, i.e. have a longer side and a shorter side (including those of a rectangular shape, yet having rounded edges). In some embodiments of the invention, the electrode configuration is such that a longer side of at least one of the electrodes in a distributed electrode pattern is parallel to an longer side of at least one of the other electrodes in the distributed electrode pattern (and optionally all of the electrodes in the distributed electrode pattern). As shown in FIGS. 6B-6F, sensor embodiments having such configurations are observed to exhibit a better start-up profile than sensors without electrodes configured in this pattern. In certain embodiments of the invention, an edge or center of a side of a reference electrode is lined up with an edge or center of a side the working or counter electrode. Typically in these embodiments the sides are the longer sides of a rectangular electrode. In some embodiments of the invention, an edge or center of a side of a reference electrode is offset about 25 or 50% with an edge or center of a side of a working or counter electrode. In some embodiments of the invention, the reference electrode is formed in the sensor so as to have a side wall architecture that does not inhibit fluid flow (or no side-walls) so as to improve hydration of the sensor upon contact with a fluid sample. Related embodiments of the invention include methods for using a distributed electrode configuration to facilitate the hydration and/or initialization of various sensor embodiments of the invention.

Figure 7A:
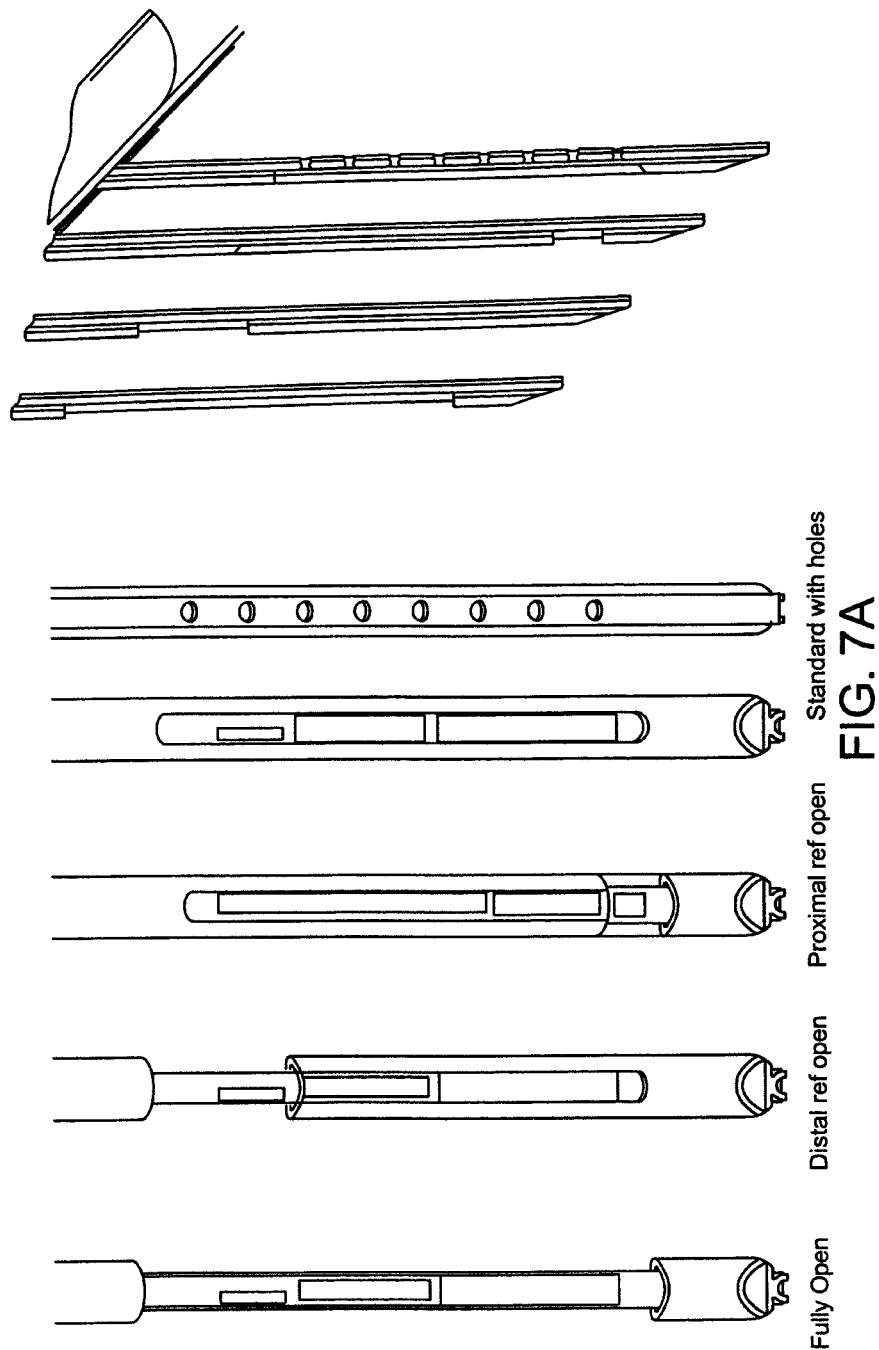
FIG. 7A provides a diagram of different tubing aperture configurations in various sensor embodiments.
Figure 7B:
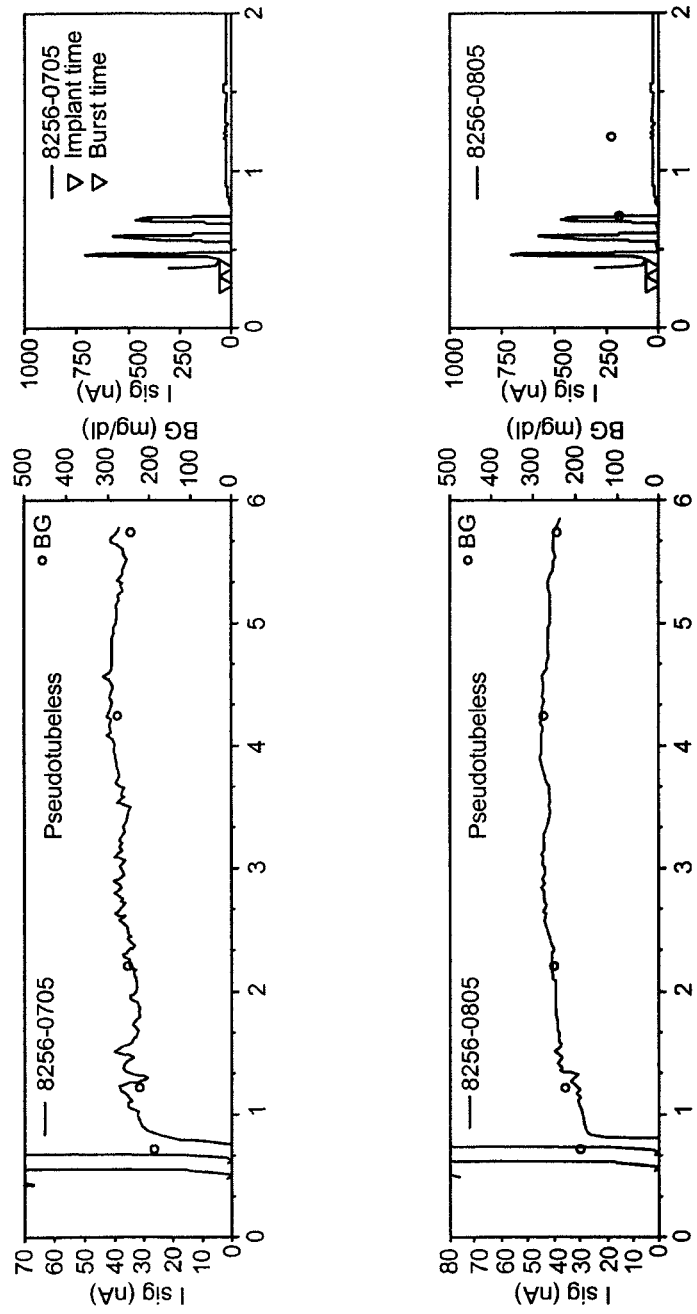
FIGS. 7B-7D provide a diagram of a open window embodiment and associated test data on the impact of this embodiment on sensor start-up.
Figure 7C:
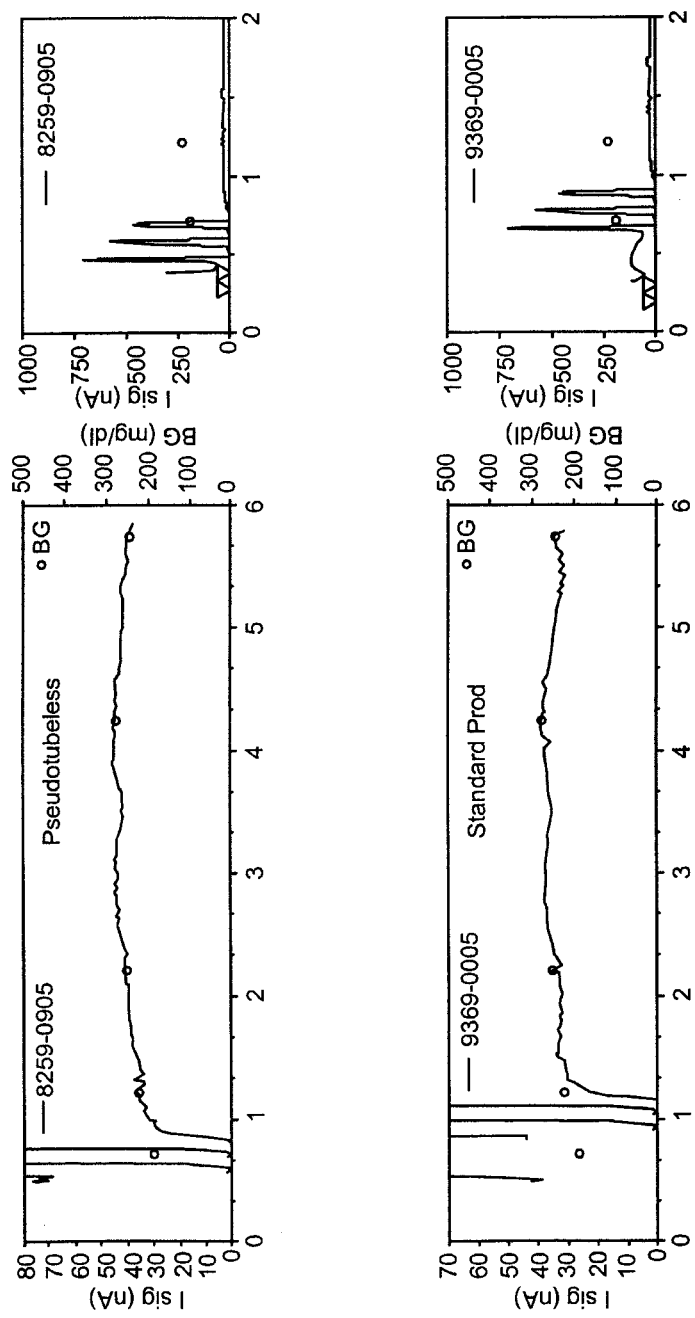
Figure 7D:
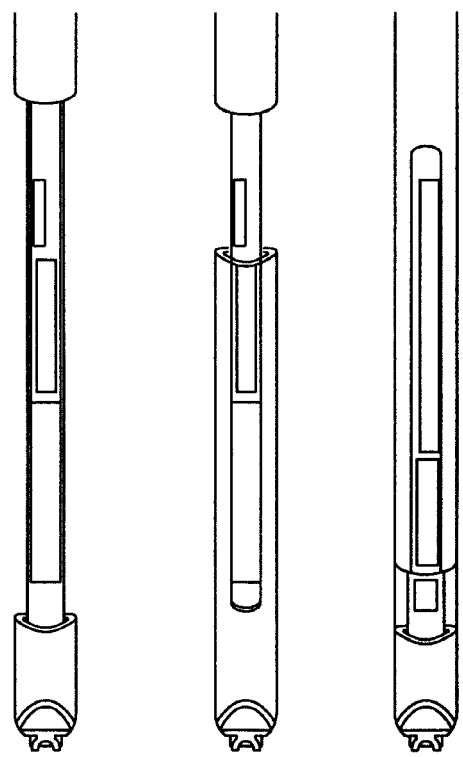

In some embodiments of the invention, an aperture is positioned on the cover layer so that a fluid comprising the analyte contacts the reference electrode, the working electrode and the counter electrode in a sequential manner so as to facilitate sensor hydration and/or sensor start-up or initialization. Illustrative embodiments of such aperture configurations are shown in FIG. 7. In some embodiments of the invention, the aperture is fully open, i.e. opens the electrodes to the external environment by having aperture edges that line up with or are below the electrodes in the sensor (see, e.g. FIGS. 7B-7D). As shown in FIGS. 7B-7D sensors having such fully open apertures to exhibit an optimized profile.

Optionally, the sensor is implanted and an aperture is positioned on the cover layer of the sensor such that the in vivo environment is proximal to the reference electrode so that a fluid comprising the analyte contacts the reference electrode first. In other embodiments of the invention, the aperture is positioned on the cover layer directly over the reference electrode, the working electrode and the counter electrode so that the hydration of these electrode proceeds simultaneously. In related embodiments of the invention, a reference electrode on a distal end of a sensor base is proximal to an aperture; or where a reference electrode on a proximal end of a sensor base is proximal to an aperture. In this context, a cover layer can be constructed from a variety of materials know in the art and can include a variety of apertures having similar or dissimilar sizes, shapes and configurations. In some embodiments of the invention, the cover layer comprises a plurality of apertures (e.g. disposed in a row over the various sensor electrodes) and is formed from a sheath or tube made for example from a biocompatible polymeric material.

Related embodiments of the invention include methods for using a material at the aperture that is designed to facilitate the hydration and/or initialization of various sensor embodiments of the invention. For example, in certain embodiments of the invention, a portion of the sensor apparatus such as one or more apertures is coated and/or filled with a hydrophilic composition (e.g. a hydrophilic polymer) so as to facilitate fluid flow through the one or more apertures. Optionally, the hydrophilic composition further comprises a bioactive agent such as an anti-thrombocytic, anti-inflammatory or anti-proliferative agent (see, e.g. U.S. Pat. No. 6,770,729, the contents of which are incorporated by reference). Because the in vivo thrombocytic, inflammatory and/or proliferative response can deposit cells and other biological materials on or near the sensor that can decrease fluid flow to the sensor, hydrophilic polymers containing these bioactive agents can be used in methods designed to facilitate the hydration and/or initialization of various sensor embodiments of the invention. In certain embodiments of the invention, the bioactive agent can elute from the sensor and migrate into the in vivo environment (e.g. anti-inflammatory agents such as dexamethasone). In other embodiments of the invention, the bioactive agent does not elute from the sensor (e.g. agents such as metallic silver, inorganic silver compounds, silver salts of organic acids, or the like).

In certain embodiments of the invention, sensor systems that comprise an aperture configuration disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that specific aperture configurations can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, voltage pulsing methods etc.).

Figure 9:
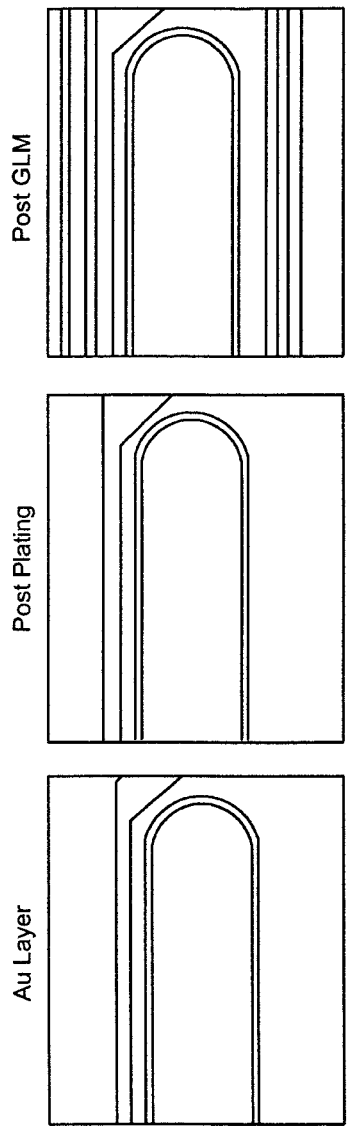
FIG. 9 provide photographs of rounded electrode embodiments of the invention that exhibit for example, a more confined edge structure, a uniform edge bead and a decreased propensity to exhibit delamination of a layer.

Various elements of the sensor apparatus can be disposed at a certain location in the apparatus and/or configured in a certain shape and/or be constructed from a specific material so as to facilitate strength, hydration and/or function of the sensor. One such embodiment of the invention includes an elongated base comprised of a polyimide or dielectric ceramic material that facilitates the strength and durability of the sensor. In certain embodiments of the invention, the structural features and/or relative position of the working and/or counter and/or reference electrodes is designed to influence sensor manufacture, use and/or function. One such embodiment of the invention includes electrodes having one or more rounded edges so as to inhibit delamination of a layer disposed on the electrode (e.g. an analyte sensing layer comprising glucose oxidase). Illustrative embodiments of such rounded electrodes are shown in FIG. 9. Related embodiments of the invention include methods for inhibiting delamination of a sensor layer using a sensor embodiments of the invention (e.g. one having one or more electrodes having one or more rounded edges).

Figure 8A:
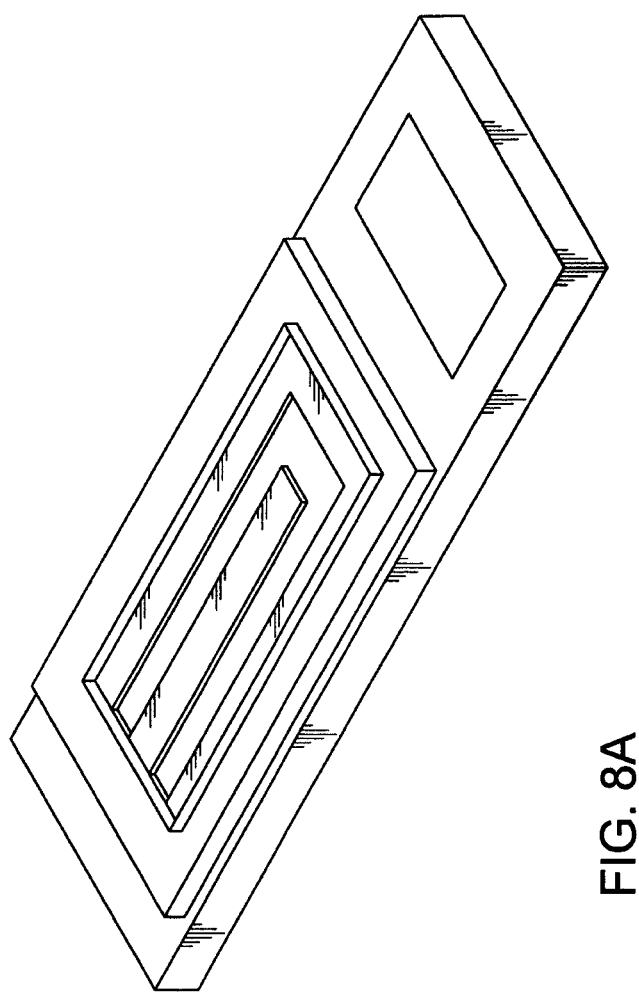
FIGS. 8A and 8B provide diagrams of embodiments sensor barrier structures of the invention. The embodiment shown in FIG. 8B shows a gold barrier formed as a ring as well as additional sensor elements including an elongated ceramic base and fuse elements.
Figure 8B:
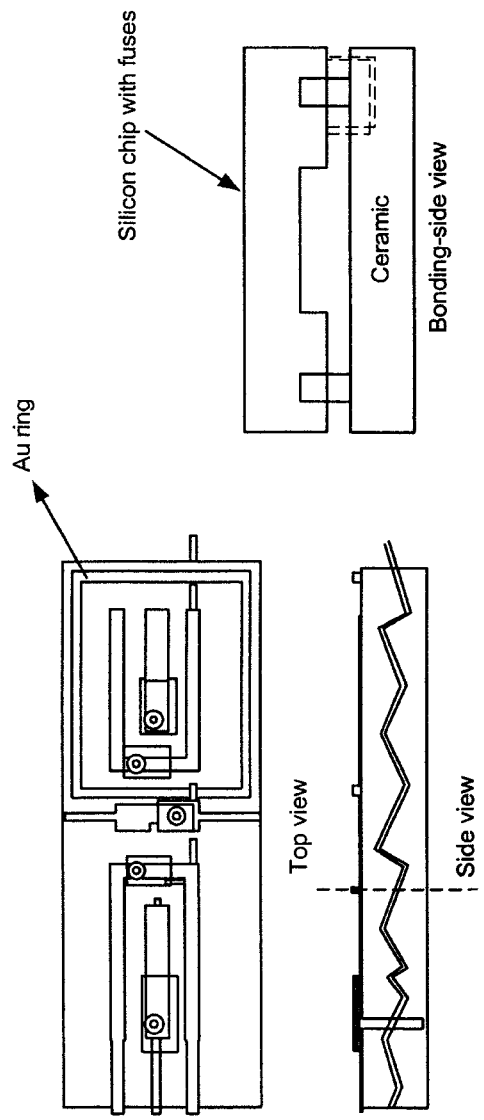

In some embodiments of the invention, a barrier element is disposed on the apparatus so as to inhibit spreading of a layer disposed on an electrode. Illustrative embodiments of such barrier/dam structures are shown in FIG. 8. Optionally, an element such as a metallic or other structure is disposed on top of the dam structure(s). Related embodiments of the invention include methods for inhibiting movement of a compound disposed on a sensor embodiments of the invention (e.g. one constructed to have such a barrier structure). Optionally, a barrier element is disposed on the apparatus so as to encircle a reactive surface of an electrode. Such barrier elements can be made from a variety of materials, for example a polyimide. In various embodiments of the invention, these elements can be formed as part of the electrode or alternatively bonded to the electrode after it is formed (e.g. using an epoxy or the like).

In some embodiments of the invention, at least one electrode is formed from a flexible electrically conductive wire. Optionally, the flexible electrically conductive wire is disposed in the apparatus in a coiled configuration. In certain embodiments, the wire electrode is formed from a platinum, a silver and/or a palladium composition. Optionally, the wire electrode is disposed within a tube cover having at least 5, 10 or 15 apertures positioned so that an analyte of interest can contact the wire electrode. Embodiments of the invention that comprise a wire electrode and/or a distributed electrode pattern such as those disclosed above can be used in methods designed to diminish or overcome problems associated with the shaking and bumping of potentially fragile electronic elements that occurs when an apparatus flexes as it is used in vivo. In particular, an apparatus implanted in vivo is subjected to a variety of mechanical stresses during a patient's daily routine of activities (e.g. stretching, bending, walking and the like). Such stresses are known in the art to have the ability to damage elements within a device, in particular electrodes, which can be brittle and prone to breakage. Embodiments of the invention are designed to overcome problems by using elements (e.g. a flexible wire electrode) and/or architectures (e.g. distributed electrode configurations) that are less likely to lose optimal function as a result of the mechanical stresses that result from a patient's daily routine of activities.

In certain embodiments of the invention, sensor systems that comprise wire electrodes are used in methods designed to overcome problems that can occur with implantable sensors and sensor systems due to lack of hydration (e.g. slow start-up initialization times) and/or fluid stagnation by enhancing the flexing and movement of the implanted components in a manner that enhances fluid flow and inhibit a gas bubble or a stagnating pool of fluid from remaining on top of or close to an electrode in a manner that compromises sensor function. In addition, embodiments of the invention that comprise a wire electrodes can be combined with certain complementary elements disclosed herein so as to further overcome problems that result from a lack of hydration, fluid stagnation, a patient's immune response, or the like (e.g. distributed electrode configurations, flex sensor assemblies, multiple electrode sensors, voltage pulsing methods etc.).

Another embodiment of the invention is a multiconductor sensor comprising a series of electrodes disposed on a base such as a ribbon cable. This configuration is useful in manufacturing/production of the sensor, for example those processes that involve progressive laser ablation. In one such embodiment, a pattern of laser ablation is controlled to produce a single wire with one or more working, counter and reference electrodes and/or a plurality of such electrode groups. Optionally this is in a reel form that is cut into segments prior to sensor manufacture. One illustrative embodiment of this design comprises a wire electrode with multiple reading points (e.g. perforations) along its wire/ribbon body. This wire can further be disposed within sheath or tube having a plurality of windows. Subsequent layers such as the analyte modulating layer can be coated over a portion of or alternatively, the whole wire. Related embodiments of the invention include a method of making such sensors, wherein a step in the method includes disposing the wire electrode in the form of a reel that is then cut into segments during the manufacturing process.

In certain embodiments of the invention, an electrode of the apparatus comprises a platinum composition and the apparatus further comprises a titanium composition disposed between the elongated base layer and the conductive layer. Optionally in such embodiments, apparatus further comprises a gold composition disposed between the titanium composition and the conductive layer. Certain embodiments form one or more of these layers via a process that includes photolithography. Such embodiments of the invention typically exhibit enhanced bonding between layered materials within the sensor and/or less corrosion and/or improved biocompatibility profiles. Such materials are used for example to make sensors having a reduced corrosion profile, one that allows certain corrosion inhibiting insulating elements to be eliminated from a sensor design. Related embodiments of the invention include methods for inhibiting corrosion of a sensor element and/or method for improving the biocompatibility of a sensor embodiments of the invention (e.g. one constructed to use such materials). For certain methods that can be used to make such embodiments of the invention, see, e.g. U.S. Pat. No. 7,033,336, the contents of which are incorporated by reference.

In addition, electrodes in various embodiments of the invention can be coated with a variety of materials (e.g. an analyte modulating layer) in order to influence the function of the sensor apparatus. In some embodiments of the invention, a hydrophilic analyte modulating layer is coated over at least 50, 75% or 100% of the reactive surface of an electrode (e.g. an electrically conductive wire). For example certain embodiments of the invention disclosed herein (e.g. amperometric glucose sensors) include elements and/or constellations of elements that are designed to overcome what is known as "oxygen deficit problem." This problem relates to the fact in that sensors designed to measure an analyte via the reaction of an analyte and oxygen, the oxygen concentration must be in excess. If the oxygen is not in excess (and is instead the rate limiting reactant), the sensor signal will be proportional to the oxygen concentration and not the analyte which the sensor is designed to measure. Under these conditions, sensors will not function properly. Therefore, there is a need for sensors that include biocompatible membrane with differential oxygen and analyte permeabilities (e.g. glucose limiting membranes) and further having elements that function to enhance sensor initialization start up time and further.

Optionally, embodiments of the invention include a plurality of working electrodes and/or counter electrodes and/or reference electrodes (e.g. to provide redundant sensing capabilities). Such embodiments of the invention can be used in embodiments of the invention that include a processor (e.g. one linked to a program adapted for a signal subtraction/cancellation process) are designed factor out background signals in vivo, for example by comparing signal(s) at $GO_x$ coated working electrode with signal at working electrode not coated with $GO_x$ (e.g. background detection followed by a signal subtraction/cancellation process to arrive at a true signal). Certain of these embodiments of the invention are particularly useful for sensing glucose at the upper and lower ends of the glucose signal curves. Similar embodiments of the invention are used to factor out interference, for example by comparing signal(s) at $GO_x$ coated working electrode with signal at working electrode not coated with $GO_x$. Embodiments of the invention can include a coating of a Prussian blue composition on an electrode at a location and in an amount sufficient to mediate an electrical potential of an electrode of the apparatus. Related embodiments of the invention include methods for mediating an electrical potential of an electrode of the disclosed sensor apparatus (e.g. by using a Prussian blue composition). Prussian Blue formulas are known in the art and include $Fe_4[Fe(CN6)_3 \times H_20]$, CI no. 77510 and $KFe[Fe(Cn)_6] \times H_20$ id CI no. 77520.

In some embodiments of the invention, the architecture or thickness of a sensor layer is used to optimize a property of the sensor. For example in some embodiments of the invention, the elongated base layer is comprised of a dielectric or polyimide ceramic material that is at least 100 microns thick. In some embodiments of the invention, the analyte modulating layer is at least 6, 7, 8, 9, 10, 15, 20, 25 or 30 microns thick. Certain embodiments of the invention use a thick layer (e.g. 25 or 30 microns) of an analyte modulating layer because in such embodiments, this thick layer is observed to both optimize the linearity of an analyte signal over a range of signals (e.g. glucose concentration). Such thick layers have further properties that are desirable in certain embodiments of the invention, for example a longer analyte modulating layer lifetime (e.g. due to the extra material), a property that makes them particularly suited for certain long term sensor embodiments.

Figure 10:
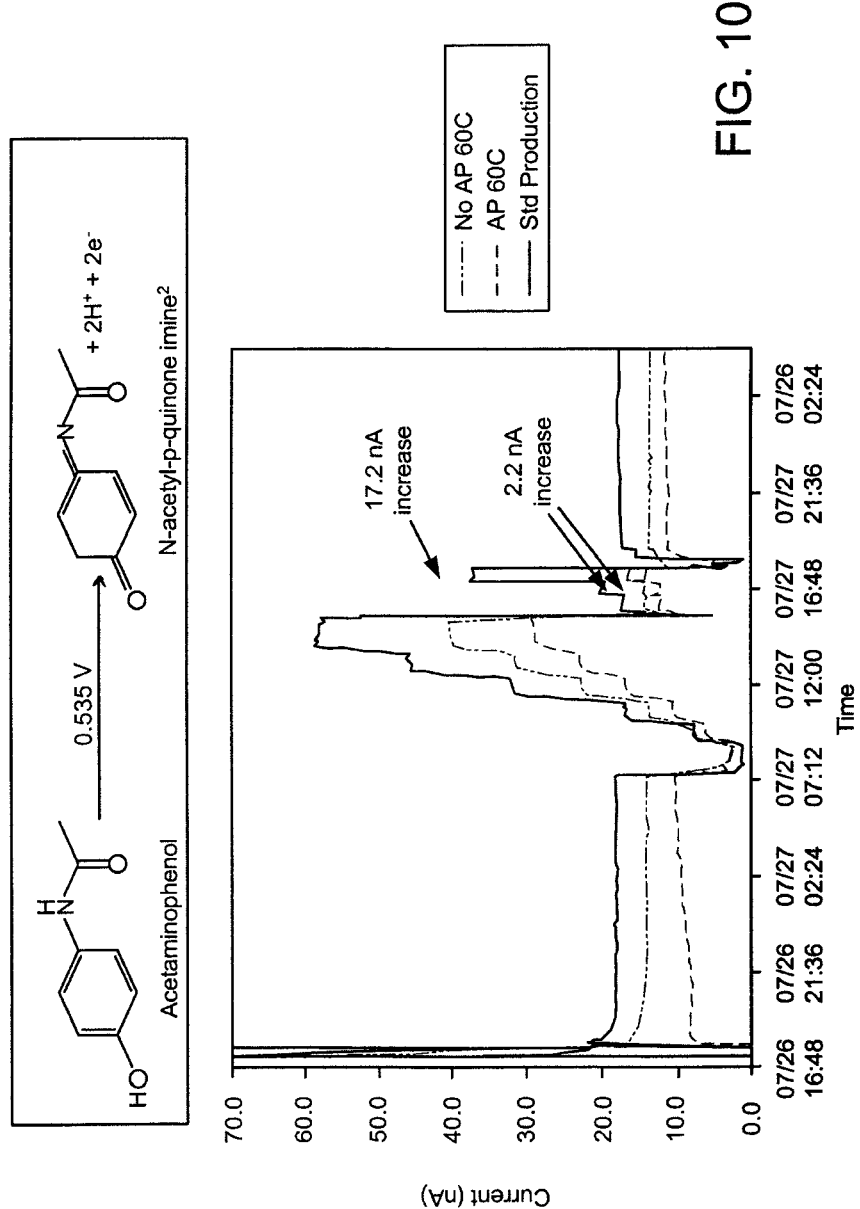
FIG. 10 provides a comparative graph of analyte (glucose) detection in the presence of acetominophenol by a sensor having an interference rejection constituent (one comprising a Nafion composition) as compared to a control sensor that does not comprise this constituent.

Typical embodiments of the invention comprise further layers such as an adhesion promoting layer disposed between the analyte sensing layer and the analyte modulating layer. Optionally in such embodiments, a first compound in the adhesion promoting layer is crosslinked to a second compound in the analyte sensing layer. Certain embodiments of the invention include an interference rejection layer, for example one comprised of a NAFION (a sulfonated tetrafluorethylene copolymer having the molecular formula C7HF13O5S. C2F4, CAS number [31175-20-9]) and/or a cellulose acetate composition. An illustrative embodiment of an interference rejection membrane (IRM) comprising NAFION and its effectiveness at inhibiting interfering signals that can be generated by acetominophenol in an amperometric sensor is shown in FIG. 10. Typically, an IRM is disposed under an analyte sensing layer (e.g. one comprising glucose oxidase). In certain embodiments of the invention, the IRM is disposed between the reactive surface of an electrode and an analyte sensing layer. Related embodiments of the invention include methods for inhibiting one or more signals generated by an interfering compound in various sensor embodiments of the invention (e.g. by using an interference rejection layer).

In typical embodiments of the invention, the sensor is operatively coupled to further elements (e.g. electronic components) such as elements designed to transmit and/or receive a signal, monitors, pumps, processors and the like. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase (and optionally two are coated with $GO_x$) and at least one working electrode is not coated with an analyte sensing layer comprising glucose oxidase. Such embodiments of the invention can be used for example in sensor embodiments designed factor out background signals in vivo, for example by comparing signal(s) at $GO_x$ coated working electrode(s) with signal at working electrode(s) not coated with $GO_x$ (e.g. background detection followed by a signal subtraction/cancellation process to arrive at a true signal).

Embodiments of the invention include sensors and sensor systems having configurations of elements and/or architectures that optimize aspects of sensor function. For example, certain embodiments of the invention are constructed to include multiple and/or redundant elements such as multiple sets of sensors and/or sensor system elements such as multiple piercing members (e.g. needles) and/or a cannulas organized on an insertion apparatus for use at a patient's in vivo insertion site. One embodiment of the invention is the dual piercing member or "fang" sensor system embodiment shown in FIGS. 12A and 12B. This embodiment of the invention is a sensor apparatus for monitoring a body characteristic of the patient, the apparatus comprising a base element adapted to secure the apparatus to the patient, a first piercing member that is coupled to and extending from the base element, wherein the first piercing member is operatively coupled to (e.g. to provide structural support and/or enclose) at least one first electrochemical sensor having at least one electrode for determining at least one body characteristic of the patient at a first sensor placement site, as well as a second piercing member that is coupled to and extending from the base element and operatively coupled to at least one second electrochemical sensor having at least one electrode for determining at least one body characteristic of the patient at a second sensor placement site. In some embodiments of the invention, such sensor systems are used in a hospital setting such as in an intensive care unit (e.g. to measure blood glucose concentrations in the interstitial fluid or blood of a diabetic patient). In other embodiments of the invention, the apparatus is used in an ambulatory context, for example by a diabetic in the daily monitoring of blood glucose.

Embodiments of the sensor systems disclosed herein are typically coupled to elements that facilitate their use in vivo such as flexible sensor substrates (e.g. to facilitate their use in an ambulatory context). In the specific illustrative embodiment of the invention shown in FIGS. 12A and 12B, the sensor system comprises two sensor flex substrates. In such embodiments, one or more sensing sets can be coupled to each flex substrate; for example an embodiment having four sensing sets, two coupled to each substrate. A wide variety of materials known in the art can be used to make such embodiments of the invention. In such embodiments, a cable can carry a current (e.g. a low current such as 10 nA) analogue signal with minimal noise over some distance (e.g. up to about 3, 4, 5, 6, 7, 8, 9 or 10 feet in length). The wires used to carry this current can be shielded in order to minimize noise due to interference/cross-talk, for example by using either a metal mesh (e.g. a braided and/or woven mesh), a solid metal wrap (e.g. one akin to aluminum foil), or are wound individual metal wires (e.g. akin to wrapping many hair like wires around to an assembly achieve the same effect as a solid wrap). The connector can be made of a material such as a rigid plastic (polycarbonate, ABS, polyethylene, PVC, vinyl, etc.). The outer sleeve of the cable can be made of a flexible/cleanable (resistant to chemicals) material such as polyurethane, vinyl, silicone, polyamide, etc. The material on the body can be a flexible base, for example one similar to that used in pediatric pulse-ox sensors or cloth Band-Aids.

As noted above, in certain sensor system embodiments, the electrodes are organized/disposed within a flex-circuit assembly. In such embodiments of the invention, the architecture of the sensor system including the flex substrates/sensors are separated by a distance great enough that: (1) a first sensor does not influence a signal etc. generated by a second sensor (and vice versa); and (2) they sense from separate tissue envelopes; so the signals from separate sensors do not interact. At the same time, in typical embodiments of the invention the flex substrates will be close enough so that they are easily packaged together and have a single insertion action.

One embodiment of the invention is an apparatus for monitoring an analyte in a patient, the apparatus comprising: a base element adapted to secure the apparatus to the patient; a first piercing member coupled to and extending from the base element; a first electrochemical sensor operatively coupled to the first piercing member and comprising a first electrochemical sensor electrode for determining at least one physiological characteristic of the patient at a first electrochemical sensor placement site; a second piercing member coupled to and extending from the base element; a second electrochemical sensor operatively coupled to the second piercing member and comprising a second electrochemical sensor electrode for determining at least one physiological characteristic of the patient at a second electrochemical sensor placement site. In such embodiments of the invention, at least one physiological characteristic monitored by the first or the second electrochemical sensor comprises a concentration of a naturally occurring analyte in the patient;

the first piercing member disposes the first electrochemical sensor in a first tissue compartment of the patient and the second piercing member disposes the second electrochemical sensor in a second tissue compartment of the patient; and the first and second piercing members are disposed on the base in a configuration selected to avoid a physiological response that can result from implantation of the first electrochemical sensor from altering a sensor signal generated by the second electrochemical sensor.

In some embodiments of the invention, the base comprises a flexible sensor substrate (e.g. one made from a polymeric composition such as a polyimide) that twists and bends in response to movement of implanted electrochemical sensors in the patient. Various sensor elements such as contact pads are typically disposed on such flexible sensor substrates. In some embodiments of the invention, the contact pads can be arranged near the edges of the flexible sensor substrate, with leads on the substrate connecting the sensors to the contact pads, for example to prevent the contact pads from being contaminated with the materials being tested. Embodiment can include printed circuit boards having a plurality of board contact pads arranged in the same configuration as the sensor contact pads in the sensor array. Connectors, such as conducting elastomers, stick probes, cantilever probes, conducting adhesives, wafer-to-board bonding techniques, or other contact devices, can couple the sensors with the printed circuit board by creating contacts between the sensor contact pads and the board contact pads, preferably the contacts are reversible and non-permanent.

Typically, the flexible sensor substrate includes a contact pad; an electrical conduit which connects an electrochemical sensor electrode to an electrical connection element that is operatively coupled to the contact pad. Optionally the apparatus comprises two contact pads connected to two electrical conduits and two sets of electrochemical sensor electrodes comprising a working, a counter and a reference electrode that are disposed on the flexible sensor substrate in a configuration such that the two contact pads are disposed together in a central region of the flexible sensor substrate so as to facilitate electrical connection to a power source and each of the two sets of electrochemical sensor electrodes is disposed on an opposite side of the flexible sensor substrate so as to maximize sensor separation (see, e.g. FIG. 13B); the two contact pads are disposed together one side of the flexible sensor substrate so as to facilitate electrical connection to a power source and the two sets of electrochemical sensor electrodes are disposed together in a row on an opposite side of the flexible sensor substrate so as to provide a compact design for patient use (see, e.g. FIG. 13C); or the two contact pads are disposed together one side of the flexible sensor substrate so as to facilitate electrical connection to a power source and the two sets of electrochemical sensor electrodes are disposed together in a staggered arrangement on an opposite side of the flexible sensor substrate so as to provide a compact design for patient use while providing a greater distance between each set of electrochemical sensor electrodes as compared to sensor electrodes not disposed together in a staggered arrangement (see, e.g. FIG. 13D). In typical embodiments of the invention, a contact pad and an electrode are at least, 15, 16, 17, 18, 19, 20, 21, 22, 23, 24 or 25 millimeters apart.

In certain embodiments of the invention, at least one electrochemical sensor electrode comprises oxidoreductase that generates hydrogen peroxide upon exposure to a ligand for the oxidoreductase. In some embodiments for example, the first and second electrochemical sensor comprises a working electrode, a counter electrode and a reference electrode; a working electrode in the first electrochemical sensor is coated with glucose oxidase; and no working electrode in the second electrochemical sensor is coated with glucose oxidase. Optionally, the first and second electrochemical sensors comprise a plurality of working, counter and reference electrodes that are grouped together as a unit and positionally distributed in a repeating pattern of units.

In some embodiments of the invention, the first and second electrochemical sensors are operatively coupled to a sensor input capable of receiving signals from the first and second electrochemical sensors; and a processor coupled to the sensor input, wherein the processor is capable of characterizing one or more signals received from the first and second electrochemical sensors. Optionally, a pulsed voltage is used to obtain a signal from an electrode. In certain embodiments of the invention, the processor is capable of comparing a first signal received from a working electrode in response to a first working potential with a second signal received from a working electrode in response to a second working potential.

A related embodiment of the invention is an apparatus for monitoring glucose concentrations in a patient, the apparatus comprising a flexible sensor substrate adapted to secure the apparatus to the patient; a first piercing member coupled to and extending from the flexible sensor substrate, wherein the first piercing member is operatively coupled to a first electrochemical sensor comprising a first electrochemical sensor electrode for measuring glucose concentrations at a first electrochemical sensor placement site; a second piercing member coupled to and extending from the flexible sensor substrate, wherein the second piercing member is operatively coupled to a second electrochemical sensor comprising a second electrochemical sensor electrode for determining at least one physiological characteristic of the patient at a second electrochemical sensor placement site; a processor capable of characterizing a plurality of signals received from the first and second electrochemical sensors. In such embodiments of the invention, the first piercing member disposes the first electrochemical sensor in a first tissue compartment of the patient and the second piercing member disposes the second electrochemical sensor in a second tissue compartment of the patient; and the first and second piercing members are disposed on the flexible sensor substrate in a configuration selected to avoid a physiological response to the implantation of the first electrochemical sensor from effecting a sensor signal generated by the second electrochemical sensor.

Optionally, the first and the second electrochemical sensor comprise an elongated base layer; a conductive layer disposed on the base layer and comprising a reference electrode, a working electrode and a counter electrode; an analyte sensing layer disposed on the conductive layer; an analyte modulating layer disposed on the analyte sensing layer, wherein the analyte modulating layer comprises a composition that modulates the diffusion of an analyte diffusing through the analyte modulating layer; and a cover layer disposed on the analyte sensor, wherein the cover layer comprises an aperture positioned on the cover layer so as to facilitate an analyte present in the patient contacting and diffusing through the analyte modulating layer and contacting the analyte sensing layer. Typically, the first and second electrochemical sensors comprise a plurality of working, counter and reference electrodes that are grouped together as a unit and positionally distributed on the conductive layer in a repeating pattern of units.

In certain embodiments of the invention, the first electrochemical sensor comprises a working electrode coated with glucose oxidase and the second electrochemical sensor comprises no working electrode coated with glucose oxidase and the processor is capable of obtaining information on glucose concentrations in the patient by comparing the signals received from said working electrodes so as to identify a background signal that is not based on a glucose concentrations in the patient. Optionally for example, the working electrode in the first and second electrochemical sensors are coated with glucose oxidase and the processor is capable of obtaining information on glucose concentrations in the patient by comparing the signals received from said working electrodes coated with glucose oxidase. In certain embodiments of the invention, the processor is used to assess sensor information derived from pulsed voltage scheme that is used to obtain a signal from an electrode. Optionally, the processor is capable of comparing a first signal received from a working electrode in response to a first working potential (e.g. 280, 535 or 635 millivolts) with a second signal received from a working electrode in response to a second working potential (e.g. 280, 535 or 635 millivolts).

In certain embodiments of the invention, the first and second electrochemical sensors comprise three working electrodes, one counter electrode and one reference electrode; at least one working electrode in the first and second electrochemical sensors is coated with glucose oxidase; and at least one working electrode in the first and second electrochemical sensors is not coated with glucose oxidase. Optionally, at least two working electrodes in the first and second electrochemical sensors are coated with glucose oxidase. Another embodiment of the invention is a method of monitoring an analyte within the body of a patient, the method comprising implanting an analyte sensor in to the patient, the analyte sensor comprising a base element adapted to secure the apparatus to the patient; a first piercing member coupled to and extending from the base element; a first electrochemical sensor operatively coupled to the first piercing member and comprising a first electrochemical sensor electrode for determining at least one physiological characteristic of the patient at a first electrochemical sensor placement site; a second piercing member coupled to and extending from the base element; a second electrochemical sensor operatively coupled to the second piercing member and comprising a second electrochemical sensor electrode for determining at least one physiological characteristic of the patient at a second electrochemical sensor placement site; a sensor input capable of receiving signals from the first and second electrochemical sensors; and a processor coupled to the sensor input, wherein the processor is capable of characterizing one or more signals received from the first and second electrochemical sensors. In such embodiments of the invention, at least one physiological characteristic monitored by the first or the second electrochemical sensor comprises a concentration of a naturally occurring analyte in the patient; the first piercing member disposes the first electrochemical sensor in a first tissue compartment of the patient and the second piercing member disposes the second electrochemical sensor in a second tissue compartment of the patient; the first and second piercing members are disposed on the base in a configuration selected to avoid a physiological response that results from implantation of the first electrochemical sensor from altering a sensor signal generated by the second electrochemical sensor; and sensing alterations in current at the first and second electrochemical sensor electrodes and correlating said alterations in current with the presence or absence of the analyte, so that the analyte is monitored.

In some methodological embodiments of the invention, the first electrochemical sensor comprises a working electrode coated with glucose oxidase and the second electrochemical sensor comprises no working electrode coated with glucose oxidase, the method further comprising using the processor to obtain information on glucose concentrations in the patient by comparing the signals received from the working electrodes in said first and second electrochemical sensors so that a background signal that is not based on a glucose concentrations in the patient is characterized. Optionally, the first electrochemical sensor comprises a working electrode coated with glucose oxidase and the second electrochemical sensor comprises a working electrode coated with glucose oxidase, the method further comprising using the processor to obtain information on glucose concentrations in the patient by comparing the signals received from the working electrodes in said first and second electrochemical sensors. Typically, at least one of the first and second electrochemical sensors is implanted in an interstitial space.

Figure 12A:
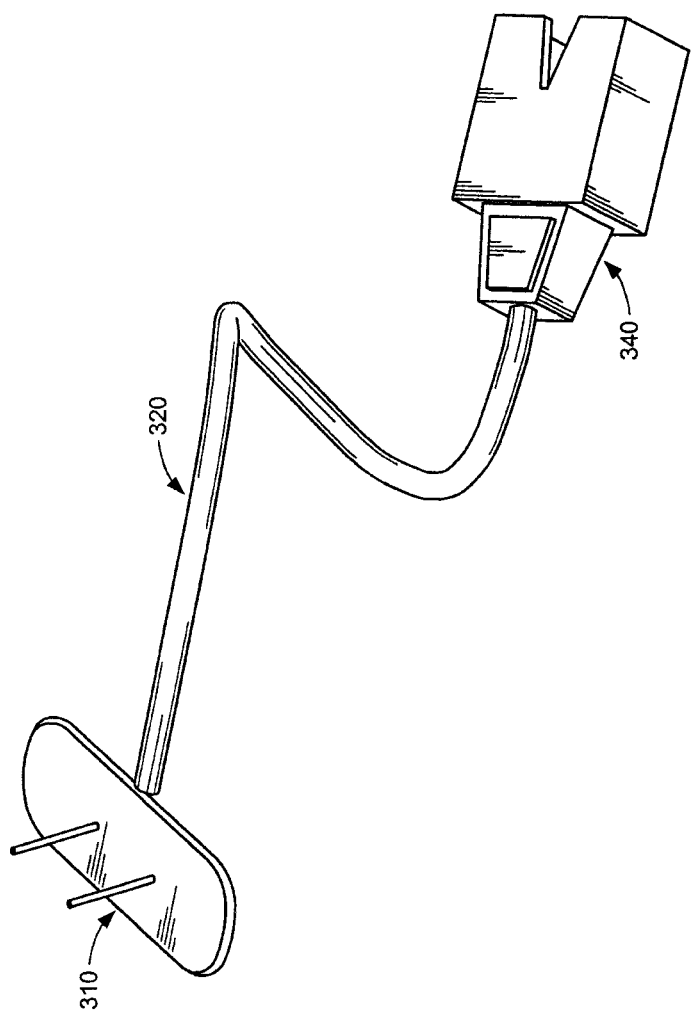
FIGS. 12A and 12B show dual piercing member or "fang" embodiments of the invention including a sensor flex substrate (310) coupled to a connector (340) via a cable (320).
Figure 12B:
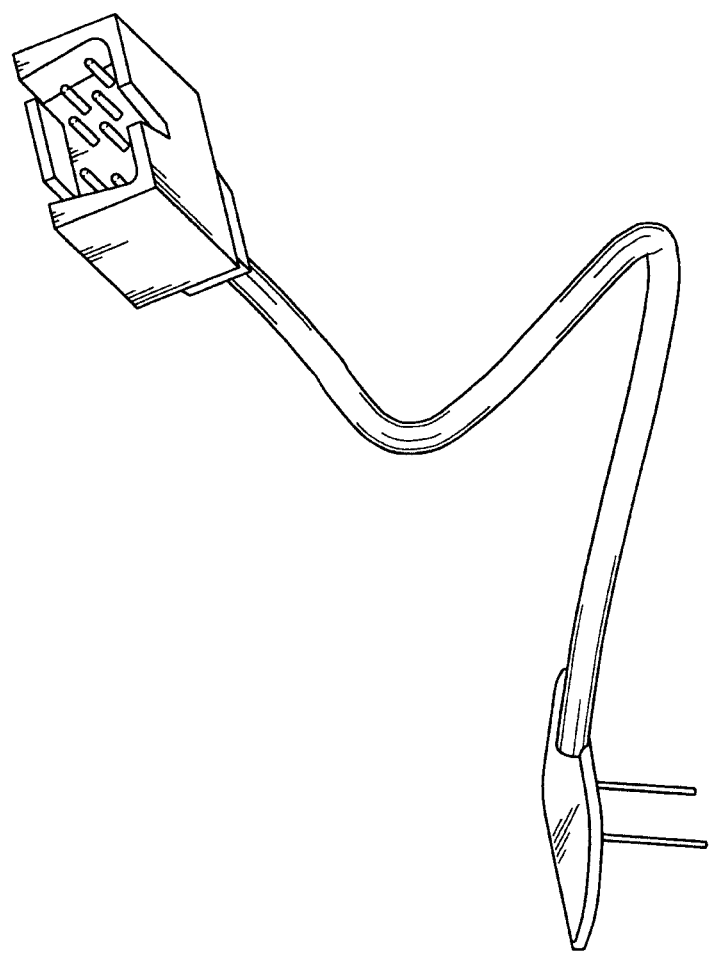
Figure 13B:
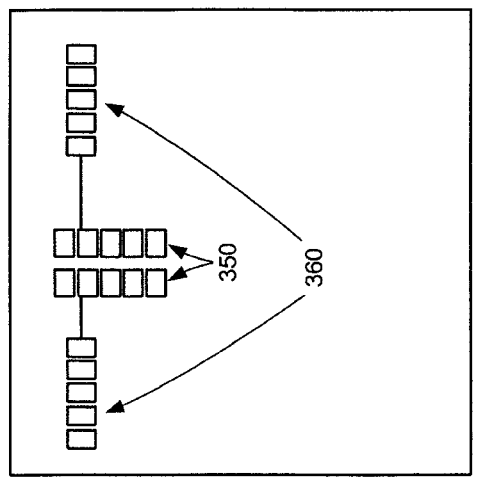
FIGS. 13A-13D provide schematics of sensor flex layouts. The embodiment shown in FIG. 13A has 2 columns of contact pads (350) on the left with the electrodes (360) on the right. The embodiment shown in FIG. 13B has the 2 columns of contact pads (350) at the center in between both sensor electrodes (360). The embodiment shown in FIG. 13C has a single column of contact pads (350) allowing for a different connection scheme with more width space than the design shown in FIG. 13A. The embodiment shown in FIG. 13D shows a staggered element layout. In embodiments of the invention that comprise multiple sensors, multiple groups of one or more of these layouts can be disposed together (e.g. in a repetitive pattern).
Figure 13A:
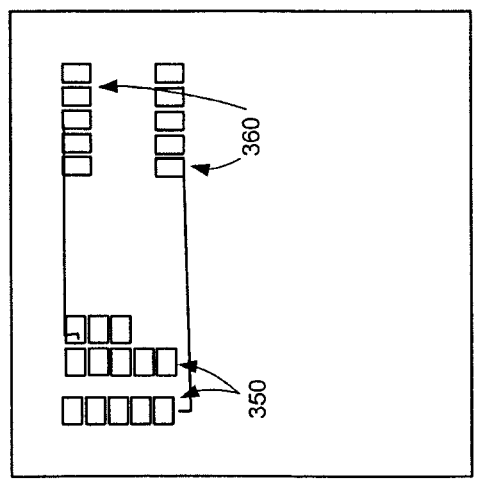
Figure 13D:
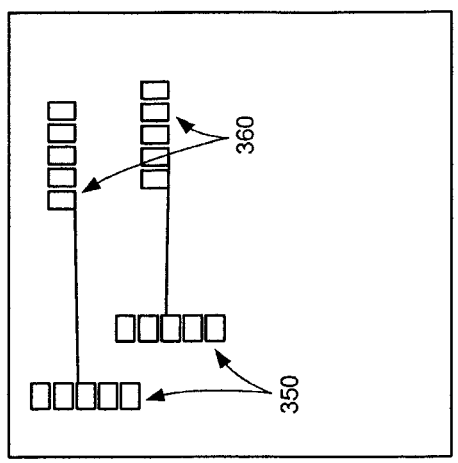
Figure 13C:
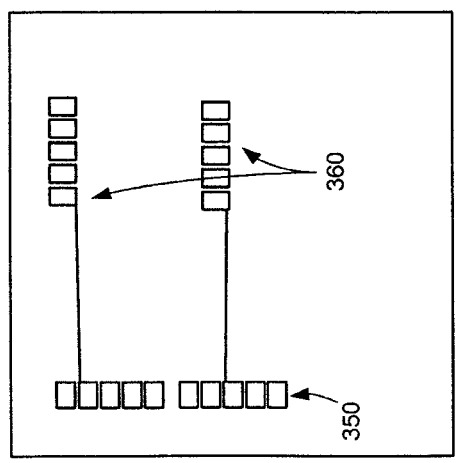

While specific embodiments of the invention such as those shown in FIGS. 12A and 12B can comprise two piercing members, optionally such sensor apparatuses can include 3 or 4 or 5 or more piercing members that are coupled to and extend from a base element and are operatively coupled to 3 or 4 or 5 or more electrochemical sensors (e.g. microneedle arrays, embodiments of which are disclosed for example in U.S. Pat. Nos. 7,291,497 and 7,027,478, and U.S. patent Application No. 20080015494, the contents of which are incorporated by reference). In addition, while embodiments of the invention typically include a base element that positions and supports the implanted sensors, (e.g. element (40) in FIG. 12), in alternative embodiments of the invention, the plurality of sensors are not coupled to a base element.

In some embodiments of sensors insertion set apparatuses, a first and a second (and/or third etc.) electrochemical sensor comprises one working, counter and reference electrode. Alternatively, the plurality of electrochemical sensors comprise a plurality of working, counter and reference electrodes, for example those having a distributed configuration as disclosed herein (see, e.g. FIG. 6). In certain embodiments of the invention, at least two in the plurality of sensors are designed to measure a signal generated by the same physiological characteristic, for example blood glucose concentration. Embodiments of the invention can include for example a plurality of electrochemical sensors having a working electrode coated with an oxidoreductase such as glucose oxidase and are used in methods designed to sample and compare glucose concentrations observed at the plurality of in vivo insertion sites. Alternatively, at least two in the plurality of sensors in the sensor apparatus are designed to measure signals generated by the different characteristics, for example a first characteristic comprising a background or interfering signal that is unrelated to blood glucose (e.g. "noise") and a second characteristic comprising blood glucose concentrations. In an illustrative embodiment of this invention, a first sensor is designed to measure glucose oxidase and comprises one or more working electrodes coated with glucose oxidase while a second comparative sensor is designed to measure a background or interfering signal that is unrelated to blood glucose has no working electrode (or electrodes) coated with glucose oxidase.

Embodiments of the invention can include a plurality of sensors coupled to a single piercing member in a manner that allows them to be disposed together in vivo at a single insertion site. One such embodiment of the invention comprises a sensor apparatus for monitoring a body characteristic of the patient, the apparatus comprising a base element adapted to secure the apparatus to the patient, a first piercing member coupled to and extending from the base element, wherein the first piercing member is operatively coupled to (e.g. provide structural support and/or enclose) at least two electrochemical sensors having at least one electrode for determining at least one body characteristic of the patient at a first sensor placement site, a second piercing member coupled to and extending from the base element and also operatively coupled to at least two electrochemical sensors having at least one electrode for determining at least one body characteristic of the patient at a second sensor placement site. In some embodiments of the invention, the at least two electrochemical sensors that are coupled to a piercing member are designed to measure a signal generated by the same characteristic, for example blood glucose concentration. Alternatively, the at least two electrochemical sensors that are coupled to a piercing member are designed to measure signals generated by the different characteristics, for example a first characteristic comprising a background or interfering signal that is unrelated to blood glucose (e.g. "noise") and a second characteristic comprising blood glucose concentrations.

Typical embodiments of the invention include a processor which compares the two (or more) signals produced by the plurality of sensors and, for example, then provides a physiological characteristic reading that is based upon the comparison of the plurality of signals. In one illustrative embodiment, the processor uses an algorithm to provide computational comparisons between a plurality of sensors having elements coated with an oxidoreductase such as glucose oxidase in order to, for example provide a comparative assessment of a physiological characteristic such as blood glucose at the different sites in which the sensors are inserted. In another illustrative embodiment, the processor includes an algorithm which provides a computational comparison between a plurality of sensors including at least one sensor having elements coated with an oxidoreductase such as glucose oxidase and at least one sensor not coated with glucose oxidase (e.g. which functions to identify background or interfering signals unrelated to blood glucose) in order to, for example subtract signals unrelated to blood glucose and in this way provide optimized sensor outputs. Certain embodiments of the invention include apparatuses capable of multiplexing the signals received from the plurality of sensors, e.g. by weaving multiple sensor signals onto a single channel or communications line. In such multiplexing embodiments of the invention, segments of information from each signal can be interleaved and separated by time, frequency, or space in order to obtain a comparative and comprehensive reading of all sensor outputs. Certain multiplexing embodiments of the invention include a processor which uses an algorithm to provide computational comparisons between signals received from the plurality of sensors (e.g. to provide a mean, average or normalized value for the sensor signals).

Embodiments of the invention that include a plurality of sensors such as those disclosed above can be used in methods designed to diminish or overcome problems associated with inserting a foreign body into the tissues of a patient (e.g. an immune response) and/or the variable anatomical features that can be encountered at a given insertion site (e.g. dermal layers that are of different thicknesses and/or depths in different individuals, the presence, absence or extent of adipose tissue deposits, the presence of preexisting scar tissue and the like), phenomena which can effect the hydration and initialization of a sensor. In particular, patient physiologies which include for example highly variable and unpredictable localized immune responses at the insertion site can cause problems with implantable sensors. For example, when a foreign object is implanted inside the body, one way the immune system can respond is to "wall off" the object in a fibrotic layer (e.g. so that it is encapsulated in a fibrotic capsule), a phenomena which can compromise the performance of an analyte sensor by inhibiting the ability of an in vivo analyte (e.g. glucose) from contacting the sensor (due to the fibrotic layer acting as a physical barrier). In addition, a patient's anatomical characteristics which include for example highly variable and unpredictable tissue properties at different insertion sites can cause problems with implantable sensors which can include for example different rates of analyte diffusion from the bloodstream to the site an implanted sensor, a phenomena which can compromise the performance of an analyte sensor by inhibiting the ability of a sensor to obtain relatively fast and/or accurate readings of blood glucose concentrations (e.g. a current or "real time" reading).

In typical method and device embodiments of the invention, the sensors in such apparatuses are separated by a distance selected to be great enough that the physiological response at a first insertion site for a first sensor(s) does not influence the signal generated at a first insertion site for a first sensor(s). In addition, in certain embodiments of the invention, the sensors in such apparatuses are separated by a distance great enough to allow the sensors to sense from separate tissue envelopes. For example, in one embodiment of the invention, the constellation of elements in the apparatus is arranged so that when the first and second piercing members are inserted into a patient, the first and second sensors are separated by at least 5, 6, 7, 8, 9, 10, 11, 12, 13, 14, 15, 20 or 25 millimeters of tissue. In another embodiment of the invention, the constellation of elements in the apparatus is arranged so that when the first and second piercing members are inserted into a patient, a first sensor is disposed within a layer of a first anatomical feature and/or characteristic such as an interstitial space (i.e. the small, narrow spaces between tissues or parts of an organ epidermis) and a second sensor is disposed within a layer of a second anatomical feature and/or characteristic such in a tissue or part of an organ. In one illustrative embodiment, a first sensor is disposed within the epidermis and a second sensor is disposed within the dermis. In another embodiment of the invention, a first sensor is disposed within adipose tissue and a second sensor is disposed within muscle tissue. In some embodiments of the invention, the piercing members are disposed on a base in a parallel configuration. Alternatively, the piercing members are disposed on a base in a non-parallel configuration (e.g. to facilitate a first sensor being disposed in a first anatomical feature and a second sensor is disposed within a second anatomical feature). Optionally, at least two sensors in an embodiment of the invention are disposed at about the same depth within the tissue in which they are implanted. Alternatively, at least two sensors in an embodiment of the invention are disposed at different depths within the tissue in which they are implanted.

Embodiments of the invention that include a plurality of sensors such as those noted above can overcome a variety of problems observed to occur with single sensors by providing multiple physiological characteristic readings at multiple insertion sites in a manner that compensates for or overcomes an occurrence of one or more of the above noted problems at a single insertion site. For example, by using embodiments of the invention constructed to include these elements, an immune response or problematical anatomical feature (e.g. scar tissue) at a single insertion site will not compromise the function of the multiple sensor apparatus in view of the multiple/redundant sensor signals that are provided by such embodiments of the invention. In addition, embodiments of the invention that include a plurality of sensors can use the multiple sensor signals to characterize, compensate for and overcome problems associated with "drift" that can occur with a single sensor at a single insertion site (i.e. the phenomena where an output signal of the sensor changes over time independent of the measured property).

Embodiments of the invention that include a plurality of sensors can be combined with other sensor elements and/or configurations disclosed herein in order to further optimize sensor function and can comprise for example electrodes distributed in a configuration that enhances the flexibility of the sensor structure and/or facilitates hydration of the sensor electrodes. Similarly, these embodiments of the invention can be combined with the apparatuses and methods that use voltage switching and/or pulsing as part of the initialization and/or sensing process as discussed in detail below.

As noted above, certain embodiments of the invention can use voltage switching as part of the sensing process. Embodiments of the invention can use voltage switching not only in the detection of interfering species and/or specific analyte concentrations but also to facilitate the hydration and/or initialization of various sensor embodiments of the invention. In particular, the time for initialization ("run-in") differs for different sensors and can take hours. Embodiments of the invention include a sensor initialization scheme involving high frequency initialization (switching of voltage potentials). In one illustrative embodiment, a triple initialization profile is used where the voltage of the sensor is switched between a first potential such as 0, 280, 535, 635 or 1.070 millivolts and a second potential such as 0, 280, 535, 635 or 1.070 millivolts over a period of 5, 10, 20, 30 or 45 seconds or 1, 5, 10 or 15 minutes. Certain voltage switching embodiments of the invention further use voltage pulsing in the detection of analyte signals. The number of pulses used in such embodiments of the invention is typically at least 2 and can be 3, 4, 5, 6, 7, 8, 9, 10, 15, 20 or more. Pulses can be for a predetermined period of time, for example 1, 3, 5, 7, 10, 15, 30, 45, 60, 90 or 120 seconds. One illustrative example of this comprises 6 pulses, each a few seconds long. By using such embodiments of the invention, the sensor run-in is greatly accelerated, a factor which optimizes a user's introduction and activation of the sensor. Certain of these methods can be adapted for use with similar methods known in the art (see, e.g. U.S. Pat. Nos. 5,320,725; 6,251,260 and U.S. Patent Application No. 2005/0161346, the content of which are incorporated by reference).

Figure 4A:
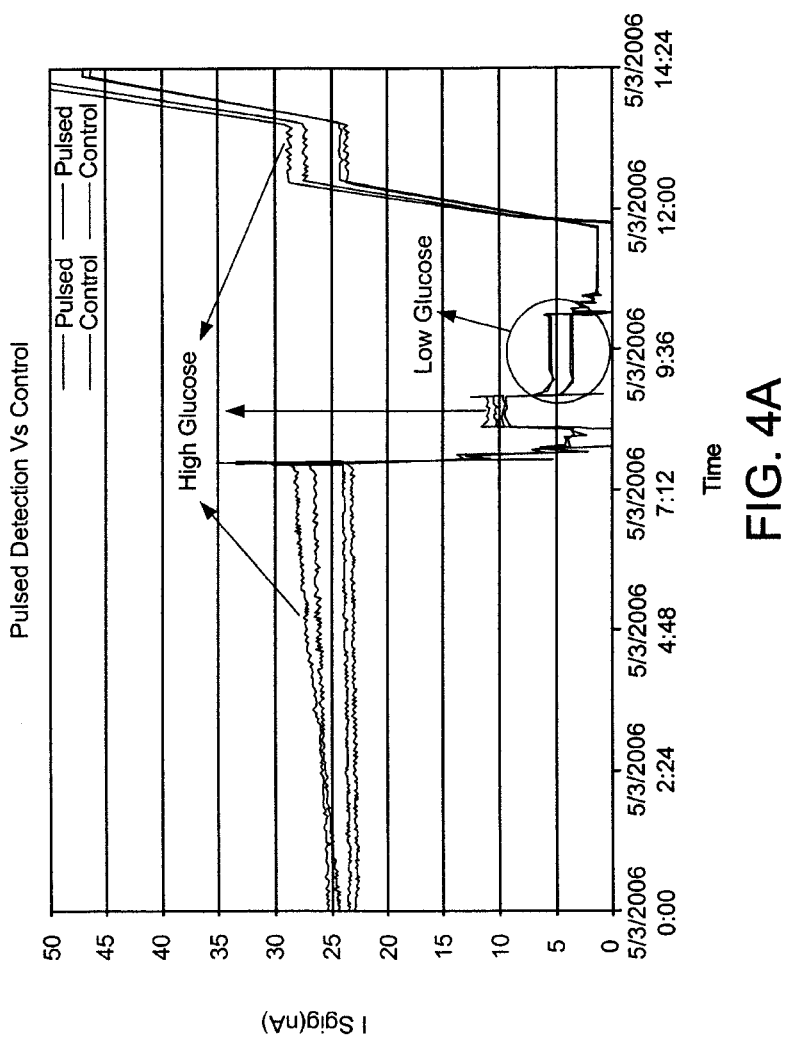
FIG. 4A provides a comparative graph of analyte (glucose) detection under pulsed and non-pulsed (control) detection schemes. The ISgig(nA) readings for the pulsed sensor are higher than those of the non-pulsed sensor at almost all datapoints aside from the low readings including those circled and identified as "low glucose". The data provided in this graph show that a pulsed detection scheme improves sensor sensitivity at specific concentration ranges by allowing for higher sensor reading at high glucose concentrations as well as lower sensor reading at low glucose concentrations. This data was generated by subjecting a sensor to an intermittent voltage pulse of 0.535 V for 5 times, six times per minute (the time between consecutive pulses being 5 seconds). The sensitivity of the pulsed sensor proved to be higher (higher current output compared to the non-pulsed sensor for a given glucose concentration) at higher concentrations. At lower concentrations, the output current from the pulsed detection sensor was lower than that of the non-pulsed sensor.
Figure 4B:
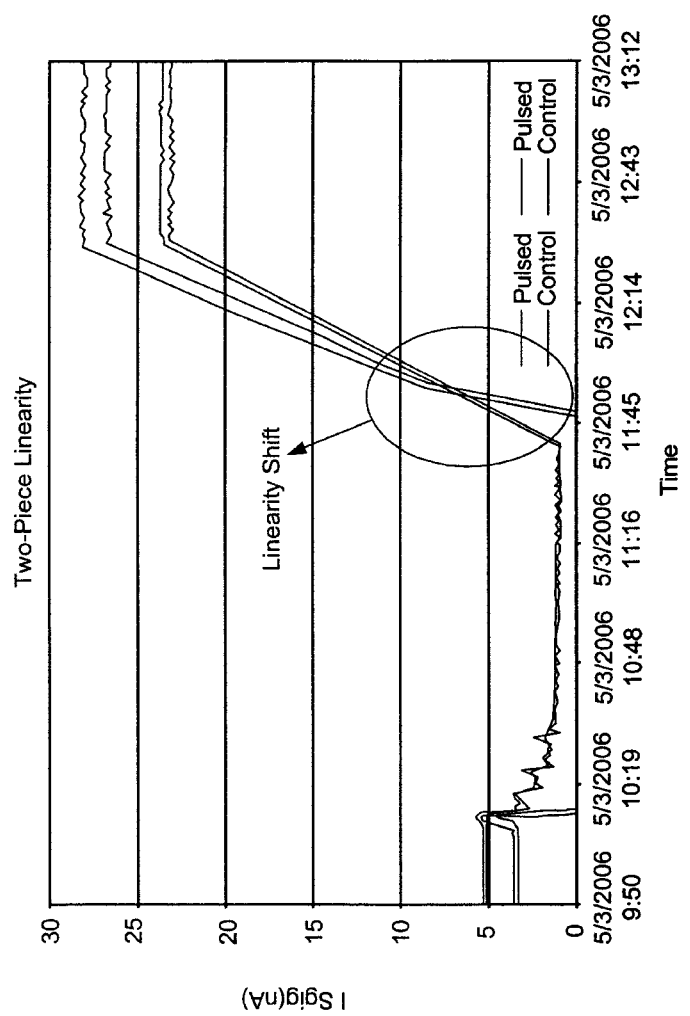
FIGS. 4B and 4C provides further comparative graphs of analyte (glucose) detection under pulsed and non-pulsed (control) detection schemes.
Figure 4C:
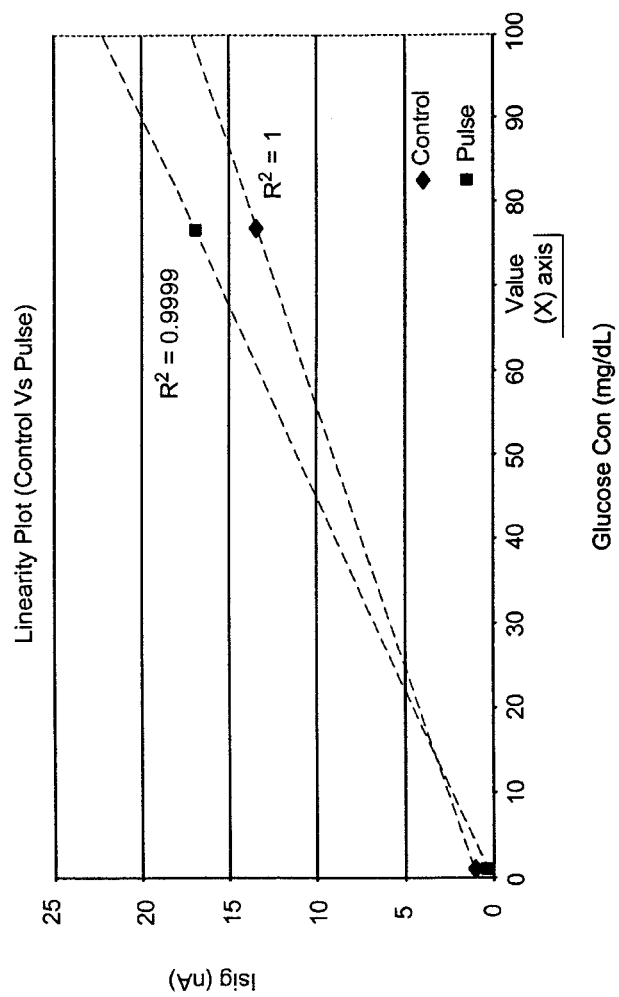
Figure 4D:
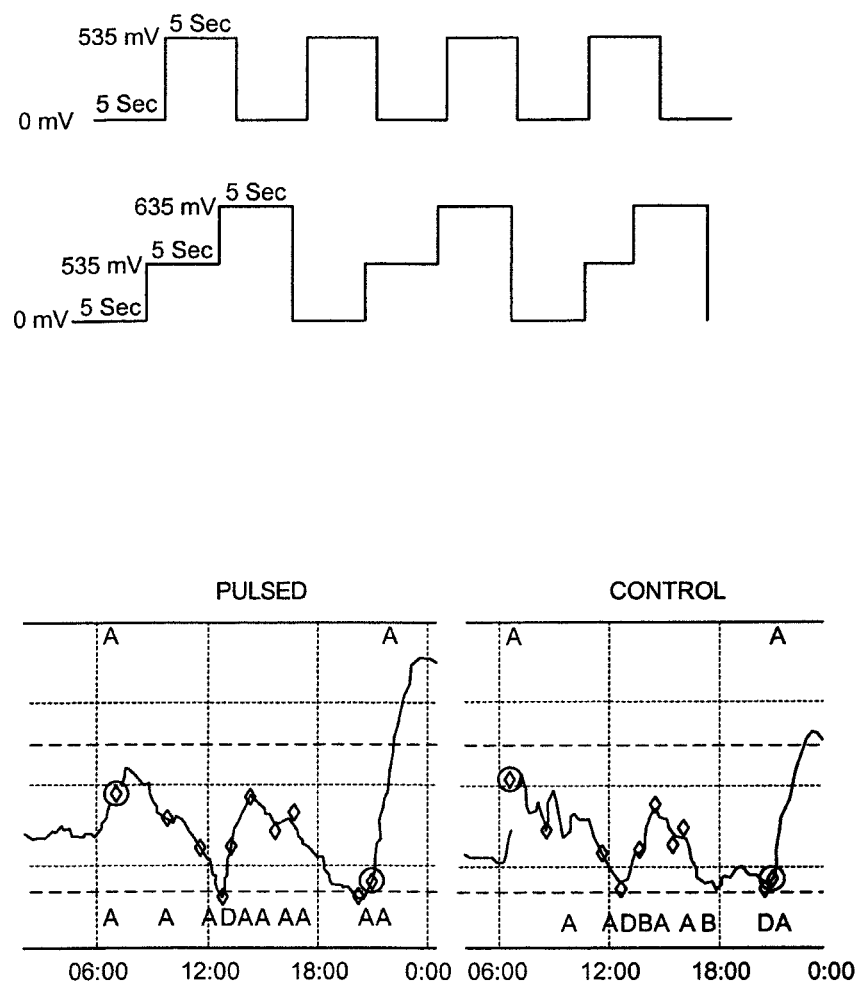
FIG. 4D provides voltage pulsing schematics (left) and associated data presented in comparative graphs (right) of sensors detecting glucose under pulsed or non-pulsed (control) conditions. The data provided in FIG. 4D shows that a pulsed detection scheme tracks changes in glucose concentrations better than a comparative scheme that does not employ voltage pulsing. These graphs show that pulsing allows sensors to detect lower concentrations of glucose more efficiently, that there is a linear response to glucose switching, and that pulsing can be used to both decrease the background current and reduce the effect of interferents.

In some embodiments of the invention, a pulsed (e.g. produced or transmitted or modulated in short bursts or pulses) voltage is used to obtain a signal from one or more electrodes of the sensor. In related embodiments of the invention, the use of a pulsed current or the like is used. Such pulsing for example can be used to reduce/compensate for background current readings. For example, FIGS. 4B and 4C provides a comparative graphs of analyte (glucose) detection under pulsed and non-pulsed (control) detection schemes. The data provided in these graphs show that pulsed sensors have a two-piece linearity. For example, the slope of the current Vs time plot is much steeper at lower concentrations. FIG. 4D provides comparative graphs of sensors detecting glucose under pulsed or non-pulsed (control) conditions. These graphs show that pulsing allows sensors to detect lower concentrations of glucose more efficiently, that there is a linear response to glucose switching, and that pulsing can be used to both decrease the background current and reduce the effect of interferents. To eliminate the possibility of the sensors in these studies having a A variety of different voltage pulsed and/or voltage switched sensor embodiments are contemplated. In this context, sensor systems can include a processor including software algorithms that control factors such as voltage output and/or working potential and/or pulsing and or switching and/or the time periods of such factors. Sensor systems can also include various hardware features designed to facilitate voltage pulsing, for example discharge circuit elements. In particular, in certain embodiments of the invention, high frequency switching can require a discharge circuit element so that layers discharge held charge (wherein the sensor layers analogous to a capacitor). One illustrative embodiment is sensor having two specific potential dedicated electrodes (e.g. at 280 my and 535 my) and is designed to obtain readings of both electrodes as sensor switches between them. In this context, it is known in art to take sensor reading at a wide range of potentials (see, e.g. U.S. Pat. Nos. 5,320,725, 6,251,260, 7,081,195 and Patent Application No. 2005/0161346). In one illustrative embodiment of the invention, a processor is used to observing signals obtained from one of two working electrodes in a sensor via a pulsed voltage and comparing it to the signal obtained from the second working electrode, wherein this second working electrode is not exposed to a pulsed voltage.

In some embodiment of the invention, a sensor functions by applying a first voltage for a first time to initiate an anodic cycle in the sensor, by applying a second voltage for a second time to initiate a cathodic cycle in the sensor, and repeating the application of the first voltage and the second voltage to continue the anodic-cathodic cycle in the sensor. In an embodiment of the invention, a sensor may function by applying a first voltage for a first time, by waiting a predetermined period of time (i.e., not applying a voltage), and then cycling between the application of the first voltage and the waiting of a predetermined period of time for a number of iterations or a specific timeframe. The first voltage may have a positive value or a negative value. The second voltage may have a positive value or negative value. Under certain operating conditions, a voltage magnitude of the first voltage for one of the iterations may have a different magnitude from a voltage magnitude of the first voltage for a second or different iteration. In an embodiment of the invention, a voltage waveform, such as a ramp waveform, a stepped waveform, a sinusoid waveform, and a squarewave waveform, may be applied as the first voltage. Any of the above mentioned waveforms may also be applied as the second voltage. Under certain operating conditions, the voltage waveform applied as the first voltage in a first iteration may differ from the voltage waveform applied as the first voltage in the second iteration. The same may hold true for the application of the second voltage. Under certain operating conditions, a voltage waveform may be applied as the first voltage to the sensor and a voltage pulse may be applied as the second voltage to the sensor.

In an embodiment of the invention, a plurality of short duration voltage pulses are applied for the first timeframe to initiate the anodic cycle in the sensor. In such embodiments, a plurality of short duration voltage pulses may be applied for the second timeframe to initiate the cathodic cycle in the sensor. The magnitude of the first plurality of short duration pulses may be different from the magnitude of the second plurality of short duration pulses. In an embodiment of the invention, the magnitude of some of the pulses in the first plurality of short duration pulses may have different values from the magnitude of other pulses in the first plurality of short duration pulses. The shorter duration voltage pulses may be utilized to apply the first voltage, the second voltage, or both. In an embodiment of the present invention, the magnitude of the shorter duration voltage pulse for the first voltage is −1.07 volts and the magnitude of the shorter duration voltage pulse for the second voltage is approximately half of the high magnitude, e.g., −0.535 volts. Alternatively, the magnitude of the shorter duration pulse for the first voltage may be 0.535 volts and the magnitude of the shorter duration pulse for the second voltage is 1.07 volts.

In embodiments of the invention utilizing short duration pulses, the voltage may not be applied continuously for the entire first time period. Instead, in the first time period, the voltage application device may transmit a number of short duration pulses during the first time period. In other words, a number of mini-width or short duration voltage pulses may be applied to the electrodes of the sensors over the first time period. Each mini-width or short duration pulse may a width of a number of milliseconds. Illustratively, this pulse width may be 30 milliseconds, 50 milliseconds, 70 milliseconds or 200 milliseconds. These values are meant to be illustrative and not limiting.

In another embodiment of the invention, each short duration pulse may have the same time duration within the first time period. For example, each short duration voltage pulse may have a time width of 50 milliseconds and each pulse delay between the pulses may be 950 milliseconds. In this example, if two minutes is the measured time for the first timeframe, then 120 short duration voltage pulses may be applied to the sensor. In an embodiment of the invention, each of the short duration voltage pulses may have different time durations. In an embodiment of the invention, each of the short duration voltage pulses may have the same amplitude values. In an embodiment of the invention, each of the short duration voltage pulses may have different amplitude values. By utilizing short duration voltage pulses rather than a continuous application of voltage to the sensors, the same anodic and cathodic cycling may occur and the sensor (e.g., electrodes) is subjected to less total energy or charge over time. The use of short duration voltage pulses utilizes less power as compared to the application of continuous voltage to the electrodes because there is less energy applied to the sensors (and thus the electrodes).

In certain embodiments of the invention, sensor systems that utilize voltage pulsing and/or switching as disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that utilize voltage pulsing and/or switching can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, etc.).

Figure 11:
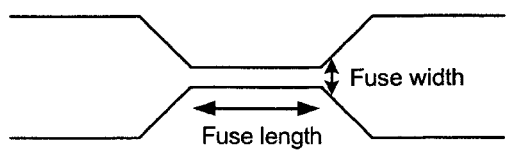
FIG. 11 provide photographs of fuse elements that can be used in embodiments of the invention. In such fuse embodiments, the function of the fuse can be controlled for example by constructing it to trigger upon a certain electrical potential, a functional feature that can be modulated for example by modulating the trace width and trace thickness.
Figure 11:
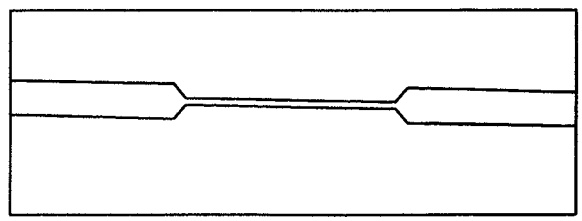
Figure 11:
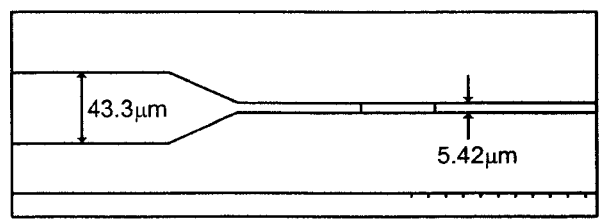

Some embodiments of the invention include a fuse element that can be triggered after a predetermined period of time or event so as to interrupt a flow of electrical current within the apparatus (i.e. so as to disable the sensor). For example, one embodiment of the invention includes a sensor operatively coupled to a sensor input capable of receiving a signal from the sensor that is based on a sensed physiological characteristic value in the mammal; and a processor coupled to the sensor input, wherein the processor is capable of triggering a fuse element to disable the sensor after a predetermined period which is based upon the in vivo lifetime of the sensor. In a related embodiments of the invention, the processor is capable of triggering a fuse element upon receipt of a signal that is outside of a predetermined set of signal parameters that are associated with normal sensor function. In one such embodiment of the invention, parameters that are outside of those associated with normal sensor function includes a current that is above a prescribed maximum or is below a prescribed minimum for more than a prescribed time. Related embodiments of the invention include methods for disabling a sensor embodiments of the invention (e.g. by using a fuse element), for example a sensor which has exceeded a predetermined period of operation (e.g. lifespan) and/or a sensor that is not performing within a predetermined set of operating parameters. A variety of fuse elements known in the art can be adapted for use with the sensor embodiments disclosed herein. One illustrative embodiment of a fuse element is shown in FIG. 11.

Certain sensor embodiments that include a fuse element can include a plurality of fuse elements, that for example can be triggered individually by different events. In one illustrative embodiment of the invention that comprises two fuse elements, both of which must be triggered to disable sensor function, a first fuse element is triggered upon initialization of start-up of the sensor; and the second fuse element is triggered after a certain time period, for example 1, 3, 5, 7, 14, 21 or 30 days. Such embodiments of the invention are useful for example to prevent a user from using the sensor in vivo longer than its appropriate lifetime. Other embodiments of the invention having a fuse element can be constructed to trigger a fuse upon being connected/disconnected to a circuit and used for example to prevent users from disconnecting and/or reconnecting the sensor. Some embodiments of the invention further comprise a discharge circuit element (e.g. a switch) and/or a potentiostat operatively coupled to the sensor to facilitate an electrical discharge from the sensor. In certain embodiments of the invention, sensor systems that utilize fuse elements as disclosed herein are used in methods designed to overcome problems that can occur with the use of a sensor past its approved lifetime and/or sensor malfunction. One illustrative methodological embodiment is a method of preventing a sensor from: (1) functioning past its approved lifetime: and/or (2) providing readings to a user while malfunctioning comprising by coupling the sensor to a fuse element that is designed to trigger and turn off sensor function after a predetermined time period and/or the sensor performs outside of a predetermined set of operating parameters.

Figure 5A:
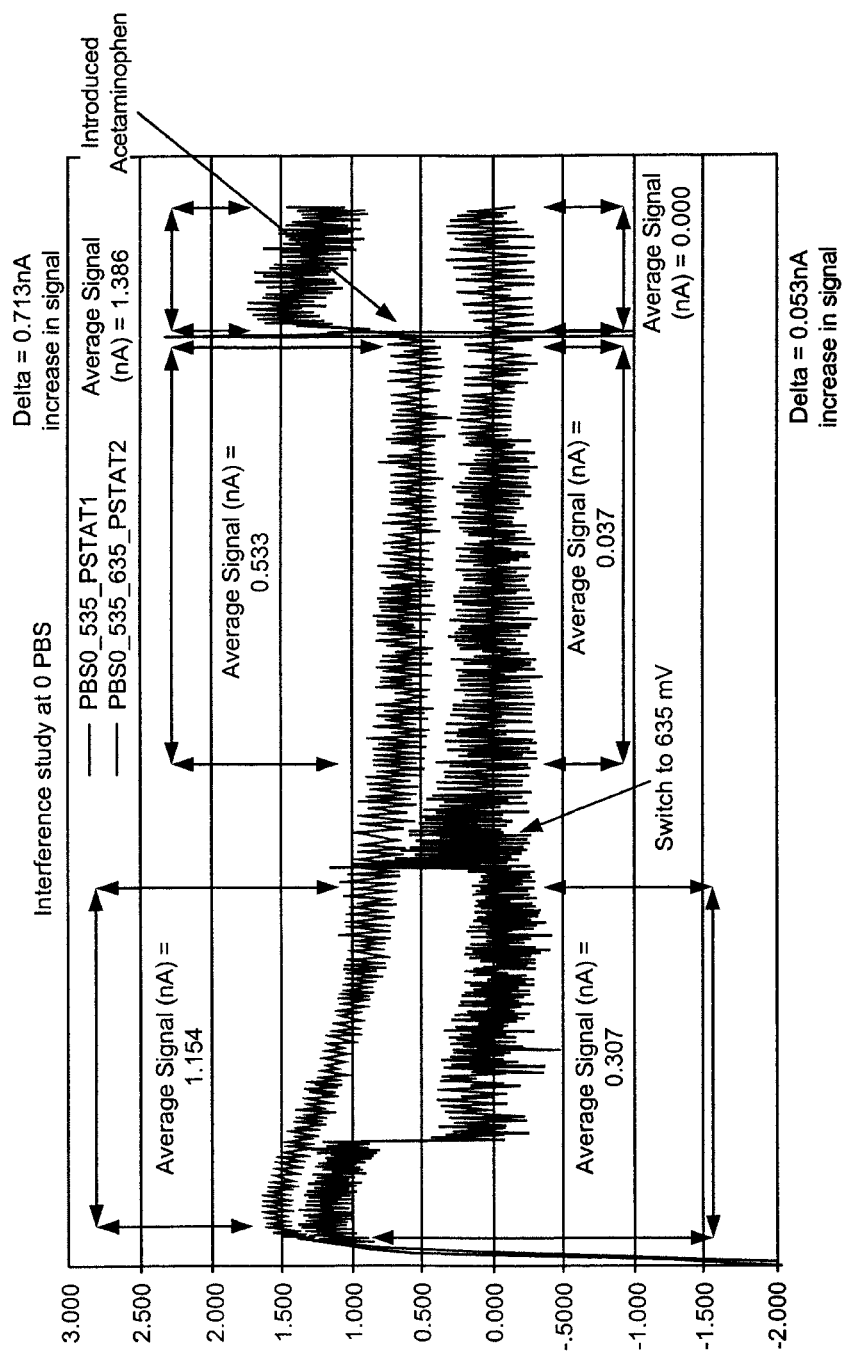
FIG. 5A provides comparative graphs of analyte (glucose) detection under switched output currents (0.535 and 0.635 Volts) in the presence of acetaminophen. This data shows how the output currents are effected due to the presence of interfering compounds at different working potentials. In this embodiment of the invention, the sensor at 0.535V had a positive response to the interfering compound while the sensor at 0.635V did not.
Figure 5B:
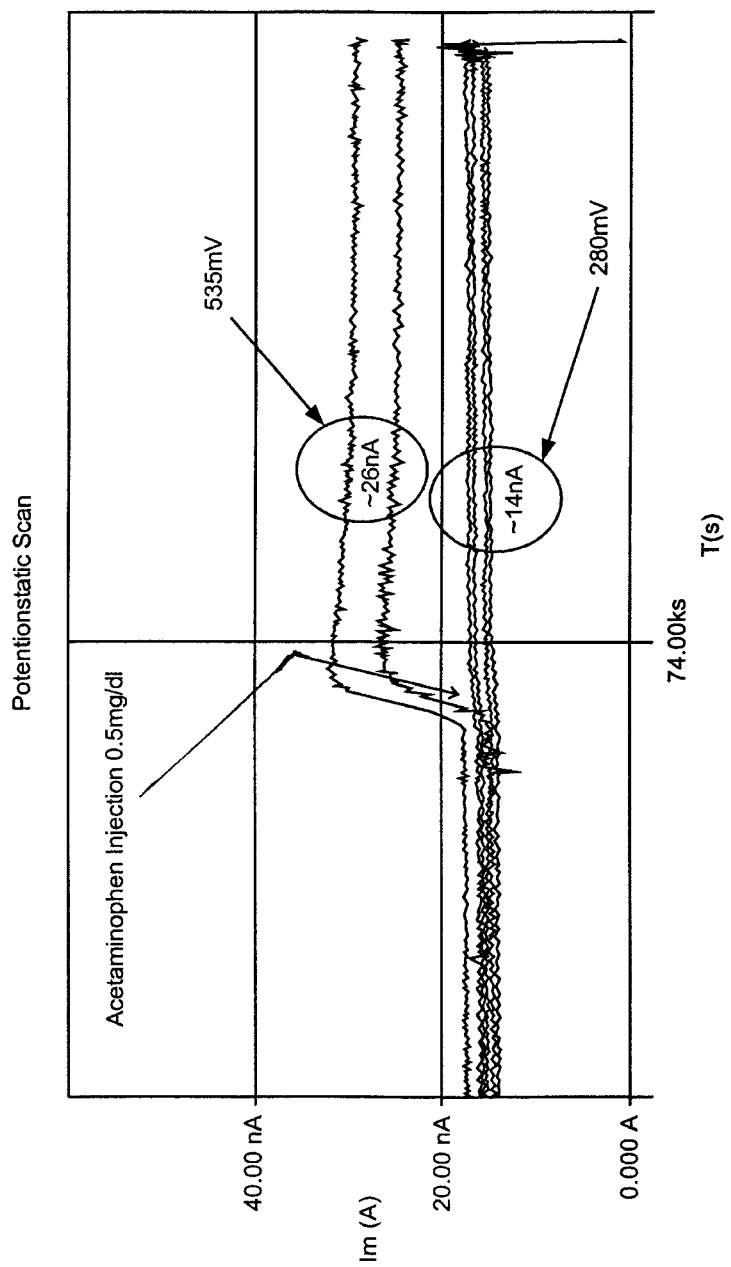
FIG. 5B provides further comparative graphs of analyte (glucose at 90.4 mg/dl) detection under different output currents (0.535 and 0.280 Volts) in the presence of acetaminophen. This data shows how the output currents are effected due to the presence of interfering compounds at different working potentials. This embodiment of the invention illustrates certain benefits of voltage switching, i.e. the sensor at 0.535V has a positive response to the interfering compound while the sensor at 0.280V does not.
Figure 6A:
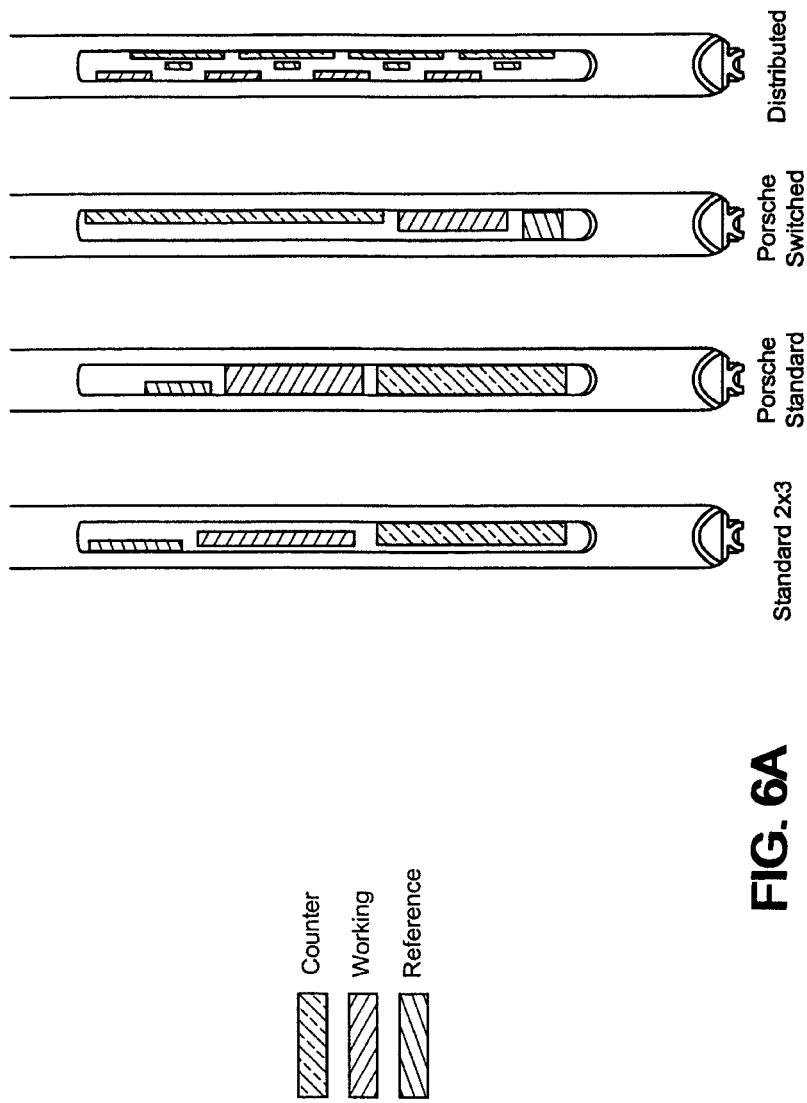
FIG. 6A provides a diagram of different electrode configurations in various sensor embodiments.
Figure 6B:
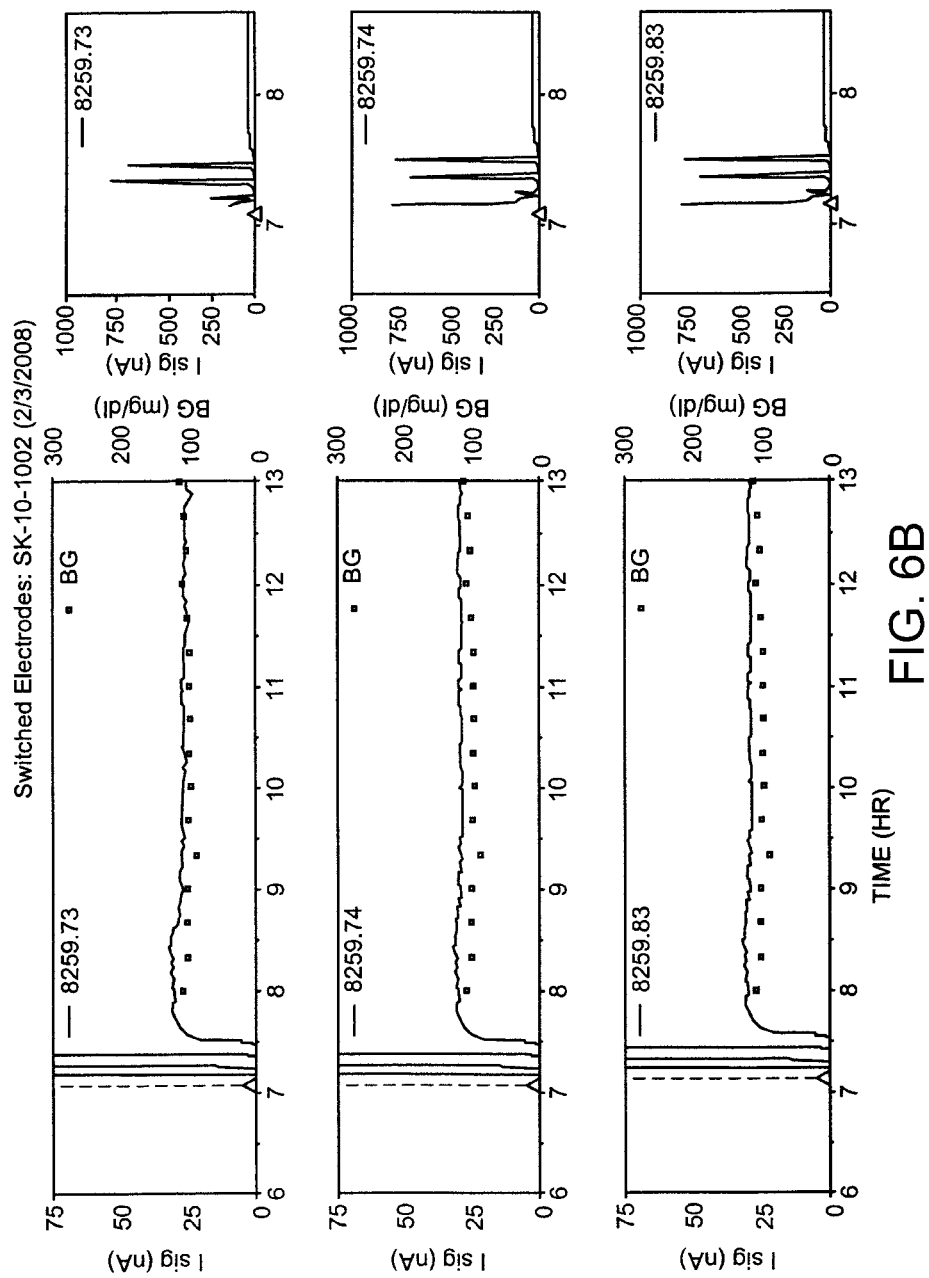
FIGS. 6B-6D provide a diagram of a switched working/reference/counter electrode configuration embodiment and associated test data on the impact of this configuration on sensor start-up.
Figure 6C:
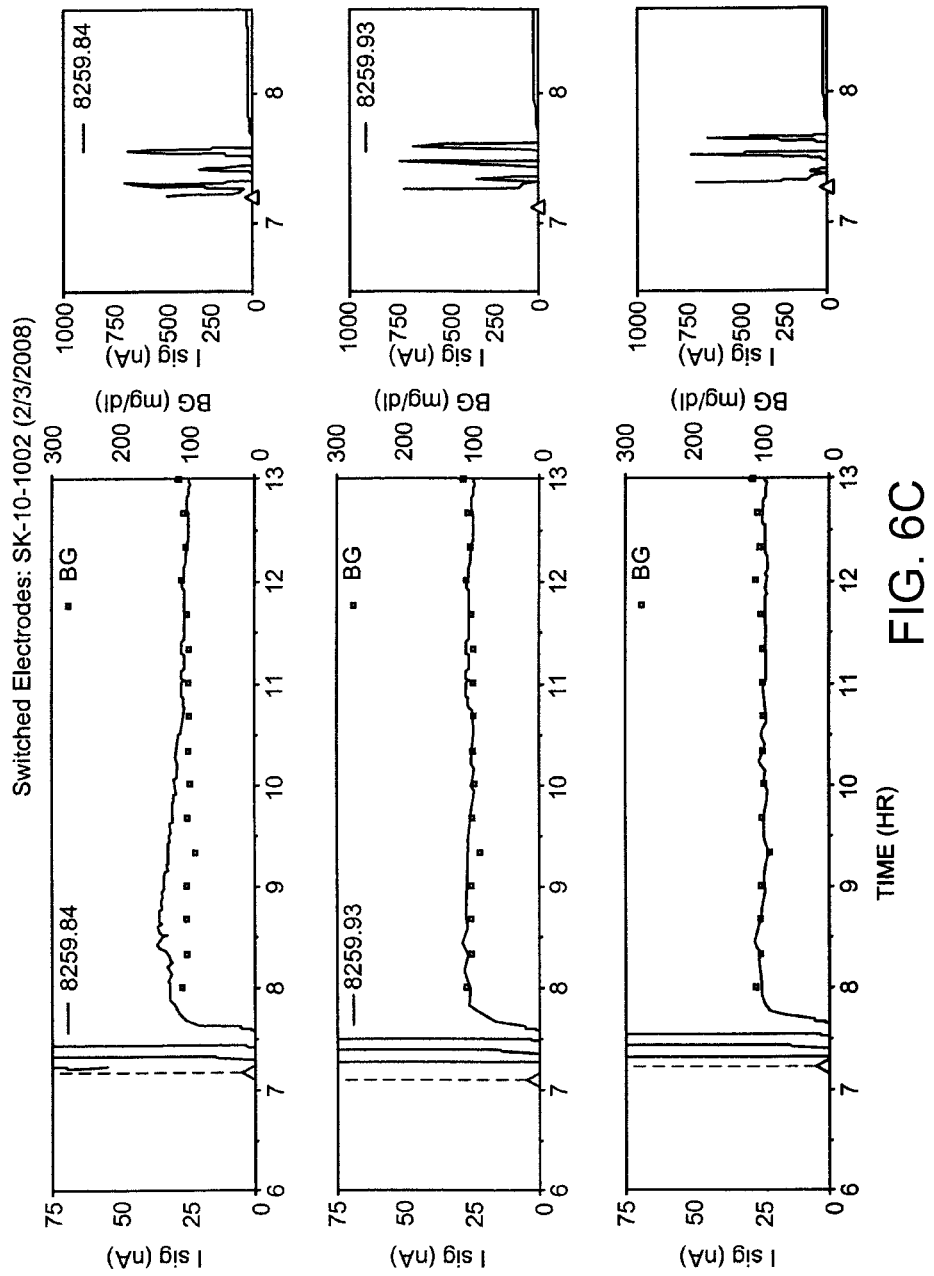
Figure 6D:
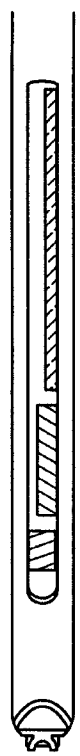
Figure 6E:
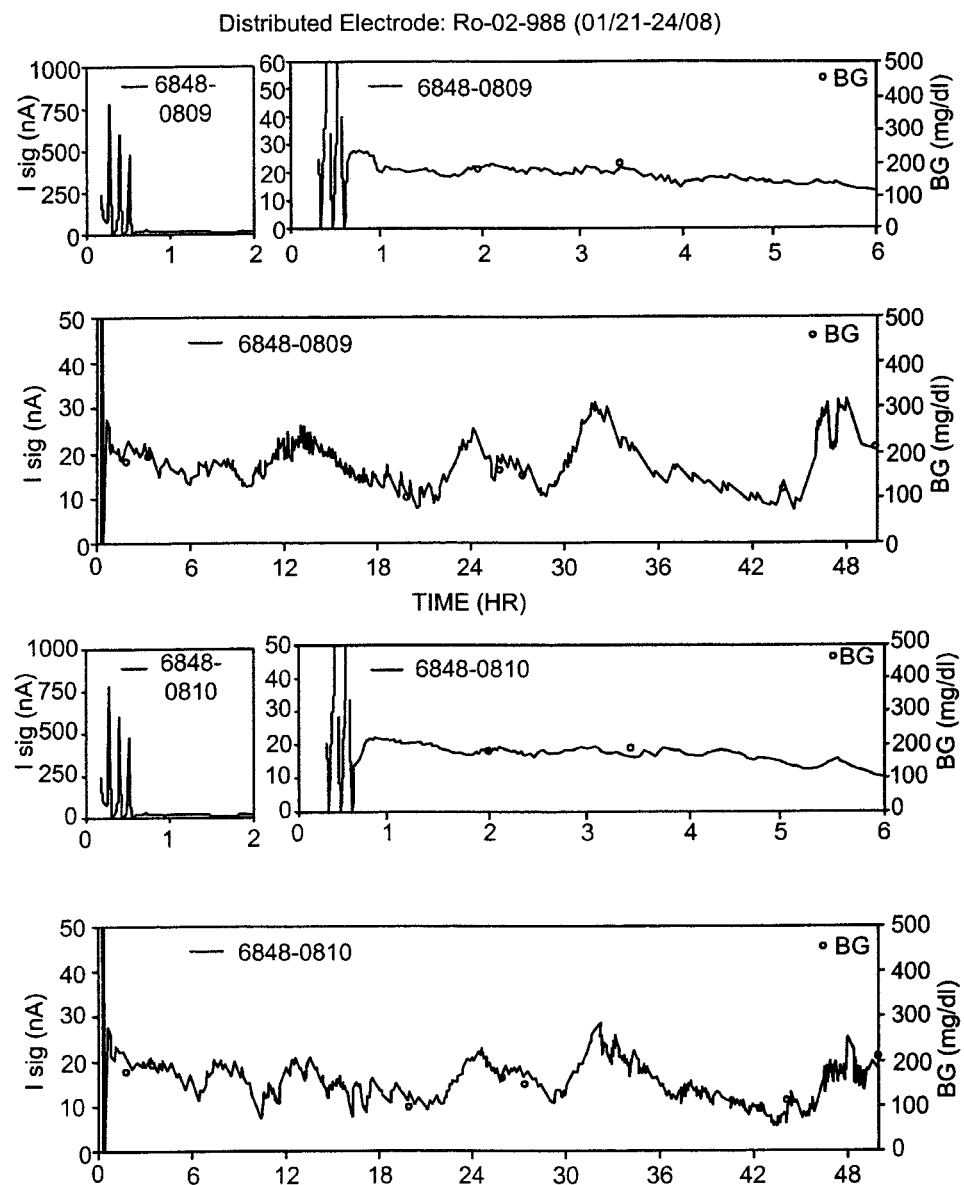
FIGS. 6E-6F provide a diagram of a distributed electrode configuration embodiment and associated test data on the impact of this configuration on sensor start-up.
Figure 6F:
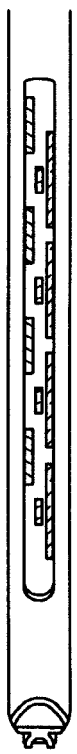

In some embodiments of the invention, a processor is capable of comparing a first signal received from a working electrode in response to a first working potential with a second signal received from a working electrode in response to a second working potential, wherein the comparison of the first and second signals at the first and second working potentials can be used to identify a signal generated by an interfering compound (see, e.g. FIGS. 5A and 5B). In one such embodiment of the invention, one working electrode is coated with glucose oxidase and another is not, and the interfering compound is acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides or uric acid. Optionally, a pulsed and/or varied (e.g. switched) voltage is used to obtain a signal from a working electrode. Typically, at least one voltage is 280, 535 or 635 millivolts. Related embodiments of the invention include methods for identifying and/or characterizing one or more signals generated by an interfering compound in various sensor embodiments of the invention (e.g. by comparing the signal from an electrode coated with an analyte sensing compound with a comparative electrode not coated with an analyte sensing compound). Optionally, such methods use a pulsed and/or varied working potential to observe a signal at an electrode. As shown in FIGS. 5A and 5B, an amperometric glucose sensor detects an interfering signal generated by acetaminophen at an operating potential of 535 mV and further that this interfering signal is suppressed when the sensor is switched to an operating potential 280 mV. This data shows that reducing the operating potential from 535 mV to 280 mV suppresses signals generated by acetaminophen over a range of glucose concentrations (0-400 mg/dL). In addition, this data shows that the reduced operating potential allows the sensor to maintain the 535 mV equivalent linearity.

In a related embodiment of the invention, a processor compares a first signal received from a working electrode coated with glucose oxidase in response to a first working potential with a second signal received from a working electrode coated with glucose oxidase in response to a second working potential, wherein the comparison of the first and second signals at the first and second working potentials is used to characterize a blood glucose concentration within at least one discreet concentration range. In certain embodiments of the invention at least two working potentials of approximately 280, 535 or 635 millivolts is used. In some embodiments of the invention, the comparison of the first and second signals at the first and second working potentials can be used to characterize a blood glucose concentration within a concentration range below 50 or 70 mg/dL (i.e. values typically associated with hypoglycemia) or above 125, or 150 mg/dL (i.e. values typically associated with hyperglycemia). In certain embodiments of the invention a 280 my potential is used because it can detect lower concentrations of glucose more efficiently. Related embodiments of the invention include methods for identifying and/or characterizing a specific analyte concentration or range of analyte concentrations using the various sensor embodiments of the invention (e.g. by comparing the analyte signal from one or more electrodes at different working potentials, wherein the different working potentials are selected for their ability to characterize a specific analyte concentration and/or range of analyte concentrations). As shown for example by the data presented in FIG. 5, such this selection can be performed with minimal experimentation using the disclosed values as controls.

In another illustrative embodiment of the invention, the processor is capable of characterizing a plurality of signals received from the sensor by for example comparing a first signal received from a working electrode coated with glucose oxidase with a second signal received from a working electrode not coated with glucose oxidase so as to obtain information on a background signal that is not based on a sensed physiological characteristic value in the mammal. In another illustrative embodiment of the invention, the processor is capable of characterizing a plurality of signals received from the sensor by comparing a first signal received from a working electrode coated with glucose oxidase with a second signal received from a working electrode not coated with glucose oxidase so as to obtain information on a signal generated by an interfering compound. In another embodiment of the invention, two working electrodes are coated with glucose oxidase and the processor is capable of obtaining information on glucose concentrations in the mammal by comparing the signals received from the two working electrodes coated with glucose oxidase.

Certain sensor embodiments that switch between a high potential to a low potential (e.g. with a frequency of less than 3, 2 or 1 seconds). In such embodiments, a sensor may not discharge, with for example sensor elements acting as a sort of capacitor. In this context, some embodiments of the invention can include a circuit discharge element that facilitates sensor circuit discharge (e.g. if discharge is not sufficient to reach a specific potential such as 535 millivolts). A variety of such circuit discharge elements known in the art can be adapted for use with sensor embodiments of the invention (see, e.g. U.S. Pat. Nos. 4,114,627; 4,373,531; 4,858,610; 4,991,583; and 5,170,806, 5,486,201, 6,661,275 and U.S. Patent Application No. 20060195148). Optionally for example, a sensor charge can be removed by connecting it through a discharging switch element, and optionally a discharging resistor element.

Figure 14:
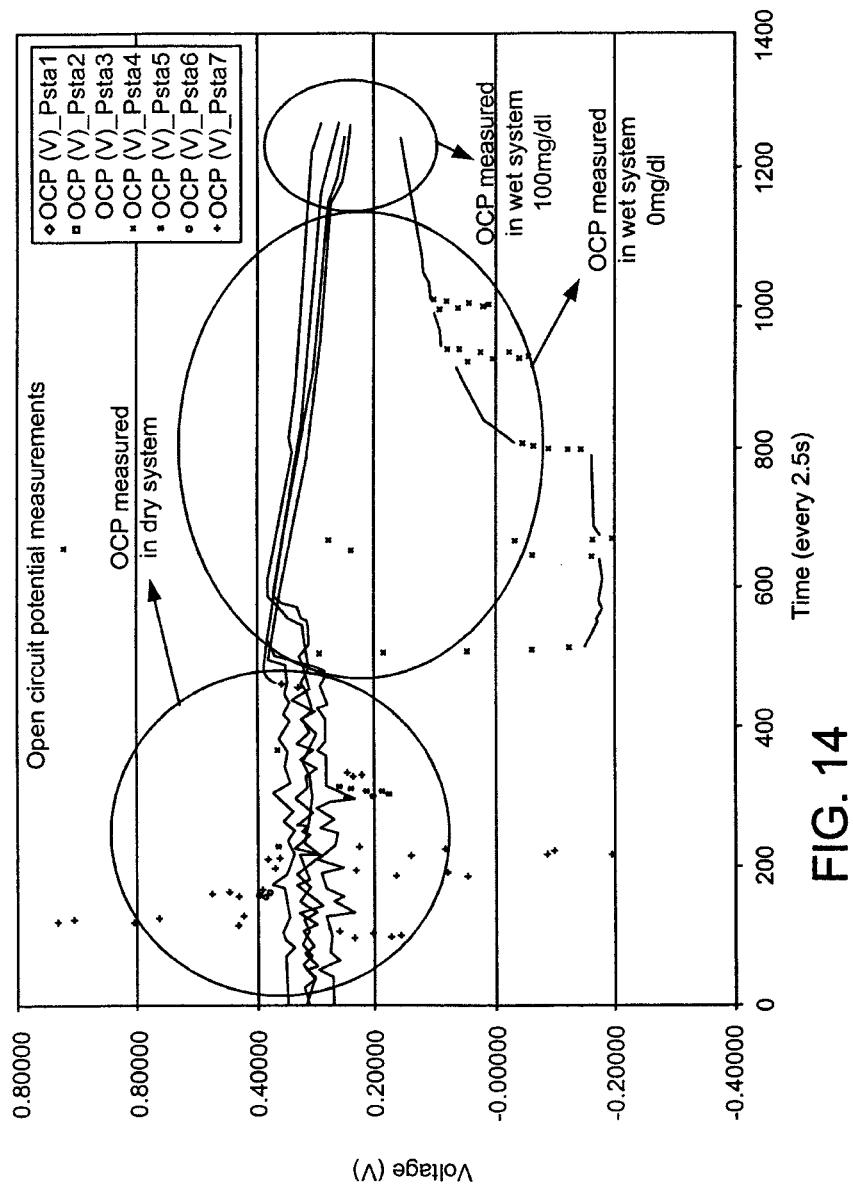
FIG. 14 shows graphical data from seven sensors which demonstrates how an open circuit potential (OCP) is a good indicator of when sensors reach a state of hydration sufficient for initialization. In these studies, the point of 280 mV was chosen as the optimal operating potential to detect glucose and eliminate the acetaminophen effect. A group of sensors was tested with the operating potential set at 280 mV and compared to a control group set at 535 mV. Seven (7) sensors were inserted into an empty bicarbonate buffer system and set at the following parameters: two (2) sensors to have the Open Circuit Potential (OCP) measured for in a dry system for ~430 s followed by OCP measured in a wet system at 0 mg/dl for ~600 s followed by OCP measured in a wet system at 100 mg/dl. After the OCP measurements were made, a triple Initialization scheme was applied. After the triple initiation was complete, the sensors were then run at 535 mV for ~100 ks. In five (5) sensors, the Open Circuit Potential (OCP) was measured for in a dry system for ~430 s followed by OCP measured in a wet system at 0 mg/dl for ~600 s followed by OCP measured in a wet system at 100 mg/dl. After the OCP measurements were made, the triple initialization scheme was applied. After the triple initialization was complete, the sensors were to run at 280 mV for ~100 ks.

Certain embodiments of the invention include a processor that detects whether a sensor is sufficiently hydrated for analyte detection comprising a computer usable media including at least one computer program embedded therein that is capable of calculating an impedance value; and comparing the impedance value against a threshold to determine if the sensor is sufficiently hydrated for analyte detection. A related embodiment of the invention is a method of detecting whether a sensor is sufficiently hydrated for analyte detection, comprising calculating an open circuit potential value between at least two electrodes of the sensor; and comparing the open circuit potential value against a threshold to determine if the sensor sufficiently hydrated for analyte detection. Typically, the open circuit potential value is the impedance value (and optionally this value is an approximation of a sum of polarization resistance and solution resistance). Optionally, the open circuit potential value is compared against an another threshold to determine if the sensor sufficiently hydrated for analyte detection. This can solve problems that occur when a user attempts to initialize a sensor that is not fully hydrated (e.g. compromising the accuracy and/or lifetime of the sensor). FIG. 14 shows graphical data from seven sensors which demonstrates that an open circuit potential (OCP) is a good indicator of when sensors reach a state of hydration sufficient for initialization.

Certain embodiments of the invention include materials that facilitate the use of glucose oxidase, by for example, incorporating materials that function to optimize the stoichiometry of a reaction of interest (e.g. to overcome the oxygen deficit problem). Optionally for example, the analyte sensing layer comprises an oxidoreductase that generates hydrogen peroxide upon exposure to a ligand for the oxidoreductase, wherein the amount of hydrogen peroxide generated by the polypeptide is proportional to the amount of ligand exposed to the polypeptide. Typically, the oxidoreductase polypeptide comprises an enzyme selected from the group consisting of glucose oxidase, glucose dehydrogenase, lactate oxidase, hexokinase and lactose dehydrogenase. Optionally, the analyte sensing layer comprises an oxidoreductase polypeptide crosslinked to a carrier polypeptide by a crosslinking compound having the formula: $L_1$-$CH_2$—($CH_2$—O—$CH_2$)$_n$—$CH_2$-$L_2$, wherein L1 and L2 comprise N-Hydroxysuccinimide (e.g. N-Hydroxysuccinimide moieties that covalently bond to amine moieties on the oxidoreductase polypeptide and the carrier polypeptide) or pentafluorophenyl moieties and n is equal to 5, 6, 7, 8, 9 or 10. In certain embodiments of the invention, the crosslinking compound is bis N-succinimidyl-[pentaethylene glycol]ester comprising polyethylene glycol moieties so as to make the analyte sensing layer with more flexible and hydrophilic than a crosslinking compound that does not contain polyethylene glycol moieties. Related embodiments of the invention include methods for using such a crosslinking compound to inhibit sensor layer cracking and/or delamination and/or to facilitate the hydration and/or stoichiometry of a chemical reaction of the various sensor embodiments of the invention. Another related embodiment of the invention is a method of forming an analyte sensing layer on a metallic electrode surface formed by an electrodeposition process, the method comprising the steps of: disposing a composition comprising an oxidoreductase polypeptide and a carrier polypeptide on to the metallic electrode surface; crosslinking the oxidoreductase polypeptide and the carrier polypeptide with a crosslinking compound having the formula: $L_1$-$CH_2$—($CH_2$—O—$CH_2$)$_n$—$CH_2$-$L_2$; and then crosslinking the oxidoreductase polypeptide and the carrier polypeptide with a glutaraldehyde composition.

As noted above, it has been discovered that certain crosslinking reagents can be used for example to produce crosslinked polypeptide layers having a constellation of structural and chemical properties that make them surprisingly useful in certain contexts (e.g. when used to crosslink carrier proteins such albumin and enzymes such as glucose oxidase within a layer of a sensor apparatus having a plurality of overlapping functional layers). As is known in the art, crosslinking is the process of chemically joining two or more molecules by a covalent bond. Crosslinking compounds typically comprise a linker "arm" that functions as a tether between crosslinked compounds as well as at least two chemical moieties (typically on distal ends of the arm of the compound) that react specific functional groups on proteins or other molecules (see, e.g. primary amines, sulfhydryls and the like). As discussed in detail below, a variety of crosslinking agents are known and commercially available from suppliers such as Pierce Biotechnology Inc., Rockford, Ill. (see, e.g. bis N-succinimidyl-[pentaethylene glycol]ester, Pierce Product No. 21581).

Crosslinkers can be either homobifunctional or heterobifunctional. Homobifunctional crosslinkers have two identical reactive groups and often are used in one-step reaction procedures to crosslink proteins to each other or to stabilize quaternary structure. Even when conjugation of two different proteins is the goal, one-step crosslinking with homobifunctional reagents can result in self-conjugation, intramolecular crosslinking and/or polymerization. Heterobifunctional crosslinkers possess two different reactive groups that can allow for sequential (two-stage) conjugations, which can for example help to minimize undesirable crosslinking reactions such as polymerization or self-conjugation. Heterobifunctional reagents can be used for example when modification of amines is problematic because for example, amines are sometimes present at the active sites of proteins and modification of these may lead to activity loss. Other moieties such as sulfhydryls, carboxyls, phenols and carbohydrates may be more appropriate targets.

Two-step (i.e. sequential) crosslinking strategies in this context can allows a protein that can tolerate the modification of its amines to be coupled to a protein or other molecule having different accessible groups. In sequential crosslinking procedures, heterobifunctional reagents can be reacted with one protein using the most labile group of the crosslinker first. After removing excess nonreacted crosslinker, the modified first protein is added to a solution containing the second protein where reaction through the second reactive group of the crosslinker occurs. Commonly used heterobifunctional crosslinkers include those having an amine-reactive succinimidyl ester (i.e., NHS-ester) at one end and a sulfhydryl reactive group on the other end. The sulfhydryl-reactive groups are usually maleimides, pyridyl disulfides and α-haloacetyls. The NHS-ester reactivity is less stable in aqueous solution and is usually reacted first in sequential crosslinking procedures. NHS-esters react with amines to form amide bonds.

Carbodiimides are zero-length crosslinkers (see, e.g., EDC, Pierce Product #22980, 22981) and effect direct coupling between carboxylates (—COOH) and primary amines (—NH2) and have been used in protein-protein conjugation. Other heterobifunctional reagents include those compounds having one reactive group that is photoreactive rather than thermoreactive. These compounds can have advantages in protein:protein interaction studies and in cases where the availability of thermoreactive targetable functional groups is unknown. This reactivity allows for specific attachment of the labile thermoreactive group first; subsequently, conjugation to any adjacent N—H or C—H sites may be initiated through the photoreactive group by activation with UV light. The reactivity of the photochemical reagent allows for formation of a conjugate that may not be possible with a group-specific reagent.

Crosslinkers for use in a particular context can be selected on the basis of their chemical reactivities (i.e., specificity for particular functional groups) as well as their compatibility of the reaction with the application (see, e.g. crosslinking a functional glucose oxidase polypeptide with an albumin polypeptide). The specific crosslinker to use in a specific application can be determined empirically. However, crosslinkers can be selected due to previously characterized properties such as one or more of the following: chemical specificity; spacer arm length; reagent water-solubility and cell membrane permeability; same (homobifunctional) or different (heterobifunctional) reactive groups; thermoreactive or photoreactive groups; whether the reagent crosslinks are cleavable or not; whether the reagent contains moieties that can be radiolabeled or tagged with another label.

Illustrative crosslinking compounds include N-Hydroxysuccinimide-Esters (NHS-Esters). NHS-esters yield stable products upon reaction with primary amines with relatively efficient coupling at physiological pH. Accessible α-amine groups present on the N-termini of proteins and e-amines on lysine residues react with NHS-esters and form amide bonds. A covalent amide bond is formed when the NHS-ester crosslinking agent reacts with a primary amine, releasing N-hydroxysuccinimide. Hydrolysis of the NHS-ester competes with the primary amine reaction. Hydrolysis rate increases with increasing pH and occurs more readily in dilute protein solutions. Studies performed on NHS ester compounds indicate the half-life of hydrolysis for a homobifunctional NHS-ester is 4-5 hours at pH 7.0 and 0° C. in aqueous environments free of primary amines. This half-life decreases to 10 minutes at pH 8.6 and 4° C. The extent of the NHS-ester hydrolysis in aqueous solutions free of primary amines may be measured at 260 nm. An increase in absorbance at this wavelength is caused by the release of NHS. The molar extinction coefficient of NHS released by hydrolysis and reaction with a nucleophile is 8.2×103 M-1 cm-1 at 260 nm at pH 9.0. The molar extinction coefficient for the NHS-ester in 50 mM potassium phosphate buffer, pH 6.5 is 7.5×103 M-1 cm-1 at 260 nm.

NHS-ester crosslinking reactions are most commonly performed in phosphate, bicarbonate/carbonate, HEPES or borate buffers at concentrations between 50-200 mM. Other buffers may also be used if they do not contain primary amines. HEPES, for example, can be used because it contains only tertiary amines. Primary amines are present in the structure of Tris, which makes it an unacceptable buffer for NHS-ester reactions. A large excess of Tris at neutral-to-basic pH may be added at the end of a NHS-ester reaction to quench it. Glycine also contains a primary amine and may be used in a similar manner. The NHS-ester reactions are typically performed between pH 7 and 9 and at 4° C. to room temperature from 30 minutes to 2 hours. Reaction times at 4° C. are increased 4-fold from room temperature incubation times to produce similar efficiencies. NHS-esters are usually used at 2- to 50-fold molar excess to protein depending on the concentration of the protein. Typically, the concentration of the crosslinker can vary from 0.1-10 mM. The protein concentration should typically be kept above 10 µM (50-100 µM is optimal) because more dilute protein solutions result in excessive hydrolysis of the crosslinker.

NHS-esters can be grouped into two separate classes with essentially identical reactivity toward primary amines: solvent carryover of 0.5-10% final volume in the aqueous reaction. The results of crosslinking with a NHS-esters can be unpredictable because for example, in some cases, cross-linking proteins with NHS-esters may result in loss of biological activity that may be a result of conformational change of the protein when the NHS-ester crosslinker reacts with primary amines on the molecule's surface. The disclosure provided herein shows that this does not occur with the oxidoreductase glucose oxidase. The effects of crosslinkers on other oxidoreductases can be determined with only minimal experimentation.

One illustrative N-Hydroxysuccinimide-Ester that can be used in embodiments of the invention is Bis(NHS)PEO$_5$ [Bis N-Succinimidyl-(pentaethylene glycol) ester] (see, e.g. Pierce Product #21581). This N-Hydroxysuccinimide-Ester is a homobifunctional, amine-reactive, water soluble, non-cleavable crosslinking agent having a polyethylene oxide (PEO) spacer. Bis(NHS)PEO$_5$ is an analog of crosslinker BS$^3$ (see, e.g. Pierce Product #21580), which is also water-soluble with the aqueous solubility being contributed primarily by the sulfo-NHS ester groups. However, BS$^3$ contains a hydrophobic suberic acid-containing spacer. The crosslinked products produced from reaction with Bis(NHS)PEO$_5$ inserts a pentaethylene glycol spacer into the molecule that aids in maintaining the solubility of the crosslinked complex. Table 1 below provides a summary of properties of Bis(NHS)PEO$_5$ [Bis N-Succinimidyl-(pentaethylene glycol) ester].

TABLE 1

Bis(NHS)PEO$_5$ [Bis N-Succinimidyl-(pentaethylene glycol) ester]

Properties:

| | |
|---|---|
| Alternate names: | Bis-dPEG-NHS ester, Bis-NHS-PEO and Bis(NHS)dPEG$_5$ |
| Molecular formula: | $C_{22}H_{32}O_{13}N_2$ |
| Molecular weight: | 532.50 |
| Spacer arm length: | 21.7 Å |
| Mass added to target: | Single link with NHS hydrolysis: 320.15; Complete crosslink: 302.13 |
| Physical form: | viscous liquid |
| Solvent compatibility: | DMSO, methylene chloride |
| Storage conditions: | Store desiccated at −20° C., protect from moisture, use fresh solutions only |
| Reactive groups: | NHS ester, reacts with primary amines at pH 7.0-9.0 |
| Spacer arm composition: | Polyethylene oxide (PEO)/5 ethylene oxide subunits | water-soluble and water-insoluble. Water-soluble NHS-esters have a sulfonate (—SO3) group on the N-hydroxysuccinimide ring. They are advantageous when the presence of organic solvents cannot be tolerated. The reaction with the sulfo-NHS-esters is usually performed in 100% aqueous solutions; however, it is possible to achieve greater solubility when the reagent is dissolved in organic solvents such as DMSO (Product #20688). The water-soluble NHS-ester crosslinkers are used for cell surface conjugation because they will not permeate the membrane. Sulfonated NHS-ester crosslinkers are supplied as sodium salts and are soluble in water to a concentration of at least 10 mM. The solubility of the NHS-esters will typically vary with buffer composition. The non-sulfonated forms of NHS-ester reagents are water-insoluble and are first dissolved in water-miscible organic solvent, such as DMSO (see, e.g. Pierce Product #20688) and DMF (see, e.g. Pierce Product N #20672), then added to the aqueous reaction mixture. The water-insoluble crosslinkers do not possess a charged group and are lipophilic and membrane-permeable. Crosslinking reactions with the water-insoluble NHS-esters are typically performed with a With molecules such as Bis(NHS)PEO$_5$ [Bis N-Succinimidyl-(pentaethylene glycol) ester, the use of polyethylene oxide, also referred to as polyethylene glycol (PEG), as a spacer separating the reactive groups, can impart specific advantages to the resulting crosslinked protein(s), conjugates or interacting complexes in certain contexts (see, e.g. when used to link enzymes such as glucose oxidase that are disposed within a layer of a sensor apparatus having a plurality of overlapping functional layers).

As noted above, embodiments of the invention include methods for making the sensor embodiments disclosed herein. Certain methods for making the sensor embodiments disclosed herein include the step of precisely controlling the concentration of a constituent so as to effect its morphology, function or the like. For example in sensors that use $GO_x$, a concentration range of about 20-40 KU (and 5% Human Serum Albumin) can be used to optimize $GO_x$ layer morphology. Methods for making the sensor embodiments disclosed herein include the step of applying an oxidoreductase (e.g. a $GO_x$ composition) onto the surface of an electrode via brushing methods that facilitate its disposal in proximity to reactive surface. In this context, brushing (e.g. with the equivalent of a tiny paintbrush) $GO_x$ onto electrode surface and/or writing $GO_x$ onto electrode surface using a pen-type device can be employed rather than depositing a droplet of the solution, a procedure which (e.g. due to surface tension of droplet) can produce uneven deposition. Moreover, such brushing steps can push a composition solution deep into the convoluted reactive surface of a Pt black of electrode. In addition, brushing is easier than processes such as spin coating because it allows for a more precise localized deposition of a composition. In this context, brushing allows for example, the easy coating of small reactive surfaces that are not amenable to coating by other means (e.g. pipetting and/or spin coating processes). Certain embodiments for making the invention can be performed under a vacuum to, for example, pull out air and facilitate application of a layer to a substrate.

Certain embodiments for making the invention include the step of performing a crosslinking reaction under a vacuum to pull out air and facilitate application. One such embodiment of the invention is a method of making an analyte sensor apparatus comprising: an elongated base layer; a conductive layer disposed on the base layer and comprising a reference electrode, a working electrode and a counter electrode; an analyte sensing layer disposed on the conductive layer; an analyte modulating layer disposed on the analyte sensing layer, wherein the analyte modulating layer comprises a composition that modulates the diffusion of an analyte diffusing through the analyte modulating layer; and a cover layer disposed on the analyte sensor apparatus, wherein the cover layer comprises an aperture positioned on the cover layer so as to facilitate an analyte contacting and diffusing through the analyte modulating layer and contacting the analyte sensing layer.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users (e.g. a diabetic performing daily activities). Alternatively, the sensor can be designed for use in stationary contexts such as those adapted for use in clinical settings. Such sensor embodiments include, for example, those used to monitor one or more analytes present in one or more physiological environments in a hospitalized patient (e.g. a patient confined to a hospital bed in situations such as those described in WO 2008042625).

Sensors of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example, in such implanted oxygen sensor apparatus designs, oxygen noise at the reference sensor can compromise the signal to noise ratio which consequently perturbs their ability to obtain stable glucose readings in this environment. The sensors of the invention therefore overcome the difficulties observed with such oxygen sensors in non-vascular regions.

Certain sensor embodiments of the invention further include advantageous long term or "permanent" sensors which are suitable for implantation in a mammal for a time period of greater than 30 days. In particular, as is known in the art (see, e.g. ISO 10993, Biological Evaluation of Medical Devices) medical devices such as the sensors described herein can be categorized into three groups based on implant duration: (1) "Limited" (<24 hours), (2) "Prolonged" (24 hours-30 days), and (3) "Permanent" (>30 days). In some embodiments of the invention, the design of the peroxide sensor of the invention allows for a "Permanent" implantation according to this categorization, i.e. >30 days. In related embodiments of the invention, the highly stable design of the peroxide sensor of the invention allows for an implanted sensor to continue to function in this regard for 2, 3, 4, 5, 6 or 12 or more months.

Typically, the analyte sensor apparatus includes an analyte sensing layer disposed on a conductive layer of the sensor, typically covering a portion or all of the working electrode. This analyte sensing layer detectably alters the electrical current at the working electrode in the conductive layer in the presence of an analyte to be sensed. As disclosed herein, this analyte sensing layer typically includes an enzyme or antibody molecule or the like that reacts with the analyte of interest in a manner that changes the concentrations of a molecule that can modulate the current at the working electrode (see e.g. oxygen and/or hydrogen peroxide as shown in the reaction scheme of FIG. 1). Illustrative analyte sensing layers comprise an enzyme such as glucose oxidase (e.g. for use in glucose sensors) or lactate oxidase (e.g. for use in lactate sensors). In some embodiments of the invention, the analyte sensing layer is disposed upon a porous metallic and/or ceramic and/or polymeric matrix with this combination of elements functioning as an electrode in the sensor. In certain embodiments of the invention that require a robust design (e.g. long-term sensors), a ceramic base is used as a dielectric (rather than a polyimide) due to its relatively stronger material properties.

Typically, the analyte-sensing layer further comprises a carrier protein in a substantially fixed ratio with the analyte sensing compound (e.g. the enzyme) and the analyte sensing compound and the carrier protein are distributed in a substantially uniform manner throughout the analyte sensing layer. Typically the analyte sensing layer is very thin, for example, less than 1, 0.5, 0.25 or 0.1 microns in thickness. While not being bound by a specific scientific theory, it is believed that sensors having such thin analyte sensing layers have surprisingly enhanced characteristics as compared to the thicker layers that are typically generated by electrodeposition because electrodeposition produces 3-5 micron thick enzyme layers in which only a fraction of the reactive enzyme within the coating layer is able to access the analyte to be sensed. Such thicker glucose oxidase pellets that are produced by electrodeposition protocols are further observed to have a poor mechanical stability (e.g. a tendency to crack) and further take a longer time to prepare for actual use, typically taking weeks of testing before it is ready for implantation. As these problems are not observed with the thin layered enzyme coatings described herein, these thin coatings are typical embodiments of the invention.

Optionally, the analyte sensing layer has a protein layer disposed thereon and which is typically between this analyte sensing layer and the analyte modulating layer. A protein within the protein layer is an albumin selected from the group consisting of bovine serum albumin and human serum albumin. Typically this protein is crosslinked. Without being bound by a specific scientific theory, it is believed that this separate protein layer enhances sensor function and provides surprising functional benefits by acting as a sort of capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme such as $GO_x$ from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Typically, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer. This adhesion promoting layer typically comprises a silane compound such as γ-aminopropyltrimethoxysilane which is selected for its ability to promote optimized adhesion between the various sensor layers and functions to stabilize the sensor. Interestingly, sensors having such a silane containing adhesion promoting layers exhibit unexpected properties including an enhanced overall stability. In addition, silane containing adhesion promoting layers provide a number of advantageous characteristics in addition to an ability to enhancing sensor stability, and can, for example, play a beneficial role in interference rejection as well as in controlling the mass transfer of one or more desired analytes.

In certain embodiments of the invention, the adhesion promoting layer further comprises one or more compounds that can also be present in an adjacent layer such as the polydimethyl siloxane (PDMS) compounds that serves to limit the diffusion of analytes such as glucose through the analyte modulating layer. The addition of PDMS to the AP layer for example can be advantageous in contexts where it diminishes the possibility of holes or gaps occurring in the AP layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serve to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) comprising a polymer such as polydimethyl siloxane or the like. In certain embodiments of the invention, the analyte modulating layer comprises a hydrophilic comb-copolymer having a central chain and a plurality of side chains coupled to the central chain, wherein at least one side chain comprises a silicone moiety.

Typically the analyte modulating layer further comprises one or more cover layers which are typically electrically insulating protective layers disposed on at least a portion of the sensor apparatus (e.g. covering the analyte modulating layer). Acceptable polymer coatings for use as the insulating protective cover layer can include, but are not limited to, non-toxic biocompatible polymers such as silicone compounds, polyimides, biocompatible solder masks, epoxy acrylate copolymers, or the like. An illustrative cover layer comprises spun on silicone. Typically the cover layer further includes an aperture that exposes at least a portion of a sensor layer (e.g. analyte modulating layer) to a solution comprising the analyte to be sensed.

The analyte sensors described herein can be polarized cathodically to detect, for example, changes in current at the working cathode that result from the changes in oxygen concentration proximal to the working cathode that occur as glucose interacts with glucose oxidase as shown in FIG. 1. Alternatively, the analyte sensors described herein can be polarized anodically to detect for example, changes in current at the working anode that result from the changes in hydrogen peroxide concentration proximal to the working anode that occur as glucose interacts with glucose oxidase as shown in FIG. 1. In typical embodiments of the invention, the current at the working electrode(s) is compared to the current at a reference electrode(s) (a control), with the differences between these measurements providing a value that can then be correlated to the concentration of the analyte being measured. Analyte sensor designs that obtain a current value by obtaining a measurement from a comparison of the currents at these dual electrodes are commonly termed, for example, dual oxygen sensors.

In some embodiments of the invention, the analyte sensor apparatus is designed to function via anodic polarization such that the alteration in current is detected at the anodic working electrode in the conductive layer of the analyte sensor apparatus. Structural design features that can be associated with anodic polarization include designing an appropriate sensor configuration comprising a working electrode which is an anode, a counter electrode which is a cathode and a reference electrode, and then selectively disposing the appropriate analyte sensing layer on the appropriate portion of the surface of the anode within this design configuration. Optionally this anodic polarization structural design includes anodes, cathodes and/or working electrodes having different sized surface areas. For example, this structural design includes features where the working electrode (anode) and/or the coated surface of the working electrode is larger or smaller than the counter electrode (cathode) and/or the coated surface of the counter electrode (e.g. a sensor designed to have a 1× area for a reference electrode, a 2.6× area for a working electrode and a 3.6× area for a counter electrode). In this context, the alteration in current that can be detected at the anodic working electrode is then correlated with the concentration of the analyte. In certain illustrative examples of this embodiment of the invention, the working electrode is measuring and utilizing hydrogen peroxide in the oxidation reaction (see e.g. FIG. 1), hydrogen peroxide that is produced by an enzyme such as glucose oxidase or lactate oxidase upon reaction with glucose or lactate respectively. Such embodiments of the invention relating to electrochemical glucose and/or lactate sensors having such hydrogen peroxide recycling capabilities are particularly interesting because the recycling of this molecule reduces the amount of hydrogen peroxide that can escape from the sensor into the environment in which it is placed. In this context, implantable sensors that are designed to reduce the release of tissue irritants such as hydrogen peroxide will have improved biocompatibility profiles. Moreover as it is observed that hydrogen peroxide can react with enzymes such as glucose oxidase and compromise their biological function, such sensors are desired due to their avoidance of this phenomena. Optionally, the analyte modulating layer (e.g. a glucose limiting layer) can include compositions that serve to inhibit the diffusion of hydrogen peroxide out into the environment in which the sensor is placed. Consequently, such embodiments of the invention improve the biocompatibility of sensors that incorporate enzymes that produce hydrogen peroxide by incorporating hydrogen peroxide recycling elements disclosed herein.

E. Permutations of Analyte Sensor Apparatus and Elements

The disclosure provided above allows artisans to generate a variety of embodiments of the analyte sensor apparatus disclosed herein. As noted above, illustrative general embodiments of the sensor disclosed herein include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 2 illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

An illustrative embodiment of the invention is shown in FIG. 2. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In an illustrative embodiment as shown in FIG. 2 the analyte sensing layer comprises a conductive layer 104 which is disposed on insulating base layer 102. Typically the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, non-toxic biocompatible polymers such as polyimide, biocompatible solder masks, epoxy acrylate copolymers, or the like. Further, these coatings can be photo-imageable to facilitate photolithographic forming of apertures 108 through to the conductive layer 104. In certain embodiments of the invention, an analyte sensing layer is disposed upon a porous metallic and/or ceramic and/or polymeric matrix with this combination of elements functioning as an electrode in the sensor.

In the sensors of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photoresist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize a separate reference element not formed on the sensor. The exposed electrodes and/or contact pads can also undergo secondary processing through the apertures 108, such as additional plating processing, to prepare the surfaces and/or strengthen the conductive regions.

An analyte sensing layer 110 is typically disposed on one or more of the exposed electrodes of the conductive layer 104 through the apertures 108. Typically, the analyte sensing layer 110 is a sensor chemistry layer and most typically an enzyme layer. Typically, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The analyte sensing layer 110 can be applied over portions of the conductive layer or over the entire region of the conductive layer. Typically the analyte sensing layer 110 is disposed on portions of a working electrode and a counter electrode that comprise a conductive layer. Some methods for generating the thin analyte sensing layer 110 include spin coating processes, dip and dry processes, low shear spraying processes, ink-jet printing processes, silk screen processes and the like. Most typically the thin analyte sensing layer 110 is applied using a spin coating process.

The analyte sensing layer 110 is typically coated with one or more coating layers. In some embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art. In certain embodiments of the invention, the analyte modulating layer comprises a hydrophilic comb-copolymer having a central chain and a plurality of side chains coupled to the central chain, wherein at least one side chain comprises a silicone moiety.

In some embodiments of the invention, a coating layer is a glucose limiting membrane layer 112 which is disposed above the analyte sensing layer 110 to regulate glucose contact with the analyte sensing layer 110. In some embodiments of the invention, an adhesion promoter layer 114 is disposed between the membrane layer 112 and the analyte sensing layer 110 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the membrane layer 112 to be disposed in direct contact with the analyte sensing layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more typically substantially all of a surface of the sensor, and that is capable of interacting with one or more analytes, such as chemical compounds, cells and fragments thereof, etc., in the environment in which the sensor is disposed. Non-limiting examples of functional coating layers include analyte sensing layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including an UV-absorbing polymer. In some embodiments, the UV-absorbing polymer is a polyurethane, a polyurea or a polyurethane/polyurea copolymer. More typically, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; U.S. Pat. No. 5,165, 407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming an UV-absorbing polymer layer above or below a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensors of the present invention are particularly designed for use as subcutaneous or transcutaneous glucose sensors for monitoring blood glucose levels in a diabetic patient. Typically each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

The sensors of the invention can have any desired configuration, for example planar or cylindrical. The base layer 102 can be self-supportive, such as a rigid polymeric layer, or non-self supportive, such as a flexible film. The latter embodiment is desirable in that it permits continuous manufacture of sensors using, for example, a roll of a polymeric film which is continuously unwound and upon which sensor elements and coating layers are continuously applied.

A general embodiment of the invention is a sensor designed for implantation within a body that comprises a base layer, an analyte sensing layer disposed upon the base layer which includes a plurality of sensor elements, an enzyme layer (typically less than 2 microns in thickness) disposed upon the analyte sensing layer which coats all of the plurality of sensing elements on the conductive layer, and one or more coating layers. Typically the enzyme layer comprises glucose oxidase; typically in a substantially fixed ratio with a carrier protein. In a specific embodiment, the glucose oxidase and the carrier protein are distributed in a substantially uniform manner throughout the disposed enzyme layer. Typically the carrier protein comprises albumin, typically in an amount of about 5% by weight. As used herein, "albumin" refers to those albumin proteins typically used by artisans to stabilize polypeptide compositions such as human serum albumin, bovine serum albumin and the like. In some embodiments of the invention, a coating layer is an analyte contacting layer which is disposed on the sensor so as to regulate the amount of analyte that can contact the enzyme layer. In further embodiments, the sensor includes an adhesion promoter layer disposed between the enzyme layer and the analyte contacting layer; and, the enzyme layer is less than 1, 0.5, 0.25 or 0.1 microns in thickness.

F. Analyte Sensor Apparatus Configurations

In a clinical setting, accurate and relatively fast determinations of analytes such as glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference. As noted below, embodiments of the invention disclosed herein have a wider range of geometrical configurations (e.g. planar) than existing sensors in the art. In addition, certain embodiments of the invention include one or more of the sensors disclosed herein coupled to another apparatus such as a medication infusion pump.

FIG. 2 provides a diagrammatic view of a typical thin layer analyte sensor configuration of the current invention. FIG. 3 provides a diagrammatic view of a typical thin layer analyte sensor system of the current invention. Certain sensor configurations are of a relatively flat "ribbon" type configuration that can be made with the analyte sensor apparatus. Such "ribbon" type configurations illustrate an advantage of the sensors disclosed herein that arises due to the spin coating of sensing enzymes such as glucose oxidase, a manufacturing step that produces extremely thin enzyme coatings that allow for the design and production of highly flexible sensor geometries. Such thin enzyme coated sensors provide further advantages such as allowing for a smaller sensor area while maintaining sensor sensitivity, a highly desirable feature for implantable devices (e.g. smaller devices are easier to implant). Consequently, sensor embodiments of the invention that utilize very thin analyte sensing layers that can be formed by processes such as spin coating can have a wider range of geometrical configurations (e.g. planar) than those sensors that utilize enzyme layers formed via processes such as electrodeposition.

Certain sensor configurations include multiple conductive elements such as multiple working, counter and reference electrodes. Advantages of such configurations include increased surface area which provides for greater sensor sensitivity. For example, one sensor configuration introduces a third working sensor. One obvious advantage of such a configuration is signal averaging of three sensors which increases sensor accuracy. Other advantages include the ability to measure multiple analytes. In particular, analyte sensor configurations that include electrodes in this arrangement (e.g. multiple working, counter and reference electrodes) can be incorporated into multiple analyte sensors. The measurement of multiple analytes such as oxygen, hydrogen peroxide, glucose, lactate, potassium, calcium, and any other physiologically relevant substance/analyte provides a number of advantages, for example the ability of such sensors to provide a linear response as well as ease in calibration and/or recalibration.

An exemplary multiple sensor device comprises a single device having a first sensor which is polarized cathodically and designed to measure the changes in oxygen concentration that occur at the working electrode (a cathode) as a result of glucose interacting with glucose oxidase; and a second sensor which is polarized anodically and designed to measure changes in hydrogen peroxide concentration that occurs at the working electrode (an anode) as a result of glucose coming form the external environment and interacting with glucose oxidase. As is known in the art, in such designs, the first oxygen sensor will typically experience a decrease in current at the working electrode as oxygen contacts the sensor while the second hydrogen peroxide sensor will typically experience an increase in current at the working electrode as the hydrogen peroxide generated as shown in FIG. 1 contacts the sensor. In addition, as is known in the art, an observation of the change in current that occurs at the working electrodes as compared to the reference electrodes in the respective sensor systems correlates to the change in concentration of the oxygen and hydrogen peroxide molecules which can then be correlated to the concentration of the glucose in the external environment (e.g. the body of the mammal).

The analyte sensors of the invention can be coupled with other medical devices such as medication infusion pumps. In an illustrative variation of this scheme, replaceable analyte sensors of the invention can be coupled with other medical devices such as medication infusion pumps, for example by the use of a port couple to the medical device (e.g. a subcutaneous port with a locking electrical connection).

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

B. Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a analyte sensing enzyme layer can then be disposed on the sensing layer by electrochemical deposition or a method other than electrochemical deposition such a spin coating, followed by vapor crosslinking, for example with a dialdehyde (glutaraldehyde) or a carbodiimide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Subsequent to treatment of the sensor elements, one or more additional functional coatings or cover layers can then be applied by any one of a wide variety of methods known in the art, such as spraying, dipping, etc. Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as exact the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt %. Among the copolymers listed above, the dimethylsiloxane-bisphenol A carbonate copolymer which comprises 50-55 wt % of the nonsiloxane component is typical. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane non-siloxane copolymer, where compatible.

In some embodiments of the invention, the sensor is made by methods which apply an analyte modulating layer that comprises a hydrophilic membrane coating which can regulate the amount of analyte that can contact the enzyme of the sensor layer. For example, the cover layer that is added to the glucose sensors of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic comb-copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate the contact between the hydrogen peroxide molecules and the electrode sensing elements.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrimethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

Like certain other coating layers of the sensor, the adhesion promoter layer can be subjected to one or more suitable radiation and/or chemical and/or heat curing steps as are known in the art. In alternative embodiments, the enzyme layer can be sufficiently crosslinked or otherwise prepared to allow the membrane cover layer to be disposed in direct contact with the analyte sensing layer in the absence of an adhesion promoter layer.

An illustrative embodiment of the invention is a method of making a sensor by providing a base layer, forming a sensor layer on the base layer, spin coating an enzyme layer on the sensor layer and then forming an analyte contacting layer (e.g. an analyte modulating layer such as a glucose limiting membrane) on the sensor, wherein the analyte contacting layer regulates the amount of analyte that can contact the enzyme layer. In some methods, the enzyme layer is vapor crosslinked on the sensor layer. In a typical embodiment of the invention, the sensor layer is formed to include at least one working electrode and at least one counter electrode. In certain embodiments, the enzyme layer is formed on at least a portion of the working electrode and at least a portion of the counter electrode. Typically, the enzyme layer that is formed on the sensor layer is less than 2, 1, 0.5, 0.25 or 0.1 microns in thickness. Typically, the enzyme layer comprises one or more enzymes such as glucose oxidase, glucose dehydrogenase, lactate oxidase, hexokinase or lactate dehydrogenase and/or like enzymes. In a specific method, the enzyme layer comprises glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, the adhesion promoter layer is subjected to a curing process prior to the formation of the analyte contacting layer.

A related embodiment of the invention is a method of making a glucose sensor by providing a base layer, forming a sensor layer on the base layer that includes at least one working electrode and at least one counter electrode, forming a glucose oxidase layer on the sensor layer by a spin coating process (a layer which is typically stabilized by combining the glucose oxidase with albumin in a fixed ratio), wherein the glucose oxidase layer coats at least a portion of the working electrode and at least a portion of the counter electrode, and then forming a glucose limiting layer on the glucose sensor so as to regulate the amount of glucose that can contact the glucose oxidase layer. In such processes, the glucose oxidase layer that is formed on the sensor layer is typically less than 2, 1, 0.5, 0.25 or 0.1 microns in thickness. Typically, the glucose oxidase coating is vapor crosslinked on the sensor layer. Optionally, the glucose oxidase coating covers the entire sensor layer. In certain embodiments of the invention, an adhesion promoter layer is disposed between the glucose oxidase layer and the analyte contacting layer. In certain embodiments of the invention, the analyte sensor further comprises one or more cover layers which are typically electrically insulating protective layers (see, e.g. element 106 in FIG. 2). Typically, such cover layers are disposed on at least a portion of the analyte modulating layer.

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. The functional coating layer(s) can be applied either before or after other sensor components are removed from the supporting substrate (e.g., by cutting).

III. Methods for Using Analyte Sensor Apparatus of the Invention

Related embodiments of the invention is a method of sensing an analyte within the body of a mammal, the method comprising implanting an analyte sensor embodiment disclosed herein in to the mammal and then sensing one or more electrical fluctuations such as alteration in current at the working electrode and correlating the alteration in current with the presence of the analyte, so that the analyte is sensed. Typically the analyte sensor is polarized anodically such that the working electrode where the alteration in current is sensed is an anode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds a porous matrix that is coated with a layer of an enzyme such as glucose oxidase. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

Various publication citations are referenced throughout the specification. In addition, certain text from related art is reproduced herein to more clearly delineate the various embodiments of the invention. The disclosures of all citations in the specification are expressly incorporated herein by reference.

The invention claimed is:

1. An apparatus for monitoring an analyte in a patient, the apparatus comprising:
a base adapted to secure the apparatus to the patient;
a first piercing member coupled to and extending from the base;
a first electrochemical sensor operatively coupled to the first piercing member, wherein the first electrochemical sensor comprises a plurality of working, counter and reference electrodes that are grouped together as a unit and positionally distributed in a repeating pattern of units;
a second piercing member coupled to and extending from the base;
a second electrochemical sensor operatively coupled to the second piercing member, wherein the second electrochemical sensor comprises a plurality of working, counter and reference electrodes that are grouped together as a unit and positionally distributed in a repeating pattern of units; and wherein:
the plurality of working electrodes, the plurality of counter electrodes and the plurality of references electrodes in the first electrochemical sensor and the second electrochemical sensor are clustered together in repeating units consisting essentially of one working electrode, one counter electrode and one reference electrode;
at least one physiological characteristic monitored by the first or the second electrochemical sensor comprises a concentration of a naturally occurring analyte in the patient;
the first and second piercing members are disposed on the base in a configuration selected so that the first piercing member disposes the first electrochemical sensor in a first tissue compartment of the patient and the second piercing member disposes the second electrochemical sensor in a second tissue compartment of the patient; and
the first and second piercing members are disposed on the base in a configuration selected to avoid a physiological response that can result from implantation of the first electrochemical sensor from altering a sensor signal generated by the second electrochemical sensor.

2. The apparatus of claim 1, further comprising:
a contact pad;
an electrical conduit which connects an electrochemical sensor electrode to an electrical connection element that is operatively coupled to the contact pad; and wherein:
the base comprises a flexible sensor substrate; and
the contact pad, the electrical conduit and the electrochemical sensor electrode are operatively coupled to the flexible sensor substrate in a configuration that allows the apparatus to function as it twists and bends in response to movement of implanted electrochemical sensors in the patient.

3. The apparatus of claim 2, wherein the apparatus comprises two contact pads connected to two electrical conduits and two sets of electrochemical sensor electrodes comprising a working, a counter and a reference electrode arranged such that:
the two contact pads are disposed together in a central region of the flexible sensor substrate so as to facilitate electrical connection to a power source and each of the two sets of electrochemical sensor electrodes is disposed on an opposite side of the flexible sensor substrate so as to maximize sensor separation;
the two contact pads are disposed together one side of the flexible sensor substrate so as to facilitate electrical connection to a power source and the two sets of electrochemical sensor electrodes are disposed together in a row on an opposite side of the flexible sensor substrate so as to provide a compact design for patient use; or
the two contact pads are disposed together one side of the flexible sensor substrate so as to facilitate electrical connection to a power source and the two sets of electrochemical sensor electrodes are disposed together in a staggered arrangement on an opposite side of the flexible sensor substrate so as to provide a compact design for patient use while providing a greater distance between each set of electrochemical sensor electrodes as compared to sensor electrodes not disposed together in a staggered arrangement.

4. The apparatus of claim 1, wherein at least one electrochemical sensor electrode comprises oxidoreductase that generates hydrogen peroxide upon exposure to a ligand for the oxidoreductase.

5. The apparatus of claim 4, wherein:
a working electrode in the first electrochemical sensor is coated with glucose oxidase; and
no working electrode in the second electrochemical sensor is coated with glucose oxidase.

6. The apparatus of claim 1, wherein the first and second electrochemical sensors are operatively coupled to a processor coupled to the sensor input, wherein the processor characterizes one or more signals received from the first and second electrochemical sensors.

7. The apparatus of claim 6, wherein the processor is capable of comparing a first signal received from a working electrode in response to a first working potential with a second signal received from a working electrode in response to a second working potential.

8. The apparatus of claim 7, wherein a pulsed voltage is used to obtain a signal from an electrode.

9. An apparatus for monitoring glucose in a patient, the apparatus comprising:
a base adapted to secure the apparatus to the patient;
a first piercing member coupled to and extending from the base element;
a first electrochemical sensor operatively coupled to the first piercing member, wherein the first electrochemical sensor comprises a plurality of working, counter and reference electrodes that are grouped together as a unit and positionally distributed in a repeating pattern of units;
a second piercing member coupled to and extending from the base;
a second electrochemical sensor operatively coupled to the second piercing member, wherein the second electrochemical sensor comprises a plurality of working, counter and reference electrodes that are grouped together as a unit and positionally distributed in a repeating pattern of units; and wherein:
the plurality of working electrodes, the plurality of counter electrodes and the plurality of references electrodes in the first electrochemical sensor and the second electrochemical sensor are clustered together in repeating units consisting essentially of one working electrode, one counter electrode and one reference electrode;
at least one of the first or the second electrochemical sensor monitors a concentration of glucose in the patient; and
the first and second piercing members are disposed on the base in a configuration selected so that when the first and second piercing members are inserted into the patient, the first and second sensors are separated by at least 5 millimeters of tissue.

10. The apparatus of claim 9, wherein at least one of the first and the second electrochemical sensor comprise:
an analyte sensing layer disposed on a working electrode; and
an analyte modulating layer disposed on the analyte sensing layer, wherein the analyte modulating layer comprises a composition that modulates the diffusion of glucose diffusing through the analyte modulating layer.

11. The apparatus of claim 9, wherein at least two working electrodes in the first and second electrochemical sensors are coated with glucose oxidase.

12. The apparatus of claim 9, further comprising a processor capable of characterizing a plurality of signals received from the first and second electrochemical sensors.

13. The apparatus of claim 12, wherein the first electrochemical sensor comprises a working electrode coated with glucose oxidase and the second electrochemical sensor comprises no working electrode coated with glucose oxidase and the processor is capable of obtaining information on glucose concentrations in the patient by comparing the signals received from said working electrodes so as to identify a background signal that is not based on a glucose concentrations in the patient.

14. The apparatus of claim 12, wherein the working electrode in the first and second electrochemical sensors are coated with glucose oxidase and the processor is capable of obtaining information on glucose concentrations in the patient by comparing the signals received from said working electrodes coated with glucose oxidase.

15. The apparatus of claim 14, wherein a pulsed voltage is used to obtain a signal from an electrode.

16. The apparatus of claim 9, wherein the processor is capable of comparing a first signal received from a working electrode in response to a first working potential with a second signal received from a working electrode in response to a second working potential.

17. The analyte apparatus of claim 9, wherein:
at least one working electrode in the first and second electrochemical sensors is coated with glucose oxidase; and
at least one working electrode in the first and second electrochemical sensors is not coated with glucose oxidase.

18. The apparatus of claim 9, wherein the plurality of working electrodes, the plurality of counter electrodes and the plurality of reference electrodes are parallel to the planar surface of the base when the analyte sensor apparatus is implanted within the mammal.

* * * * *